(12) United States Patent
Torrens et al.

(10) Patent No.: US 7,888,510 B2
(45) Date of Patent: *Feb. 15, 2011

(54) 2-'4(PHENYLAMINO)-PIPERIDIN-1-YL!-N-PHENYL-ACETAMINE DERIVATIVES AND RELATED COMPOUNDS AS NEUROPEPTIDE Y5 (NPY5) LIGANDS FOR THE TREATMENT OF OBESITY

(75) Inventors: Antoni Jover Torrens, Terrasa (ES); Josep Mas Prio, Rubi (ES); Alberto Dordal Zueras, Barcelona (ES); Maria Angeles Fisas Escasany, Barcelona (ES); Helmut-Heinrich Buschmann, Aachen (DE)

(73) Assignee: Laboratorios del Dr. Esteve S.A., Barcelona (ES)

( * ) Notice: Subject to any disclaimer, the term of this patent is extended or adjusted under 35 U.S.C. 154(b) by 540 days.

This patent is subject to a terminal disclaimer.

(21) Appl. No.: 10/565,979

(22) PCT Filed: Jul. 29, 2004

(86) PCT No.: PCT/EP2004/008508
§ 371 (c)(1),
(2), (4) Date: Nov. 5, 2007

(87) PCT Pub. No.: WO2005/013988
PCT Pub. Date: Feb. 17, 2005

(65) Prior Publication Data
US 2008/0119516 A1 May 22, 2008

(30) Foreign Application Priority Data
Jul. 30, 2003 (ES) .................. 200301813

(51) Int. Cl.
C07D 407/12 (2006.01)
C07D 401/12 (2006.01)
A61K 31/4525 (2006.01)
A61K 31/4545 (2006.01)

(52) U.S. Cl. ............ 546/196; 546/197; 546/200; 546/202; 546/204; 546/206; 546/135; 514/319; 514/320; 514/321; 514/323; 514/324; 514/325

(58) Field of Classification Search .......... 546/135, 546/196, 197, 200, 202, 204, 206; 514/319, 514/320, 321, 323, 324, 325
See application file for complete search history.

(56) References Cited

U.S. PATENT DOCUMENTS

| 6,399,631 B1 | 6/2002 | Elliott et al. |
| 2004/0058920 A1 | 3/2004 | Jover et al. |
| 2004/0067941 A1 | 4/2004 | Torrens Jover et al. |

FOREIGN PATENT DOCUMENTS

| WO | WO 97/19682 | 6/1997 |
| WO | WO 97/20823 | 6/1997 |
| WO | WO 98/24768 | 6/1998 |
| WO | 98/35957 | 8/1998 |
| WO | WO 98/40356 | 9/1998 |
| WO | WO 99/40091 | 8/1999 |
| WO | WO 00/20376 | 4/2000 |
| WO | 01/07409 | 2/2001 |
| WO | 01/09120 | 2/2001 |
| WO | WO 01/13917 A1 | 3/2001 |
| WO | WO 03/010159 A1 * | 6/2003 |
| WO | 03/084939 | 10/2003 |

OTHER PUBLICATIONS

In the Pipeline, online, accessed Jun. 16, 2008, "http://pipeline.corante.com/archives/2006/01/24/the_examiner_finally_snaps.php").*

(Continued)

Primary Examiner—Rita J Desai
Assistant Examiner—David K O'Dell
(74) Attorney, Agent, or Firm—Oblon, Spivak, McClelland, Maier & Neustadt, L.L.P.

(57) ABSTRACT

It was an object of the present invention to provide novel compounds that are suitable in particular as active substances in medicaments, preferably in medicaments for the regulation of neuropeptide Y receptors, particularly preferably of neuropeptide Y5 (NPY5) receptor, for the regulation of food ingestion (food intake), preferably for the prophylaxis and/or treatment of disorders of food ingestion, such as obesity, anorexia, cachexia, bulimia or type II (non insulin dependent) diabetes, for the prophylaxis and/or treatment of disorders of the peripheral nervous system, disorders of the central nervous system, anxiety, depression, cognitive disorders, preferably memory disorders, cardiovascular diseases, pain, epilepsy, arthritis, hypertensive syndrome, inflammatory diseases, immune diseases and other NPY5 mediated disorders in animals and mammals, including man. Said object was achieved by providing 1,4-disubstituted piperidine compounds of general formula (I) wherein the substituents are defined in claim 1.

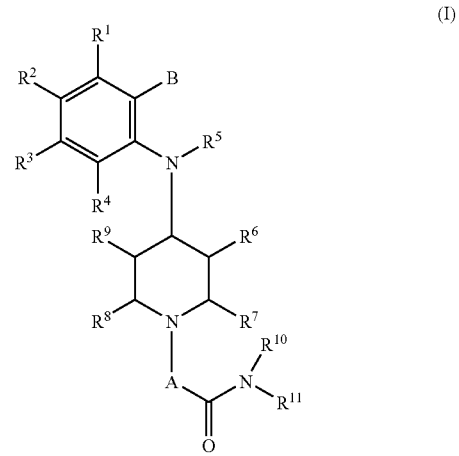

6 Claims, No Drawings

OTHER PUBLICATIONS

Poindexter G. S. et al. Bioorganic and Medicinal Chemistry Letters 2002, 12, 379-382.*

Leslie C. P. Bioorganic and Medicinal Chemistry Letters 2007, 17, 1043-1046.*

Finn J. et al Bioorganic and Medicinal Chemistry Letters 2002, 12, 1771-1774.*

Jablonowski, J.A. et al. Bioorganic and Medicinal Chemistry Letters 2004, 14, 1239-124.*

West, Anthony R., Solid State Chemistry and its Applications, Wiley, New York, 1988, pp. 358 & 365.*

Kazuhiko Tatemoto, et al., "Neuropeptide Y—a novel brain peptide with structural similarities to peptide YY and pancreatic polypeptide", Nature, vol. 296, Apr. 15, 1982, pp. 659-660.

John T. Clark, et al., "Neuropeptide Y and Human Pancreatic Polypeptide Stimulate Feeding Behavior in Rats", Endocrinology, vol. 115, No. 1, Feb. 20, 1984, pp. 427-429.

A. S. Levine, et al., "Neuropeptide Y: A Potent Inducer of Consummatory Behavior in Rats", Peptides, vol. 5, 1984, pp. 1025-1029.

B. Glenn Stanley, et al., "Neuropeptide Y: Stimulation of Feeding and Drinking by Injection into the Paraventricular Nucleus", Life Sciences, vol. 35, No. 26, 1984, pp. 2635-2642.

James F. Flood, et al., "Modulation of memory processing by neuropeptide Y", Brain Research, vol. 421, 1987, pp. 280-290.

John P. Redrobe, et al., "Multiple receptors for neuropeptide Y in the hippocampus: putative roles in seizures and cognition", Brain Research, vol. 848, 1999, pp. 153-166.

Markus Heilig, et al., "Anxiolytic-like effect of neuropeptide Y (NPY), but not other peptides in an operant conflict test", Regulatory Peptides, vol. 41, 1992, pp. 61-69.

Markus Heilig, et al., "Antidepressant drugs increase the concentration of neuropeptide Y (NPY)-like immunoreactivity in the rat brain", European Journal of Pharmacology, vol. 147, 1988, pp. 465-467.

Martin C. Michel, et al., "Neuropeptide Y: a possible role in hypertension?", Journal of Hypertension, vol. 13, No. 4, pp. 385-395.

Donald R. Gehlert, "Subtypes of Receptors for Neuropeptide Y: Implications for the Targeting of Therapeutics", Life Sciences, vol. 55, No. 8, 1994, pp. 551-562.

Philip A. Hipskind, et al., "Section I. Central Nervous System Diseases", Ann. Rep. Med. Chem., 1996, pp. 1-10.

Lars Grundemar, et al., "Neuropeptide Y effector systems: perspectives for drug development", Tips Reviews, vol. 15, pp. 153-159.

Yvan Dumont, et al., "BIIE0246, a potent and highly selective non-peptide neuropeptide Y $Y_2$ receptor antagonist", British Journal of Pharmacology, vol. 129, No. 6, 2000, pp. 1075-1088.

Christophe Gerald, et al., "A receptor subtype involve in neuropeptide-Y-induced food intake", Nature, vol. 382, Jul. 11, 1996, pp. 168-171.

Yinghe Hu, et al., "Identification of a Novel Hypothalamic Neuropeptide Y Receptor Associated with Feeding Behavior", The Journal of Biological Chemistry, vol. 271, No. 42, Oct. 18, 1996, pp. 26315-26319.

Yvan Dumont, et al., "Characterization of Neuropeptide Y Binding Sites in Rat Brain Membrane Preparations Using [$^{125}$I]Leu$^{31}$, Pro$^{34}$]Peptide YY and [$^{125}$I]Peptide YY $_{3-36}$ as Selective $Y_1$ and $Y_2$ Radioligands$^1$", The Journal of Pharmacology and experimental Therapeutics, vol. 272, No. 2, 1995, pp. 673-680.

Ants Kask, et al., "Neuropeptide Y $Y_5$ receptor antagonist CGP71683A: the effects on food intake and anxiety-related behavior in the rat", European Journal of Pharmacology, vol. 414, 2001, pp. 215-224.

Andrew V. Turnbull, et al., "Selective Antagonism of the NPY Y5 Receptor Does Not Have a Major Effect on Feeding in Rats", Diabetes, vol. 51, Aug. 2002, pp. 2441-2449.

B. Glenn Stanley, et al., "Neuropeptide Y injected in the paraventricular hypothalamus: A powerful stimulant of feeding behavior", Proc. Natl. Acad. Sci. USA, vol. 82, Jun. 1985, pp. 3940-3943.

U.S. Appl. No. 10/566,402, filed Jan. 30, 2006, Torrens Jover, et al.
U.S. Appl. No. 10/566,100, filed Jan. 27, 2006, Torrens Jover, et al.
U.S. Appl. No. 10/566,399, filed Jan. 30, 2006, Torrens Jover, et al.

* cited by examiner

2-'4(PHENYLAMINO)-PIPERIDIN-1-YL!-N-PHENYL-ACETAMINE DERIVATIVES AND RELATED COMPOUNDS AS NEUROPEPTIDE Y5 (NPY5) LIGANDS FOR THE TREATMENT OF OBESITY

The present invention relates to 1,4-disubstituted piperidine compounds of general formula (I), methods for their preparation, medicaments comprising these compounds as well as their use for the preparation of a medicament for the treatment of humans or animals.

Neuropeptide Y (NPY), first isolated in porcine brain extracts (Tatemoto et. al. Nature 1982, 296, 659), is a 36-amino acid peptide belonging to the family of pancreatic polypeptides, and is one of the most abundant peptides in the brain and in the central nervous system. In addition, NPY is also distributed in several parts of the peripheral nervous system.

Several studies suggest a significant role of NPY in food ingestion regulation and particularly in food dysfunctions like obesity, anorexia and bulimia. Specifically, NPY is a powerful stimulant of food ingestion. Thus, appetite is significantly increased when NPY is injected directly into the CNS of satiated mice (Clark J. T. et. al. Endocrinology 1984, 115, 427; Levine A. S. et. al. Peptides 1984, 5, 1025; Stanley B. G. et. al. Life Sci. 1984, 35, 2635; Stanley B. G. et. al. Proc. Nat. Acad. Sci. USA 1985, 82, 3940). On the other hand, NPY may play a role in cognitive function regulation, e.g. memory (Flood J. F. et. al. Brain Res. 1987, 421, 280; Redrobe J. P. et. Al. Brain Res. 1999, 848, 153), and be active in anxiety (Heilig M. et. al. Reg. Peptides 1992, 41, 61) and depression (Heilig M. et. al. Eur. J. Pharmacol. 1988, 147, 465) processes.

NPY is also distributed in the peripheral system. Some studies suggest that it might be involved in hypertensive (Michel M. C: et. al. J. Hypertens. 1995, 13, 385), and analgesic (Gehlert D. R. Life Sci. 1994, 55, 551) processes, among others.

The endogenous proteins that constitute NPY-binding receptors have been widely studied. Several have been cloned and expressed. At present, six different receptor subtypes, named Y1 to Y6, are recognized (Hispkind P. A. et. al. Annu. Rep. Med. Chem. 1996, 31, 1; Grundemar L. et. al. TIPS Reviews, 15, 153, 1994). Each NPY receptor subtype is generally associated to a different biological activity. For example, Y2 receptor is involved in the induction of convulsions in rats (Dumont Y. et. al. Brit. J. Pharmacol. 2000, 129, 1075).

The most recently identified receptor is Y5 (Hu et. al. J. Biol. Chem. 1996, 271, 26315). There is evidence that Y5 receptor has a unique pharmacological profile related to food ingestion as compared to the other receptor subtypes. The fact that [D-Trp$^{32}$]NPY peptide, a selective Y5-receptor agonist with no affinity for Y1 receptor, stimulates food ingestion in rats (Gerald C. et. al. Nature, 1996, 382, 168), supports the hypothesis that Y5 receptor is related to exaggerated food consumption. Consequently, compounds having an affinity to the Y5 receptor should be effective to inhibit food ingestion and very useful to control diseases like obesity or other disorders of food ingestion (food intake), such as anorexia, bulimia, cachexia or type II diabetes. Moreover, it has been suggested that such compounds are useful to control diseases such as arthritis or epilepsy.

Several NPY5 non-peptidic antagonists have been described. Thus, 2-aminoquinazoline derivatives [PCT Int. Appl. WO 9720823, 1997 (Novartis AG)], sulfonamides [PCT Int. Appl. WO 9719682, 1997 (Synaptic Pharmaceutical Corp.)], pyrazoles [PCT Int. Appl. WO 9824768, 1998 (Banyu Pharmaceutical Co., Ltd)], aminopyridines [PCT Int. Appl. WO 9840356, 1998 (Banyu Pharmaceutical Co., Ltd)], N-aralkyl-2-tetralinamines [PCT Int. Appl. WO 0020376, 2000 (Ortho McNeil Pharmaceutical Inc.)], several amides [PCT Int. Appl. WO 9835957, 1998 (Bayer Corp.)], pyridine and pyrimidine derivatives [PCT Int. Appl. WO 9940091, 1999 (Amgen Inc.)], carbazoles [PCT Int. Appl. WO 0107409, 2001 (Astra Zeneca AB.)], and spiroisoquinolinones [PCT Int. Appl. WO 0113917, 2001 (Bristol-Myers Squibb Co.)], have been prepared.

Thus, it was an object of the present invention to provide novel compounds that are suitable in particular as active substances in medicaments, preferably in medicaments for the regulation of neuropeptide Y receptors, particularly preferably of neuropeptide Y 5 (NPY5) receptor, for the regulation of food ingestion (food intake), preferably for the prophylaxis and/or treatment of disorders of food ingestion, such as obesity, anorexia, cachexia, bulimia or type II (non insulin dependent) diabetes, for the prophylaxis and/or treatment of disorders of the peripheral nervous system, disorders of the central nervous system, anxiety, depression, cognitive disorders, preferably memory disorders, cardiovascular diseases, pain, epilepsy, arthritis, hypertensive syndrome, inflammatory diseases, immune diseases and other NPY5 mediated disorders in animals and mammals, including man.

Said object was achieved by providing 1,4-disubstituted piperidine compounds of general formula (I),

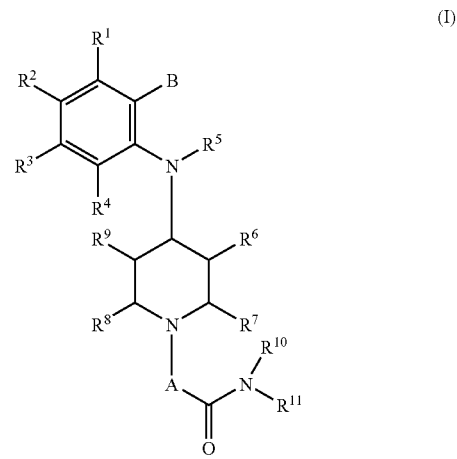

wherein $R^1$, $R^2$, $R^3$, $R^4$ are each independently selected from the group consisting of hydrogen, halogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical, which may be bonded via an optionally at least mono-substituted alkylene group and/or may be condensed with an optionally at least mono-substituted mono- or polycyclic ring-system, an optionally at least mono-substituted aryl- or heteroaryl radical, which may be bonded via an optionally at least mono-substituted alkylene group and/or may be condensed with an optionally at least mono-substituted mono- or polycyclic ringsystem, a nitro, cyano, —OR$^{12}$, —OC(=O) R$^{13}$, —SR$^{14}$, —SOR$^{14}$, —SO$_2$R$^{14}$, —NH—SO$_2$R$^{14}$, —SO$_2$NH$_2$, —NR$^{15}$R$^{16}$ moiety and —O—P.

$R^5$ represents hydrogen, an unbranched or branched, saturated or unsaturated, optionally at least mono-substituted aliphatic radical, or a saturated or unsaturated, optionally at least mono-substituted cycloaliphatic radical, $R^6$, $R^7$, $R^8$, $R^9$ are each independently selected from the group consisting of hydrogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical, a cyano and a $COOR^{17}$ moiety, A represents a bridge member —$CHR^{18}$— or —$CHR^{18}$—$CH_2$—, B represents an unbranched or branched, saturated or unsaturated, optionally at least mono-substituted aliphatic radical, a saturated or unsaturated, optionally at least mono-substituted cycloaliphatic radical, a $COOR^{19}$-moiety, a —(C=O)$R^{20}$-moiety, or a —$CH_2OR^{23}$-moiety, $R^{10}$ represents hydrogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical or an optionally at least mono-substituted aryl- or heteroaryl radical, which may be bonded via an optionally at least mono-substituted alkylene group and/or may be condensed with an optionally at least mono-substituted mono- or polycyclic ring-system, $R^{11}$ represents an unbranched or branched, saturated or unsaturated, optionally at least mono-substituted aliphatic radical, a saturated or unsaturated, optionally at least mono-substituted, optionally at least one heteroatom as ring member containing cycloaliphatic radical, which may be bonded via an optionally at least mono-substituted alkylene group and/or may be condensed with an optionally at least mono-substituted mono- or polycyclic ringsystem, or an optionally at least mono substituted aryl- or heteroaryl radical, which may be bonded via an optionally at least mono-substituted alkylene group and/or may be condensed with an optionally at least mono-substituted mono- or polycyclic ringsystem, or $R^{10}$ and $R^{11}$ together with the bridging nitrogen atom form an optionally at least mono-substituted, saturated, unsaturated or aromatic heterocyclic ring that may contain at least one further heteroatom as a ring member and/or may be condensed with an optionally at least mono-substituted mono- or polycyclic ringsystem, $R^{12}$ represents hydrogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical, which may be bonded via an optionally at least mono-substituted alkylene group and/or may be condensed with an optionally at least mono-substituted mono- or polycyclic ring-system, or an optionally at least mono-substituted aryl- or heteroaryl radical, which may be bonded via an optionally at least mono-substituted alkylene group and/or may be condensed with an optionally at least mono-substituted mono- or polycyclic ring-system, $R^{13}$ represents hydrogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical, which may be bonded via an optionally at least mono-substituted alkylene group and/or may be condensed with an optionally at least mono-substituted mono- or polycyclic ring-system, or an optionally at least mono-substituted aryl- or heteroaryl radical, which may be bonded via an optionally at least mono-substituted alkylene group and/or may be condensed with an optionally at least mono-substituted mono- or polycyclic ring-system, $R^{14}$ represents an unbranched or branched, saturated or unsaturated, optionally at least mono-substituted aliphatic radical, a saturated or unsaturated, optionally at least mono-substituted, optionally at least one heteroatom as ring member containing cycloaliphatic radical, which may be bonded via an optionally at least mono-substituted alkylene group and/or may be condensed with an optionally at least mono-substituted mono- or polycyclic ring-system, or an optionally at least mono-substituted aryl- or heteroaryl radical, which may be bonded via an optionally at least mono-substituted alkylene group and/or may be condensed with an optionally at least mono-substituted mono- or polycyclic ring-system, $R^{15}$ and $R^{16}$ each are independently selected from the group consisting of hydrogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical, which may be bonded via an optionally at least mono-substituted alkylene group and/or may be condensed with an optionally at least mono-substituted mono- or polycyclic ring-system, or an optionally at least mono-substituted aryl- or heteroaryl radical, which may be bonded via an optionally at least mono-substituted alkylene group and/or may be condensed with an optionally at least mono-substituted mono- or polycyclic ring-system, or $R^{15}$ and $R^{16}$ together with the bridging nitrogen atom form a saturated, unsaturated or aromatic heterocyclic ring, which may be at least mono-substituted and/or contain at least one further heteroatom as a ring member, $R^{17}$ represents hydrogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical or an optionally at least mono-substituted aryl- or heteroaryl radical, which may be bonded via an optionally at least mono-substituted alkylene group and/or may be condensed with an optionally at least mono-substituted mono- or polycyclic ring-system, $R^{18}$ represents hydrogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical or an optionally at least mono-substituted aryl- or heteroaryl radical, which may be bonded via an optionally at least mono-substituted alkylene group and/or may be condensed with an optionally at least mono-substituted mono- or polycyclic ring-system, $R^{19}$ represents hydrogen, an unbranched or branched, saturated or unsaturated, optionally at least mono-substituted aliphatic radical, a saturated or unsaturated, optionally at least mono-substituted cycloaliphatic radical, or an optionally at least mono-substituted aryl- or heteroaryl radical, which may be condensed with an optionally at least mono-substituted mono- or polycyclic ring-system, $R^{20}$ represents hydrogen, an unbranched or branched, saturated or unsaturated, optionally at least mono-substituted aliphatic radical, a saturated or unsaturated, optionally at least mono-substituted cycloaliphatic radical, an optionally at least mono-substituted aryl- or heteroaryl radical, which may be condensed with an optionally at least mono-substituted mono- or polycyclic ring-system, or a $NR^{21}R^{22}$-moiety, $R^{21}$ represents hydrogen, an unbranched or branched, saturated or unsaturated, optionally at least mono-substituted aliphatic radical, a saturated or unsaturated, optionally at least mono-substituted cycloaliphatic radical, or an optionally at least mono-substituted aryl- or heteroaryl radical, which may be condensed with an optionally at least mono-substituted mono- or polycyclic ring-system, $R^{22}$ represents hydrogen, an unbranched or branched, saturated or unsaturated, optionally at least mono-substituted aliphatic radical, a saturated or unsaturated, optionally at least mono-substituted cycloaliphatic radical, or an optionally at least mono-substituted aryl- or heteroaryl radical, which may be condensed with an optionally at least mono-substituted mono- or polycyclic ring-system, $R^{23}$ represents hydrogen, an unbranched or branched, saturated or unsaturated, optionally at least mono-substituted aliphatic radical, which may comprise at least one heteroatom as a chain member, or a —(C=O)$R^{13}$-moiety, P represents hydrogen, a linear or branched $C_{1-3}$ alkyl radical, —PO(O—$C_{1-4}$-Alkyl), —CO(O$C_{1-5}$-Alkyl),

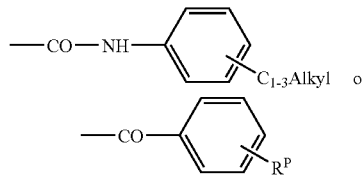

and $R^P$ represents —OCO—$C_{1-3}$-Alkyl, —$CH_2$—N($C_{1-4}$-Alkyl)$_2$ or

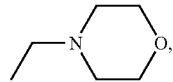

optionally in form of one of its stereoisomers, preferably enantiomers or diastereomers, its racemate or in form of a mixture of at least two of its stereoisomers, preferably enantiomers or diastereomers, in any mixing ratio, or a salt, preferably a physiologically acceptable salt thereof, or a corresponding solvate, respectively.

Preferred are 1,4-disubstituted piperidine compounds of general formula (I) given above, wherein $R^1$, $R^2$, $R^3$, $R^4$ are each independently selected from the group consisting of hydrogen, halogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical, which may be bonded via an optionally at least mono-substituted alkylene group and/or may be condensed with an optionally at least mono-substituted mono- or polycyclic ring-system, an optionally at least mono-substituted aryl- or heteroaryl radical, which may be bonded via an optionally at least mono-substituted alkylene group and/or may be condensed with an optionally at least mono-substituted mono- or polycyclic ringsystem, a nitro, cyano, —$OR^{12}$, —OC(=O)$R^{13}$, —$SR^{14}$, —$SOR^{14}$, —$SO_2R^{14}$, —NH—$SO_2R^{14}$, —$SO_2NH_2$, —$NR^{15}R^{16}$ moiety and —O—P, $R^5$ represents hydrogen, an unbranched or branched, saturated or unsaturated, optionally at least mono-substituted aliphatic radical, or a saturated or unsaturated, optionally at least mono-substituted cycloaliphatic radical, $R^6$, $R^7$, $R^8$, $R^9$ are each independently selected from the group consisting of hydrogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical, a cyano-moiety and a —$COOR^{17}$ moiety, A represents a bridge member —$CHR^{18}$— or —$CHR^{18}$—$CH_2$—, B represents an unbranched or branched, saturated or unsaturated, optionally at least mono-substituted aliphatic radical, a saturated or unsaturated, optionally at least mono-substituted cycloaliphatic radical, a $COOR^{19}$-moiety, a —(C=O)$R^{20}$-moiety, or a —$CH_2OR^{23}$-moiety, $R^{10}$ represents hydrogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical, or an optionally at least mono-substituted aryl- or heteroaryl radical, which may be bonded via an optionally at least mono-substituted alkylene group and/or may be condensed with an optionally at least mono-substituted mono- or polycyclic ring-system, $R^{11}$ represents an unbranched or branched, saturated or unsaturated, optionally at least mono-substituted aliphatic radical, a saturated or unsaturated, optionally at least mono-substituted, optionally at least one heteroatom as ring member containing cycloaliphatic radical, which may be bonded via an optionally at least mono-substituted alkylene group and/or may be condensed with an optionally at least mono-substituted mono- or polycyclic ringsystem, or an optionally at least mono substituted aryl- or heteroaryl radical, which may be bonded via an optionally at least mono-substituted alkylene group and/or may be condensed with an optionally at least mono-substituted mono- or polycyclic ringsystem, or $R^{10}$ and $R^{11}$ together with the bridging nitrogen atom form an optionally at least mono-substituted, saturated, unsaturated or aromatic heterocyclic ring that may contain at least one further heteroatom as a ring member and/or may be condensed with an optionally at least mono-substituted mono- or polycyclic ringsystem, $R^{12}$ represents hydrogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical, which may be bonded via an optionally at least mono-substituted alkylene group and/or may be condensed with an optionally at least mono-substituted mono- or polycyclic ring-system, or an optionally at least mono-substituted aryl- or heteroaryl radical, which may be bonded via an optionally at least mono-substituted alkylene group and/or may be condensed with an optionally at least mono-substituted mono- or polycyclic ring-system, $R^{13}$ represents hydrogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical, which may be bonded via an optionally at least mono-substituted alkylene group and/or may be condensed with an optionally at least mono-substituted mono- or polycyclic ring-system, or an optionally at least mono-substituted aryl- or heteroaryl radical, which may be bonded via an optionally at least mono-substituted alkylene group and/or may be condensed with an optionally at least mono-substituted mono- or polycyclic ring-system, $R^{14}$ represents an unbranched or branched, saturated or unsaturated, optionally at least mono-substituted aliphatic radical, a saturated or unsaturated, optionally at least mono-substituted, optionally at least one heteroatom as ring member containing cycloaliphatic radical, which may be bonded via an optionally at least mono-substituted alkylene group and/or may be condensed with an optionally at least mono-substituted mono- or polycyclic ring-system, or an optionally at least mono-substituted aryl- or heteroaryl radical, which may be bonded via an optionally at least mono-substituted alkylene group and/or may be condensed with an optionally at least mono-substituted mono- or polycyclic ring-system, $R^{15}$ and $R^{16}$ are each independently selected from the group consisting of hydrogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical, which may be bonded via an optionally at least mono-substituted alkylene group and/or may be condensed with an optionally at least mono-substituted mono- or polycyclic ring-system, or an optionally at least mono-substituted aryl- or heteroaryl radical, which may be bonded via an optionally at least mono-substituted alkylene group and/or may be condensed with an optionally at least mono-substituted mono- or polycyclic ring-system, or $R^{15}$ and $R^{16}$ together with the bridging nitrogen atom form a saturated, unsaturated or aromatic heterocyclic ring, which may be at least mono-substituted and/or contain at least one further heteroatom as ring member, $R^{17}$ represents hydrogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical, or an optionally at least mono-substituted aryl- or heteroaryl radical, which may be bonded via an optionally at least mono-substituted alkylene group and/or may be condensed with an optionally at least mono-substituted mono- or polycyclic ring-system, $R^{18}$ represents hydrogen, an unbranched or branched, saturated or unsaturated, optionally at least mono-substituted aliphatic radical, a saturated or unsaturated, optionally at least mono-substituted, optionally at least one heteroatom as ring member containing cycloaliphatic radical, or an optionally at least mono-substituted aryl- or heteroaryl radical, which may be bonded via an optionally at least mono-substituted alkylene group and/or may be condensed with an optionally at least mono-substituted mono- or polycyclic ring-system, $R^{19}$ represents hydrogen, an unbranched or branched, saturated or unsaturated, optionally at least mono-substituted aliphatic radical, a saturated or unsaturated, optionally at least mono-substituted cycloaliphatic radical, or an optionally at least mono-substituted aryl- or heteroaryl radical, which may be condensed with an optionally at least mono-substituted mono- or polycyclic ring-system, $R^{20}$ represents hydrogen, an unbranched or branched, saturated or unsaturated, optionally at least mono-substituted aliphatic radical, a saturated or unsaturated, optionally at least mono-substituted cycloaliphatic radical, an optionally at least mono-substituted aryl- or heteroaryl radical, which may be condensed with an optionally at least mono-substituted mono- or polycyclic ring-system, or a $NR^{21}R^{22}$-moiety, $R^{21}$ represents hydrogen, an unbranched or branched, saturated or unsaturated, optionally at least mono-substituted aliphatic radical, a saturated or unsaturated, optionally at least mono-substituted cycloaliphatic radical, or an optionally at least mono-substituted aryl- or heteroaryl radical, which may be condensed with an optionally at least mono-substituted mono- or polycyclic ring-system, $R^{22}$ represents hydrogen, an unbranched or branched, saturated or unsaturated, optionally at least mono-substituted aliphatic radical, a saturated or unsaturated, optionally at least mono-substituted cycloaliphatic radical, or an optionally at least mono-substituted aryl- or heteroaryl radical, which may be condensed with an optionally at least mono-substituted mono- or polycyclic ring-system, $R^{23}$ represents hydrogen, an unbranched or branched, saturated or unsaturated, optionally at least mono-substituted aliphatic radical, which may comprise at least one heteroatom as a chain member, or a —(C=O)$R^{13}$-moiety, P represents hydrogen, a linear or branched $C_{1-3}$ alkyl radical, —PO(O—$C_{1-4}$-Alkyl), —CO(O$C_{1-5}$-Alkyl),

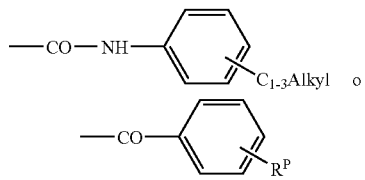

and $R^P$ represents ortho —OCO—$C_{1-3}$-Alkyl, —CH$_2$—N($C_{1-4}$-Alkyl)$_2$ in the meta or para position of the phenyl ring or

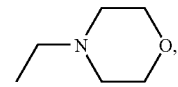

in the meta or para position of the phenyl ring, optionally in form of one of their stereoisomers, preferably enantiomers or diastereomers, their racemates or in form of a mixture of at least two of its stereoisomers, preferably enantiomers or diastereomers, in any mixing ratio, or salts thereof, preferably physiologically acceptable salts thereof, or corresponding solvates.

A mono- or polycyclic ring-system according to the present invention means a mono- or polycyclic hydrocarbon ring-system that may be saturated, unsaturated or aromatic. If the ring system is polycyclic, each of its different rings may show a different degree of saturation, i.e. it may be saturated, unsaturated or aromatic. Optionally each of the rings of the mono- or polycyclic ring system may contain one or more heteroatoms as ring members, which may be identical or different and which can preferably be selected from the group consisting of N, O, S and P, more preferably be selected from the group consisting of N, O and S. Preferably the polycyclic ring-system may comprise two rings that are condensed. The rings of the mono- or polycyclic ring-system are preferably 5- or 6-membered.

If one or more of the residues $R^1$-$R^{23}$ and B represents an aliphatic radical, which is substituted by one or more substituents, unless defined otherwise, each of these substituents may preferably be selected from the group consisting of hydroxy, halogen, branched or unbranched $C_{1-4}$-alkoxy, branched or unbranched $C_{1-4}$-perfluoroalkoxy, branched or unbranched $C_{1-4}$-perfluoroalkyl, amino, carboxy, amido, cyano, nitro, —SO$_2$NH$_2$, —CO—$C_{1-4}$-alkyl, —SO—$C_{1-4}$- alkyl, —SO$_2$—C$_{1-4}$-alkyl, —NH—SO$_2$—C$_{1-4}$-alkyl, wherein the C$_{1-4}$-alkyl may in each case be branched or unbranched, an unsubstituted or at least mono-substituted phenyl or naphthyl radical and an unsubstituted or at least mono-substituted furanyl-, thienyl-, pyrrolyl-, imidazolyl-, pyrazolyl-, pyridinyl-, pyrimidinyl-, quinolinyl- and isoquinolinyl radical, more preferably be selected from the group consisting of hydroxy, F, Cl, Br, methoxy, ethoxy, CF$_3$ and an unsubstituted phenyl radical. If any one of these substituents itself is at least mono-substituted, said substituents may preferably be selected from the group consisting of F, Cl, methyl and methoxy.

If one or more of the residues R$^1$-R$^{22}$ and B represents or comprises a cycloaliphatic radical, which is substituted by one or more substituents, unless defined otherwise, each of these substituents may preferably be selected from the group consisting of hydroxy, halogen, branched or unbranched C$_{1-4}$-alkyl, branched or unbranched C$_{1-4}$-alkoxy, branched or unbranched C$_{1-4}$-perfluoroalkoxy, phenoxy, benzoyl, cyclohexyl, branched or unbranched C$_{1-4}$-perfluoroalkyl, —NR$^A$R$^B$ wherein R$^A$, R$^B$ are each independently selected from the group consisting of H, a branched or unbranched C$_{1-4}$-alkyl-radical, —CH$_2$—CH$_2$—OH and phenyl, carboxy, amido, cyano, nitro, —SO$_2$NH$_2$, —CO—C$_{1-4}$-alkyl, —CO—OC$_{1-4}$-alkyl, —SO—C$_{1-4}$-alkyl, —SO$_2$—C$_{1-4}$-alkyl, —NH—SO$_2$—C$_{1-4}$-alkyl, wherein C$_{1-4}$-alkyl may in each case be branched or unbranched, unsubstituted or at least mono-substituted phenyl or naphthyl and an unsubstituted or at least mono-substituted furanyl-, thienyl-, pyrrolyl-, imidazolyl-, pyrazolyl-, pyridinyl-, pyrimidinyl-, quinolinyl- and isoquinolinyl radical, more preferably be selected from the group consisting of hydroxy, F, Cl, Br, methyl, ethyl, methoxy, ethoxy, benzoyl, phenoxy, cyclohexyl, —CF$_3$, —CO—CH$_3$, —CO—OCH$_3$, —NR$^A$R$^B$ wherein R$^A$, R$^B$ are each independently selected from the group consisting of H, a branched or unbranched C$_{1-4}$-alkyl-radical, —CH$_2$—CH$_2$—OH and phenyl, and an unsubstituted phenyl radical. If any one of these substituents itself is at least mono-substituted, said substituents may preferably be selected from the group consisting of F, Cl, methyl and methoxy.

If one or more of the residues R$^1$-R$^4$ and R$^{10}$-R$^{18}$ comprises an alkylene group, which is substituted by one or more substituents, unless defined otherwise, each of these substituents may preferably be selected from the group consisting of hydroxy, halogen, branched or unbranched C$_{1-4}$-alkoxy, branched or unbranched C$_{1-4}$-perfluoroalkoxy, branched or unbranched C$_{1-4}$-perfluoroalkyl, amino, carboxy, amido, cyano, nitro, —SO$_2$NH$_2$, —CO—C$_{1-4}$-alkyl, —SO—C$_{1-4}$-alkyl, —SO$_2$—C$_{1-4}$-alkyl, —NH—SO$_2$—C$_{1-4}$-alkyl, wherein C$_{1-4}$-alkyl may be branched or unbranched, an unsubstituted or at least mono-substituted phenyl or naphthyl radical and an unsubstituted or at least mono-substituted furanyl-, thienyl-, pyrrolyl-, imidazolyl-, pyrazolyl-, pyridinyl-, pyrimidinyl-, quinolinyl- and isoquinolinyl radical, more preferably be selected from the group consisting of hydroxy, F, Cl, Br, methoxy, ethoxy, CF$_3$ and unsubstituted phenyl. If any one of these substituents itself is at least mono-substituted, said substituents may preferably be selected from the group consisting of F, Cl, methyl and methoxy.

If one or more of the residues R$^1$-R$^4$ and R$^{10}$-R$^{22}$ comprises a mono- or polycyclic ringsystem, which is substituted by one or more substituents, unless defined otherwise, each of these substituents may preferably be selected from the group consisting of hydroxy, halogen, branched or unbranched C$_{1-4}$-alkyl, branched or unbranched C$_{1-4}$-alkoxy, branched or unbranched C$_{1-4}$-perfluoroalkoxy, branched or unbranched C$_{1-4}$-perfluoroalkyl, amino, carboxy, amido, cyano, keto, nitro, —SO$_2$NH$_2$, —CO—C$_{1-4}$-alkyl, —SO—C$_{1-4}$-alkyl, —SO$_2$—C$_{1-4}$-alkyl, —NH—SO$_2$—C$_{1-4}$-alkyl, wherein C$_{1-4}$-alkyl may be branched or unbranched, an unsubstituted or at least mono-substituted phenyl or naphthyl radical and unsubstituted or at least mono-substituted furanyl-, thienyl-, pyrrolyl-, imidazolyl-, pyrazolyl-, pyridinyl-, pyrimidinyl-, quinolinyl- and isoquinolinyl, more preferably from the group consisting of hydroxy, F, Cl, Br, methyl, ethyl, methoxy, ethoxy, CF$_3$, keto (=O), cyano and an unsubstituted phenyl radical. If any one of these substituents itself is at least mono-substituted, said substituents may preferably be selected from the group consisting of F, Cl, methyl and methoxy.

If one or more of the residues R$^1$-R$^4$ and R$^{10}$-R$^{22}$ represents or comprises an aryl radical, which is substituted by one or more substituents, unless defined otherwise, each of these substituents may preferably be selected from the group consisting of hydroxy, halogen, branched or unbranched C$_{1-4}$-alkoxy, branched or unbranched C$_{1-4}$-alkyl, branched or unbranched C$_{1-4}$-perfluoroalkoxy, unsubstituted or at least mono-substituted phenoxy, unsubstituted or at least mono-substituted benzoyl, cyclohexyl, branched or unbranched C$_{1-4}$-perfluoroalkyl, NR$^A$R$^B$ wherein R$^A$, R$^B$ are each independently selected from the group consisting of H, a branched or unbranched C$_{1-4}$-alkyl-radical, —CH$_2$—CH$_2$—OH and phenyl, carboxy, amido, cyano, —C(H)(OH)(phenyl), —C(H)(OH)(CH$_3$), nitro, —SO$_2$NH$_2$, —CO—C$_{1-4}$-alkyl, —CO—OC$_{1-4}$-alkyl, —SO—C$_{1-4}$-alkyl, —SO$_2$—C$_{1-4}$-alkyl, —NH—SO$_2$—C$_{1-4}$-alkyl, wherein C$_{1-4}$-alkyl may be branched or unbranched, an unsubstituted or at least mono-substituted phenyl or naphthyl radical and unsubstituted or at least mono-substituted furanyl-, thienyl-, pyrrolyl-, imidazolyl-, pyrazolyl-, pyridinyl-, pyrimidinyl-, quinolinyl- and isoquinolinyl radical, more preferably be selected from the group consisting of hydroxy, F, Cl, Br, methyl, ethyl, cyano, —C(H)(OH)(phenyl), —C(H)(OH)(CH$_3$), methoxy, ethoxy, unsubstituted or at least mono-substituted benzoyl, unsubstituted or at least mono-substituted phenoxy, cyclohexyl, CF$_3$, —CO—CH$_3$, —CO—OCH$_3$, —NR$^A$R$^B$ wherein R$^A$, R$^B$ are each independently selected from the group consisting of H, a branched or unbranched C$_{1-4}$-alkyl-radical, —CH$_2$—CH$_2$—OH and phenyl, and an unsubstituted phenyl radical. If any of these substituents itself is at least mono-substituted, said substituents may preferably be selected from the group consisting of F, Cl, methyl and methoxy.

If one or more of the residues R$^1$-R$^4$ and R$^{10}$-R$^{22}$ represents or comprises a heteroaryl radical, which is substituted by one or more substituents, unless defined otherwise, each of these substituents may preferably be selected from the group consisting of hydroxy, halogen, branched or unbranched C$_{1-4}$-alkoxy, branched or unbranched C$_{1-4}$-alkyl, branched or unbranched C$_{1-4}$-perfluoroalkoxy, unsubstituted or at least mono-substituted phenoxy, unsubstituted or at least mono-substituted benzoyl, cyclohexyl, branched or unbranched C$_{1-4}$-perfluoroalkyl, NR$^A$R$^B$ wherein R$^A$, R$^B$ are each independently selected from the group consisting of H, a branched or unbranched C$_{1-4}$-alkyl-radical, —CH$_2$—CH$_2$—OH and phenyl, carboxy, amido, cyano, nitro, —C(H)(OH)(phenyl), —C(H)(OH)(CH$_3$), —SO$_2$NH$_2$, —CO—C$_{1-4}$-alkyl, —CO—OC$_{1-4}$-alkyl, SO—C$_{1-4}$-alkyl, SO$_2$—C$_{1-4}$-alkyl, —NH—SO$_2$—C$_{1-4}$-alkyl, wherein C$_{1-4}$-alkyl may be branched or unbranched, an unsubstituted or at least mono-substituted phenyl or naphthyl radical and an unsubstituted or at least mono-substituted furanyl-, thienyl-, pyrrolyl-, imidazolyl-, pyrazolyl-, pyridinyl-, pyrimidinyl-, quinolinyl- and isoquinolinyl radical, more preferably be selected from the group consisting of hydroxy, F, Cl, Br, methyl, ethyl, cyano, methoxy, ethoxy, unsubstituted or at least mono-substituted benzoyl, unsubstituted or at least mono-substituted phenoxy, cyclohexyl, $CF_3$, —C(H)(OH)(phenyl), —C(H)(OH)($CH_3$), —CO—$CH_3$, —CO—$OCH_3$, —$NR^A R^B$ wherein $R^A$, $R^B$ are each independently selected from the group consisting of H, a branched or unbranched $C_{1-4}$-alkyl-radical, —$CH_2$—$CH_2$—OH and phenyl, and an unsubstituted phenyl radical. If any one of these substituents itself is at least mono-substituted, said substituents may preferably be selected from the group consisting of F, Cl, methyl and methoxy.

If $R^{10}$ and $R^{11}$ and/or $R^{15}$ and $R^{16}$ form a heterocyclic ring, which is substituted by one or more substituents, unless defined otherwise, each of these substituents may preferably be selected from the group consisting of hydroxy, halogen, branched or unbranched $C_{1-4}$-alkoxy, branched or unbranched $C_{1-4}$-alkyl, branched or unbranched $C_{1-4}$-perfluoroalkoxy, branched or unbranched $C_{1-4}$-perfluoroalkyl, amino, carboxy, amido, cyano, nitro, —$SO_2NH_2$, —CO—$C_{1-4}$-alkyl, —SO—$C_{1-4}$-alkyl, —$SO_2$—$C_{1-4}$-alkyl, —NH—$SO_2$—$C_{1-4}$-alkyl, wherein $C_{1-4}$-alkyl may be branched or unbranched, an unsubstituted or at least mono-substituted phenyl or naphthyl radical and an unsubstituted or at least mono-substituted furanyl-, thienyl-, pyrrolyl-, imidazolyl-, pyrazolyl-, pyridinyl-, pyrimidinyl-, quinolinyl- and isoquinolinyl radical, more preferably be selected from the group consisting of hydroxy, F, Cl, Br, methoxy, ethoxy, methyl, $CF_3$ and an unsubstituted phenyl radical. If any of these substituents itself is at least mono-substituted, said substituents may preferably be selected from the group consisting of F, Cl, methyl and methoxy.

If $R^{10}$ and $R^{11}$ and/or $R^{15}$ and $R^{16}$ form a heterocyclic ring, which contains one or more further heteroatoms as ring members, unless defined otherwise, each of these heteroatoms may preferably be selected from the group consisting of N, O and S, more preferably from the group consisting of N and O.

If one or more of the residues $R^1$-$R^{22}$ and B represents a cycloaliphatic radical, which contains one or more heteroatoms as ring members, unless defined otherwise, each of these heteroatoms may preferably be selected from the group consisting of N, O, S and P, more preferably from the group consisting of N, O and S.

If one or more of the residues $R^1$-$R^4$ and $R^{10}$-$R^{22}$ represents or comprises an heteroaryl radical, which contains one or more heteroatoms as ring members, unless defined otherwise, each of these heteroatoms may preferably be selected from the group consisting of N, O, S and P, more preferably from the group consisting of N, O and S.

If $R^{23}$ represents an aliphatic radical, which comprises at least one heteroatom as a chain member, each of these heteroatoms may preferably be O or S, more preferably O.

Preferred compounds of general formula (I) are also those, wherein $R^1$, $R^2$, $R^3$, $R^4$ are each independently selected from the group consisting of H, F, Cl, Br, an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-cycloaliphatic radical, which may be bonded via an optionally at least mono-substituted $C_{1-6}$-alkylene group and/or may be condensed with an optionally at least mono-substituted mono- or polycyclic ring-system, an optionally at least mono-substituted, 5- or 6-membered aryl- or heteroaryl radical, which may be bonded via an optionally at least mono-substituted $C_{1-6}$-alkylene group and/or may be condensed with an optionally at least mono-substituted mono- or polycyclic ringsystem, a nitro, cyano, —$OR^{12}$, —OC(=O)$R^{13}$, —$SR^{14}$, —$SOR^{14}$, —$SO_2R^{14}$, —NH—$SO_2R^{14}$, —$SO_2NH_2$ and —$NR^{15}R^{16}$ moiety, $R^5$ represents hydrogen, an unbranched or branched, saturated or unsaturated, optionally at least mono-substituted $C_{1-6}$-aliphatic radical, or a saturated or unsaturated, optionally at least mono-substituted $C_{3-8}$-cycloaliphatic radical, $R^6$, $R^7$, $R^8$, $R^9$ are each independently selected from the group consisting of hydrogen, an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-cycloaliphatic radical, a cyano-moiety and a $COOR^{17}$ moiety, A represents a bridge member —$CHR^{18}$— or —$CHR^{18}$—$CH_2$—, B represents an unbranched or branched, saturated or unsaturated, optionally at least mono-substituted $C_{1-6}$-aliphatic radical, a saturated or unsaturated, optionally at least mono-substituted $C_{3-8}$-cycloaliphatic radical, a $COOR^{19}$-moiety, a $COR^{20}$-moiety, or a —$CH_2$—$OR^{23}$-moiety, $R^{10}$ represents hydrogen, an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-cycloaliphatic radical or an optionally at least mono-substituted, 5- or 6-membered aryl- or heteroaryl radical, which may be bonded via an optionally at least mono-substituted $C_{1-6}$-alkylene group and/or may be condensed with an optionally at least mono-substituted mono- or polycyclic ring-system, $R^{11}$ represents an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-cycloaliphatic radical, which may be bonded via an optionally at least mono-substituted substituted $C_{1-6}$-alkylene group and/or may be condensed with an optionally at least mono-substituted mono- or polycyclic ringsystem, or an optionally at least mono substituted, 5- or 6-membered aryl- or heteroaryl radical, which may be bonded via an optionally at least mono-substituted $C_{1-6}$-alkylene group and/or may be condensed with an optionally at least mono-substituted mono- or polycyclic ringsystem, or $R^{10}$ and $R^{11}$ together with the bridging nitrogen atom form an optionally at least mono-substituted, saturated, unsaturated or aromatic, 5- or 6-membered heterocyclic ring, which may contain at least one further heteroatom as a ring member and/or may be condensed with an optionally at least mono-substituted mono- or polycyclic ringsystem, $R^{12}$ represents hydrogen, an unbranched or branched, saturated or unsaturated, optionally at least mono-substituted $C_{1-6}$-aliphatic radical, a saturated or unsaturated, optionally at least mono-substituted, optionally at least one heteroatom containing as ring member $C_{3-8}$-cycloaliphatic radical, which may be bonded via an optionally at least mono-substituted $C_{1-6}$-alkylene group and/or may be condensed with an optionally at least mono-substituted mono- or polycyclic ring-system, or an optionally at least mono-substituted, 5- or 6-membered aryl- or heteroaryl radical, which may be bonded via an optionally at least mono-substituted $C_{1-6}$-alkylene group and/or may be condensed with an optionally at least mono-substituted mono- or polycyclic ring-system, $R^{13}$ represents hydrogen, an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-cycloaliphatic radical, which may be bonded via an optionally at least mono-substituted $C_{1-6}$-alkylene group and/or may be condensed with an optionally at least mono-substituted mono- or polycyclic ring-system, or an optionally at least mono-substituted, 5- or 6-membered aryl- or heteroaryl radical, which may be bonded via an optionally at least mono-substituted $C_{1-6}$-alkylene group and/or may be condensed with an optionally at least mono-substituted mono- or polycyclic ring-system, $R^{14}$ represents an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-cycloaliphatic radical, which may be bonded via an optionally at least mono-substituted $C_{1-6}$-alkylene group and/or may be condensed with an optionally at least mono-substituted mono- or polycyclic ring-system, or an optionally at least mono-substituted, 5- or 6-membered aryl- or heteroaryl radical, which may be bonded via an optionally at least mono-substituted $C_{1-6}$-alkylene group and/or may be condensed with an optionally at least mono-substituted mono- or polycyclic ring-system, $R^{15}$ and $R^{16}$ each are independently selected from the group consisting of hydrogen, an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-cycloaliphatic radical, which may be bonded via an optionally at least mono-substituted $C_{1-6}$-alkylene group and/or may be condensed with an optionally at least mono-substituted mono- or polycyclic ring-system, or an optionally at least mono-substituted, 5- or 6-membered aryl- or heteroaryl radical, which may be bonded via an optionally at least mono-substituted $C_{1-6}$-alkylene group and/or may be condensed with an optionally at least mono-substituted mono- or polycyclic ring-system, or $R^{15}$ and $R^{16}$ together with the bridging nitrogen atom form a saturated, unsaturated or aromatic, 5- or 6-membered heterocyclic ring, which may be at least mono-substituted and/or contain at least one further heteroatom as a ring member, $R^{17}$ represents hydrogen, an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-cycloaliphatic radical or an optionally at least mono-substituted, 5- or 6-membered aryl- or heteroaryl radical, which may be bonded via an optionally at least mono-substituted $C_{1-6}$-alkylene group and/or may be condensed with an optionally at least mono-substituted mono- or polycyclic ring-system, $R^{18}$ represents hydrogen, an unbranched or branched, saturated or unsaturated, optionally at least mono-substituted $C_{1-6}$-aliphatic radical, a saturated or unsaturated, optionally at least mono-substituted, optionally at least one heteroatom as ring member containing $C_{3-8}$-cycloaliphatic radical, or an optionally at least mono-substituted, 5- or 6-membered aryl- or heteroaryl radical, which may be bonded via an optionally at least mono-substituted $C_{1-6}$-alkylene group and/or may be condensed with an optionally at least mono-substituted mono- or polycyclic ring-system, $R^{19}$ represents hydrogen, an unbranched or branched, saturated or unsaturated, optionally at least mono-substituted $C_{1-6}$-aliphatic radical, a saturated or unsaturated, optionally at least mono-substituted $C_{3-8}$ cycloaliphatic radical, or an optionally at least mono-substituted, 5- or 6-membered aryl- or heteroaryl radical, which may be condensed with an optionally at least mono-substituted mono- or polycyclic ring-system, $R^{20}$ represents hydrogen, an unbranched or branched, saturated or unsaturated, optionally at least mono-substituted $C_{1-6}$-aliphatic radical, a saturated or unsaturated, optionally at least mono-substituted $C_{3-8}$ cycloaliphatic radical, an optionally at least mono-substituted, 5- or 6-membered aryl- or heteroaryl radical, which may be condensed with an optionally at least mono-substituted mono- or polycyclic ring-system, or a $NR^{21}R^{22}$-moiety, $R^{21}$ represents hydrogen, an unbranched or branched, saturated or unsaturated, optionally at least mono-substituted $C_{1-6}$-aliphatic radical, a saturated or unsaturated, optionally at least mono-substituted $C_{3-8}$ cycloaliphatic radical, or an optionally at least mono-substituted, 5- or 6-membered aryl- or heteroaryl radical, which may be condensed with an optionally at least mono-substituted mono- or polycyclic ring-system, $R^{22}$ represents hydrogen, an unbranched or branched, saturated or unsaturated, optionally at least mono-substituted $C_{1-6}$-aliphatic radical, a saturated or unsaturated, optionally at least mono-substituted $C_{3-8}$ cycloaliphatic radical, or an optionally at least mono-substituted, 5- or 6-membered aryl- or heteroaryl radical, which may be condensed with an optionally at least mono-substituted mono- or polycyclic ring-system, $R^{23}$ represents hydrogen, an unbranched or branched, saturated or unsaturated, optionally at least mono-substituted $C_{1-6}$-aliphatic radical, which may comprise at least one heteroatom as a chain member, or a —(C=O)$R^{13}$-moiety, optionally in form of one of their stereoisomers, preferably enantiomers or diastereomers, their racemates or in form of a mixture of at least two of its stereoisomers, preferably enantiomers or diastereomers, in any mixing ratio, or physiologically acceptable salts thereof, or corresponding solvates, respectively.

Particularly preferred are compounds of general formula (I), wherein $R^1$, $R^2$, $R^3$, $R^4$ are each independently selected from the group consisting of H, F, Cl, Br, a saturated, branched or unbranched, optionally at least mono-substituted $C_{1-3}$-aliphatic radical, a saturated, optionally at least mono-substituted, optionally at least one heteroatom as ring member containing $C_5$- or $C_6$-cycloaliphatic radical, which may be bonded via an optionally at least mono-substituted $C_1$- or $C_2$-alkylene group, a nitro, cyano, —$OR^{12}$, —OC(=O)$R^{13}$—$SR^{14}$ and —$NR^{15}R^{16}$ moiety, preferably are each independently selected from the group consisting of H, F, Cl, Br, $CH_3$, $CH_2CH_3$, $CF_3$, $CF_2CF_3$, cyclopentyl, cyclohexyl, nitro, cyano and —$OR^{12}$ and the remaining residues $R^5$-$R^{23}$, A and B have the meaning given above, optionally in form of one of their stereoisomers, preferably enantiomers or diastereomers, their racemates or in form of a mixture of at least two of its stereoisomers, preferably enantiomers or diastereomers, in any mixing ratio, or salts, preferably physiologically acceptable salts thereof, or corresponding solvates, respectively.

Also particularly preferred are compounds of general formula (I), wherein $R^5$ represents H or a branched or unbranched $C_{1-3}$-alkyl radical, preferably H, $CH_3$ or $CH_2CH_3$, and the remaining residues $R^1$-$R^4$, $R^6$-$R^{23}$, A and B have the meaning given above, optionally in form of one of their stereoisomers, preferably enantiomers or diastereomers, their racemates or in form of a mixture of at least two of its stereoisomers, preferably enantiomers or diastereomers, in any mixing ratio, or salts, preferably physiologically acceptable salts thereof, or corresponding solvates, respectively.

Also particularly preferred are compounds of general formula (I), wherein $R^6$, $R^7$, $R^8$, $R^9$ are each independently selected from the group consisting of H, a branched or unbranched $C_{1-3}$-alkyl radical, a cyano and a $COOR^{17}$ moiety, preferably selected from the group consisting of H, $CH_3$, $CH_2CH_3$ and a cyano moiety, more preferably all represent H, and the remaining residues $R^1$-$R^5$, $R^{10}$-$R^{23}$, A and B have the meaning given above, optionally in form of one of their stereoisomers, preferably enantiomers or diastereomers, their racemates or in form of a mixture of at least two of its stereoisomers, preferably enantiomers or diastereomers, in any mixing ratio, or salts, preferably physiologically acceptable salts thereof, or corresponding solvates, respectively.

Also particularly preferred are compounds of general formula (I), wherein B represents an optionally branched, optionally at least mono-substituted $C_{1-3}$-alkyl radical, a $COOR^{19}$-moiety, or a $CH_2OR^{23}$-moiety, preferably a $COOR^{19}$-moiety, a $CH_2OR^{23}$-moiety or a $C_{1-2}$-alkyl radical, more preferably a $COOR^{19}$-moiety or a $CH_2OR^{23}$-moiety, and the remaining residues $R^1$-$R^{23}$ and A have the meaning given above, optionally in form of one of their stereoisomers, preferably enantiomers or diastereomers, their racemates or in form of a mixture of at least two of its stereoisomers, preferably enantiomers or diastereomers, in any mixing ratio, or salts, preferably physiologically acceptable salts thereof, or corresponding solvates, respectively.

Also particularly preferred are compounds of general formula (I), wherein $R^{10}$ represents hydrogen or a branched or unbranched $C_{1-4}$-alkyl radical, more preferably hydrogen, and the remaining residues $R^1$-$R^9$, $R^{11}$-$R^{23}$, A and B have the meaning given above, optionally in form of one of their stereoisomers, preferably enantiomers or diastereomers, their racemates or in form of a mixture of at least two of its stereoisomers, preferably enantiomers or diastereomers, in any mixing ratio, or salts, preferably physiologically acceptable salts thereof, or solvates, respectively.

Also particularly preferred are compounds of general formula (I), wherein $R^{11}$ is selected from the group consisting of an unsubstituted phenyl radical, a phenyl radical that is optionally at least mono-substituted with a substituent selected from the group consisting of branched or unbranched $C_{1-4}$-alkyl-radical, a branched or unbranched $C_{1-4}$-alkoxy-radical, a branched or unbranched $C_{1-4}$-perfluoroalkyl-radical, a branched or unbranched $C_{1-4}$-perfluoroalkoxy-radical, F, Cl, Br, cyclohexyl, phenyl, phenoxy, phenylthio, benzoyl, cyano, —C(=O)C$_{1-2}$-alkyl, —C(=O)OC$_{1-2}$-alkyl, -carboxy, —C(H)(OH)(phenyl), —C(H)(OH)(CH$_3$) and —NR$^A$R$^B$ wherein $R^A$, $R^B$ are each independently selected from the group consisting of H, a branched or unbranched $C_{1-4}$-alkyl-radical, —CH$_2$—CH$_2$—OH and an unsubstituted phenyl radical, an unsubstituted thiazole radical, a group of general formula (A)

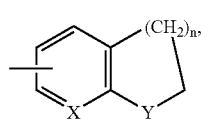

wherein
n is 1 or 2,
X represents CH or N,
Y represents CH$_2$, O, N—R$^C$, CH—OH or C(=O),
R$^C$ is H or a branched or unbranched $C_{1-4}$-alkyl radical, a group of formula (B),

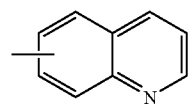

a group of formula (C),

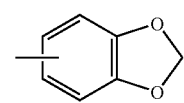

a group of general formula (D),

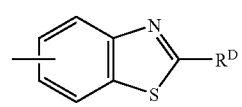

wherein R$_D$ is H or a branched or unbranched $C_{1-4}$-alkyl radical and a group of general formula (E),

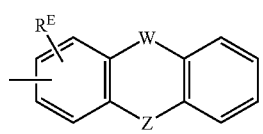

wherein
R$^E$ represents H, a branched or unbranched $C_{1-4}$-alkyl radical or a branched or unbranched $C_{1-4}$-alkoxy radical,
W represents a bond between the two aromatic rings, CH$_2$, CH—OH or C(=O),
Z represents CH$_2$, O, S, CH—OH, C(=O) or N—R$^F$ where R$^F$ represents H or a branched or unbranched $C_{1-4}$-alkyl-radical, and the remaining residues $R^1$-$R^{10}$, $R^{12}$-$R^{23}$, A and B have the meaning given above, optionally in form of one of their stereoisomers, preferably enantiomers or diastereomers, their racemates or in form of a mixture of at least two of its stereoisomers, preferably enantiomers or diastereomers, in any mixing ratio, or salts, preferably physiologically acceptable salts thereof, or corresponding solvates, respectively.

Those skilled in the art understand that the aforementioned groups (A)-(E) may be bonded via any suitable ring member of any ring, for example group (B) may also be bonded via the ring containing the nitrogen atom.

Also particularly preferred are compounds of general formula (I), wherein $R^{10}$ and $R^{11}$ together with the bridging nitrogen atom form a saturated, 6-membered heterocyclic ring, which is optionally at least mono-substituted with a methyl radical and/or condensed with an unsubstituted or at least mono-substituted phenyl- or cyclohexyl-radical, said phenyl- or cyclohexyl-radical preferably being at least mono-substituted with F and/or $OCH_3$, and the remaining residues $R^1$-$R^9$, $R^{12}$-$R^{23}$, A and B have the meaning given above, optionally in form of one of their stereoisomers, preferably enantiomers or diastereomers, their racemates or in form of a mixture of at least two of its stereoisomers, preferably enantiomers or diastereomers, in any mixing ratio, or salts, preferably physiologically acceptable salts thereof, or corresponding solvates, respectively.

Also particularly preferred are compounds of general formula (I), wherein $R^{12}$ represents H, a $C_{1-4}$-alkyl radical, a cyclohexyl radical or a phenyl radical, preferably H, $CH_3$, $C_2H_5$ or a phenyl radical, and the remaining residues $R^1$-$R^{11}$, $R^{13}$-$R^{23}$, A and B have the meaning given above, optionally in form of one of their stereoisomers, preferably enantiomers or diastereomers, their racemates or in form of a mixture of at least two of its stereoisomers, preferably enantiomers or diastereomers, in any mixing ratio, or salts, preferably physiologically acceptable salts thereof, or corresponding solvates, respectively.

Also particularly preferred are compounds of general formula (I), wherein $R^{13}$ represents H, a $C_{1-4}$-alkyl radical, cyclohexyl or a phenyl radical, preferably H, $CH_3$, $C_2H_5$ or phenyl, and the remaining residues $R^1$-$R^{12}$, $R^{14}$-$R^{23}$, A and B have the meaning given above, optionally in form of one of their stereoisomers, preferably enantiomers or diastereomers, their racemates or in form of a mixture of at least two of its stereoisomers, preferably enantiomers or diastereomers, in any mixing ratio, or salts, preferably physiologically acceptable salts thereof, or corresponding solvates, respectively.

Also particularly preferred are compounds of general formula (I), wherein $R^{14}$ represents H, a $C_{1-4}$-alkyl radical, cyclohexyl or a phenyl radical, preferably H, $CH_3$, $C_2H_5$ or phenyl, and the remaining residues $R^1$-$R^{13}$, $R^{14}$-$R^{23}$, A and B have the meaning given above, optionally in form of one of their stereoisomers, preferably enantiomers or diastereomers, their racemates or in form of a mixture of at least two of its stereoisomers, preferably enantiomers or diastereomers, in any mixing ratio, or salts, preferably physiologically acceptable salts thereof, or corresponding solvates, respectively.

Also particularly preferred are compounds of general formula (I), wherein $R^{15}$ and $R^{16}$ are each independently selected from the group consisting of H, a $C_{1-4}$-alkyl radical, cyclohexyl and a phenyl radical, preferably from the group consisting of H, $CH_3$, $C_2H_5$ and phenyl, and the remaining residues $R^1$-$R^{14}$, $R^{17}$-$R^{23}$, A and B have the meaning given above, optionally in form of one of their stereoisomers, preferably enantiomers or diastereomers, their racemates or in form of a mixture of at least two of its stereoisomers, preferably enantiomers or diastereomers, in any mixing ratio, or salts, preferably physiologically acceptable salts thereof, or corresponding solvates, respectively.

Also particularly preferred are compounds of general formula (I), wherein $R^{17}$ represents H, a $C_{1-4}$-alkyl radical, cyclohexyl or a phenyl radical, preferably H, $CH_3$, $C_2H_5$ or phenyl, and the remaining residues $R^1$-$R^{16}$, $R^{18}$-$R^{23}$, A and B have the meaning given above, optionally in form of one of their stereoisomers, preferably enantiomers or diastereomers, their racemates or in form of a mixture of at least two of its stereoisomers, preferably enantiomers or diastereomers, in any mixing ratio, or salts, preferably physiologically acceptable salts thereof, or corresponding solvates, respectively.

Also particularly preferred are compounds of general formula (I), wherein $R^{18}$ represents H, a $C_{1-4}$-alkyl radical or a phenyl radical, preferably H, $CH_3$ or phenyl, and the remaining residues $R^1$-$R^{17}$, $R^{19}$-$R^{23}$, A and B have the meaning given above, optionally in form of one of their stereoisomers, preferably enantiomers or diastereomers, their racemates or in form of a mixture of at least two of its stereoisomers, preferably enantiomers or diastereomers, in any mixing ratio, or salts, preferably physiologically acceptable salts thereof, or corresponding solvates, respectively.

Also particularly preferred are compounds of general formula (I), wherein $R^{19}$ represents H or an unbranched or branched $C_{1-4}$ alkyl radical, preferably H or a $C_{1-2}$ alkyl radical and the remaining residues $R^1$-$R^{18}$, $R^{20}$-$R^{23}$, A and B have the meaning given above, optionally in form of one of their stereoisomers, preferably enantiomers or diastereomers, their racemates or in form of a mixture of at least two of its stereoisomers, preferably enantiomers or diastereomers, in any mixing ratio, or salts, preferably physiologically acceptable salts thereof, or corresponding solvates, respectively.

Also particularly preferred are compounds of general formula (I), wherein $R^{20}$ represents H, an unbranched or branched $C_{1-4}$ alkyl radical or a $NR^{21}R^{22}$-moiety, preferably H, a $C_{1-2}$ alkyl radical or a $NR^{21}R^{22}$-moiety and the remaining residues $R^1$-$R^{19}$, $R^{21}$-$R^{23}$, A and B have the meaning given above, optionally in form of one of their stereoisomers, preferably enantiomers or diastereomers, their racemates or in form of a mixture of at least two of its stereoisomers, preferably enantiomers or diastereomers, in any mixing ratio, or salts, preferably physiologically acceptable salts thereof, or corresponding solvates, respectively.

Also particularly preferred are compounds of general formula (I), wherein $R^{21}$ represents H or an unbranched or branched $C_{1-4}$ alkyl radical, preferably H or a $C_{1-2}$ alkyl radical and the remaining residues $R^1$-$R^{20}$, $R^{22}$, $R^{23}$, A and B have the meaning given above, optionally in form of one of their stereoisomers, preferably enantiomers or diastereomers, their racemates or in form of a mixture of at least two of its stereoisomers, preferably enantiomers or diastereomers, in any mixing ratio, or salts, preferably physiologically acceptable salts thereof, or corresponding solvates, respectively.

Also particularly preferred are compounds of general formula (I), wherein $R^{22}$ represents H or an unbranched or branched $C_{1-4}$ alkyl radical, preferably H or a $C_{1-2}$ alkyl radical and the remaining residues $R^1$-$R^{21}$, $R^{23}$ A and B have the meaning given above, optionally in form of one of their stereoisomers, preferably enantiomers or diastereomers, their racemates or in form of a mixture of at least two of its stereoisomers, preferably enantiomers or diastereomers, in any mixing ratio, or salts, preferably physiologically acceptable salts thereof, or corresponding solvates, respectively.

Also particularly preferred are compounds of general formula (I), wherein $R^{23}$ represents H or an unbranched or branched $C_{1-4}$ alkyl radical, preferably H or a $C_{1-2}$ alkyl radical and the remaining residues $R^1$-$R^{22}$, A and B have the meaning given above, optionally in form of one of their stereoisomers, preferably enantiomers or diastereomers, their racemates or in form of a mixture of at least two of its stereoisomers, preferably enantiomers or diastereomers, in any mixing ratio, or salts, preferably physiologically acceptable salts thereof, or corresponding solvates, respectively.

Also particularly preferred are compounds of general formula (I), wherein A represents a —$CH_2$-group and the remaining residues $R^1$-$R^{23}$ and B have the meaning given above, optionally in form of one of their stereoisomers, preferably enantiomers or diastereomers, their racemates or in form of a mixture of at least two of its stereoisomers, preferably enantiomers or diastereomers, in any mixing ratio, or salts, preferably physiologically acceptable salts thereof, or corresponding solvates, respectively.

Also particularly preferred are 1,4-disubstituted piperidine compounds of general formula (I) given above, wherein $R^1$, $R^2$, $R^3$, $R^4$ are each independently selected from the group consisting of H, F, Cl, Br, OH, $CH_3$ and $OCH_3$, $R^5$ represents hydrogen, $R^6$, $R^7$, $R^8$, $R^9$ all represent H, A represents —$CH_2$—, B represents a —$CH_2$—OH or —(C=O)—O—$CH_3$ group, $R^{10}$ represents hydrogen, $R^{11}$ is selected from the group consisting of unsubstituted phenyl, phenyl that is optionally at least mono-substituted with one or more substituents independently selected from the group consisting cyclohexyl, phenyl, phenoxy, benzoyl, —C(=O)—$C_{1-2}$-alkyl, —C(H)(OH)(phenyl) and —C(H)(OH)($CH_3$), a group of general formula (A)

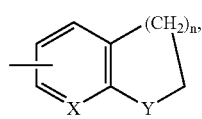

(A)

wherein n is 1 or 2,

X represents CH,

Y represents CH—OH or C(=O), a group of formula (B),

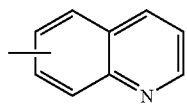

(B)

a group of formula (C),

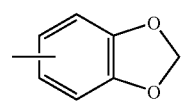

(C)

and a group of general formula (E),

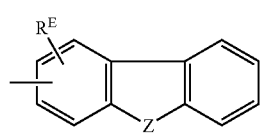

(E)

wherein $R^E$ represents H, a branched or unbranched $C_{1-4}$-alkyl radical or a branched or unbranched $C_{1-4}$-alkoxy radical, Z represents $CH_2$, O, S, CH—OH, C(=O) or N—$R^F$ where $R^F$ represents H or an alkyl-radical selected from the group consisting of methyl, ethyl, n-propyl, iso-propyl, n-butyl, iso-butyl, sec-butyl and tert.-butyl, optionally in form of one of its stereoisomers, preferably enantiomers or diastereomers, its racemate or in form of a mixture of at least two of its stereoisomers, preferably enantiomers or diastereomers, in any mixing ratio, or a salt, preferably a physiologically acceptable salt thereof, or a corresponding solvate, respectively.

Most preferred are 1,4-disubstituted piperidine compounds of general formula (I) selected from the list B of the examples section given below.

Most preferred are also the following 1,4-disubstituted piperidine compounds of general formula (I):

[1] N-(9-Ethyl-9H-carbazol-3-yl)-2-[4-(2-hydroxymethyl-6-methyl-phenylamino)-piperidine-yl]acetamide;

[2] 2-[4-(2-Hydroxymethyl-4-methyl-phenylamino)-piperidine-1-yl]-N-(9-oxo-9H-fluoren-3-yl)-acetamide;

[3] 2-[4-(2-Hydroxymethyl-6-methyl-phenylamino)-piperidine-1-yl-]-N-(9-oxo-9H-fluoren-3-yl)-acetamide;

[4] N-(9-Hydroxy-9H-fluoren-3-yl)-2-[4-(2-hydroxymethyl-4-methyl-phenylamino)-piperidine-1-yl]-acetamide;

[5] N-(9-Hydroxy-9H-fluoren-3-yl)-2-[4-(2-hydroxymethyl-6-methyl-phenylamino)-piperidine-1yl]-acetamide;

[6] 2-{1-[(9-Oxo-9H-fluoren-3ylcarbamoyl)-methyl]-piperidin-4-ylamino}benzoic acid methyl ester and

[7] 2-[4-(2-Hydroxymethyl-4-methyl-phenylamino)-piperidin-1-yl]-N-phenyl-acetamide,

[8] 2-[4-(2-Hydroxymethyl-phenylamino)-piperidin-1-yl]-N-(1-oxo-indan-5-yl)-acetamide, optionally in form of a salt, preferably a physiologically acceptable salt, particularly preferably in form of a physiologically acceptable acid addition salt, most preferably a hydrochloride salt, or a corresponding solvate.

In a further aspect the present invention also provides a process for the preparation of 1,4-disubstituted piperidine compounds of general formula (I), wherein $R^1$-$R^{23}$, A and B have the meaning given above, according to which at least one compound of general formula (II),

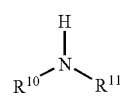

(II)

wherein $R^{10}$ and $R^{11}$ have the meaning given above, is reacted with at least one compound of general formula (III),

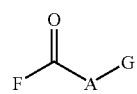

(III)

wherein A has the meaning given above, F represents halogen, hydroxy or an O-acyl group and G represents halogen, preferably chlorine, in a suitable reaction medium and preferably in the presence of at least one base and/or optionally at least one auxiliary agent, and reacting the so obtained compound of general (IV)

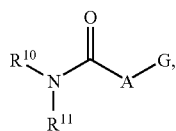

wherein A, G, $R^{10}$ and $R^{11}$ have the above defined meaning, is reacted with at least one piperidine compound of general formula (V) and/or a salt, preferably hydrochloride salt, thereof,

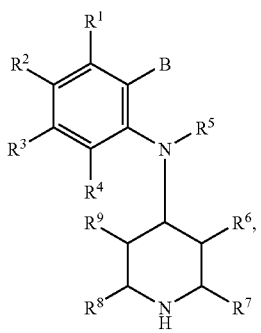

wherein $R^1$ to $R^9$ and B have the meaning as defined above, in a suitable reaction medium, optionally in the presence of at least one base and/or at least one auxiliary agent to yield a compound of general formula I.

According to the invention, the process may be illustrated as an example by the following reaction scheme A:

Scheme A:

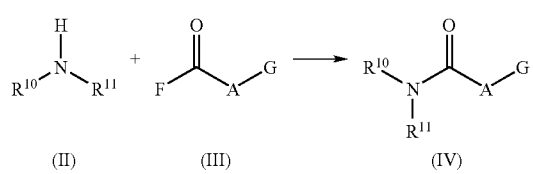

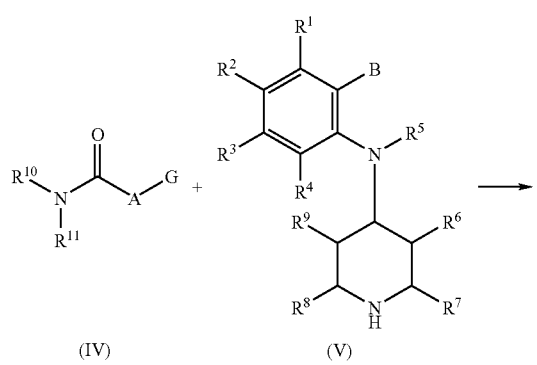

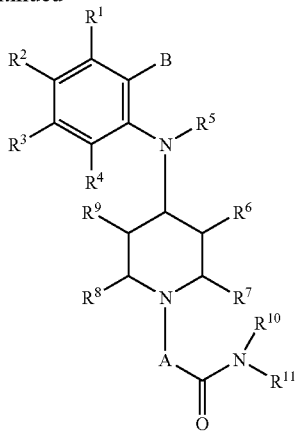

wherein $R^1$ to $R^{11}$, A and B have the meaning as given above.

In yet a further aspect the present invention also provides a process for the preparation of 1,4 disubstituted piperidine compounds of general formula (I), wherein $R^1$-$R^{23}$ and A have the meaning given above and B represents a substituted aliphatic radical or a —$CH_2OR^{23}$-moiety, according to which at least one compound of general formula (II),

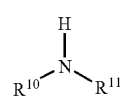

wherein $R^{10}$ and $R^{11}$ have the meaning given above, is reacted with at least one compound of general formula (III),

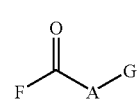

wherein A has the meaning given above, F represents halogen, hydroxy or an O-acyl group and G represents halogen, preferably chlorine, in a suitable reaction medium and preferably in the presence of at least one base and/or at least one auxiliary agent, and reacting the so obtained compound of general (IV)

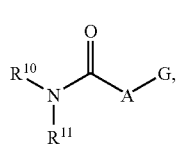

wherein A, G, $R^{10}$ and $R^{11}$ have the above defined meaning, with at least one piperidin compound of general formula (V) and/or a salt, preferably hydrochloride, thereof, (V)

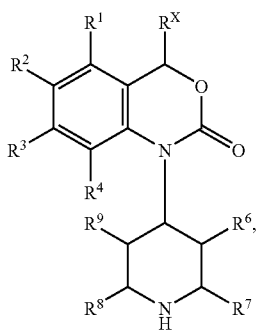

wherein $R^1$ to $R^9$ have the meaning as defined above and $R^x$ represents any substituent including hydrogen, preferably hydrogen, in a suitable reaction medium, optionally in the presence of at least one base and/or at least one auxiliary agent, to yield a compound of general formula (VI), (VI)

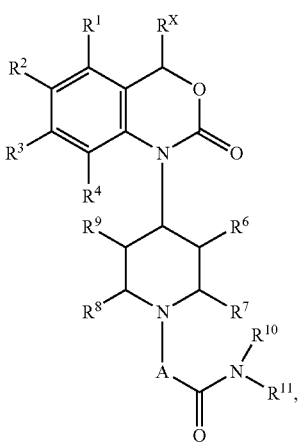

which is reacted with a base, preferably in a suitable reaction medium, more preferably in a mixture of water and ethanol, to yield a compound of general formula (I), wherein $R^1$-$R^4$ and $R^6$-$R^{23}$ and A have the meaning as defined above, $R^5$ represents H and B represents a substituted aliphatic radical or a —$CH_2OR^{23}$-moiety.

According to the invention, said process may be illustrated as an example by the following reaction scheme B:

Scheme B:

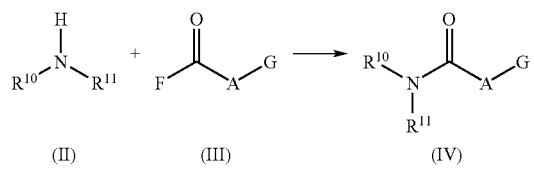

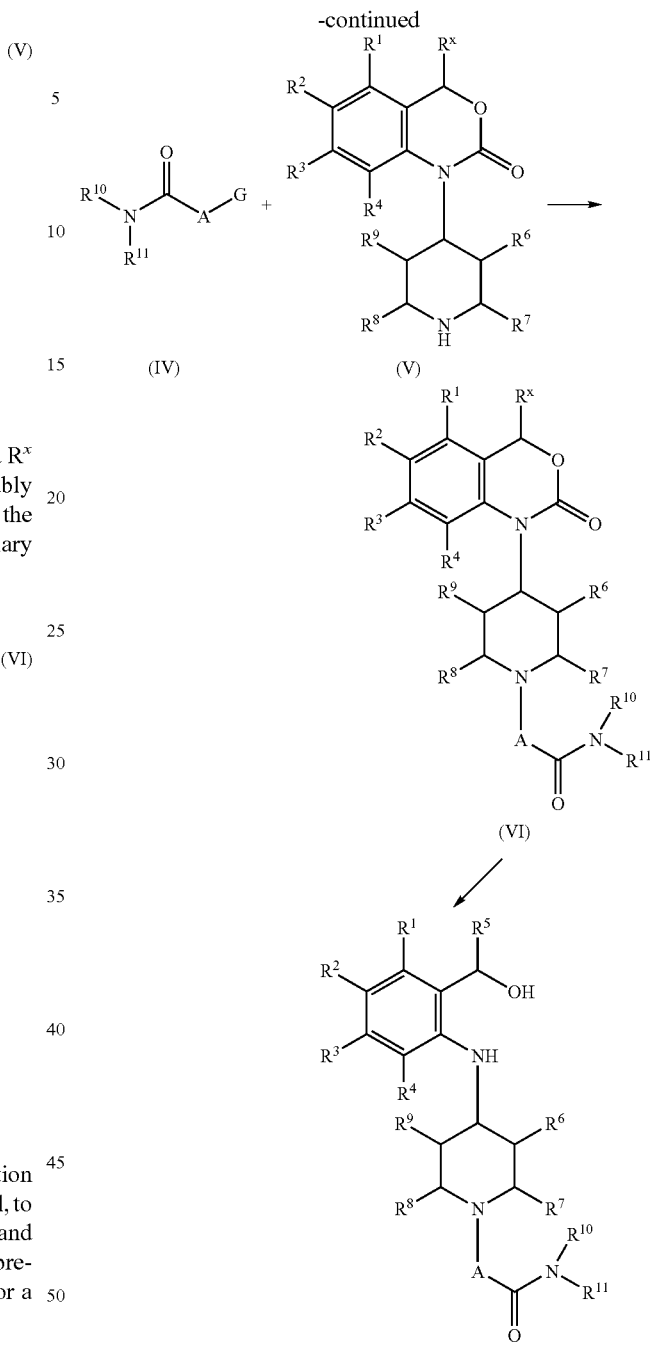

Suitable reaction media are e.g. organic solvents, such as ethers, preferably diethyl ether, dioxane, tetrahydrofurane, dimethyl glycol ether, or alcohols, e.g. methanol, ethanol, propanol, isopropanol, butanol, isobutanol, tert-butanol, or hydrocarbons, preferably benzene, toluene, xylene, hexane, cyclohexane, petroleum ether, or halogenated hydrocarbons, e.g. dichloromethane, trichloromethane, tetrachloromethane, dichloroethylene, trichloroethylene, chlorobenzene or/and other solvents, preferably ethyl acetate, triethylamine, pyridine, dimethylsulfoxide, diemthylformamide, hexamethylphosphoramide, acetonitril, acetone or nitromethane, are included. Mixtures based one or more of the aforementioned solvents may also be used.

Bases that may be used in the processes according to the present invention are generally organic or inorganic bases, preferably alkali metal hydroxides, e.g. sodium hydroxyde or potassium hydroxyde, or obtained from other metals such as barium hydroxide or different carbonates, preferably potassium carbonate, sodium carbonate, calcium carbonate, or alkoxides, e.g. sodium methoxide, potassium methoxide, sodium ethoxide, potassium methoxide, potassium ethoxide or potassium tert-butoxide, or organic amines, preferably triethylamine, diisopropyethylamine or heterocycles, e.g. 1,4-diazabicyclo[2.2.2]octane, 1,8-diazabicyclo[5.4.0]undec-7-ene pyridine, diamino pyridine, dimethylaminopyridine, methylpiperidine or morpholine. Alkali metals such as sodium or ist hydrides, e.g. sodium hydride, may also be used. Mixtures based one or more of the aforementioned bases may also be used.

The above mentioned bases may be used for the process as auxiliary agents, when appropriate. Other suitable auxiliary agents for the above mentioned reactions are, for example, dehydrating agents like carbodiimides, e.g. diisopropylcarbodiimide, cyclohexylcarbodiimide or N-(3-dimethylaminopropyl)-N'-ethylcarbodiimide hydrochloride, or carbonylic compounds, e.g. carbonyldiimidazol or compounds like isobutylchloroformiate or methansulfonyl chloride, among others. These reagents are generally used in amounts from 0.5 to 5 mol versus 1 mol of the corresponding reactands. These bases are generally used in amounts from 0.05 to 10 mol versus 1 mol of the corresponding reactands.

During some of the synthetic reactions described or while preparing the compounds of general formulas (I), (II), (III), (IV), (V) and (VI), the protection of sensitive groups or of reagents may be necessary and/or desirable. This can be performed by using conventional protective groups like those described in the literature. The protective groups may also be eliminated as convenient by means well-known to those skilled in the art.

The compounds of general formulas (II), (III), (IV) and (V) are either commercially available or can be produced according to methods known to those skilled in the art. The reaction of compounds of general formulas (IV) and (V) to yield 1,4-disubstituted piperidine compounds of general formula (I) may also be facilitated by conventional methods known to those skilled in the art.

The compounds of general formula (IV) are commercially available or may be produced according to scheme I by conventional methods known to those skilled in the art. Essentially the respective compound of general formula (II) is reacted with chloroacetyl chloride or the respective compound of general formula (III) in the presence of an organic reaction medium, preferably dichloromethane and a base, preferably triethylamine and/or diisopropylethylamine.

The preparation of compounds of general formula (V) and their use for the preparation of compounds of general formula (I) is illustrated in schemes 1 and 2 given below:

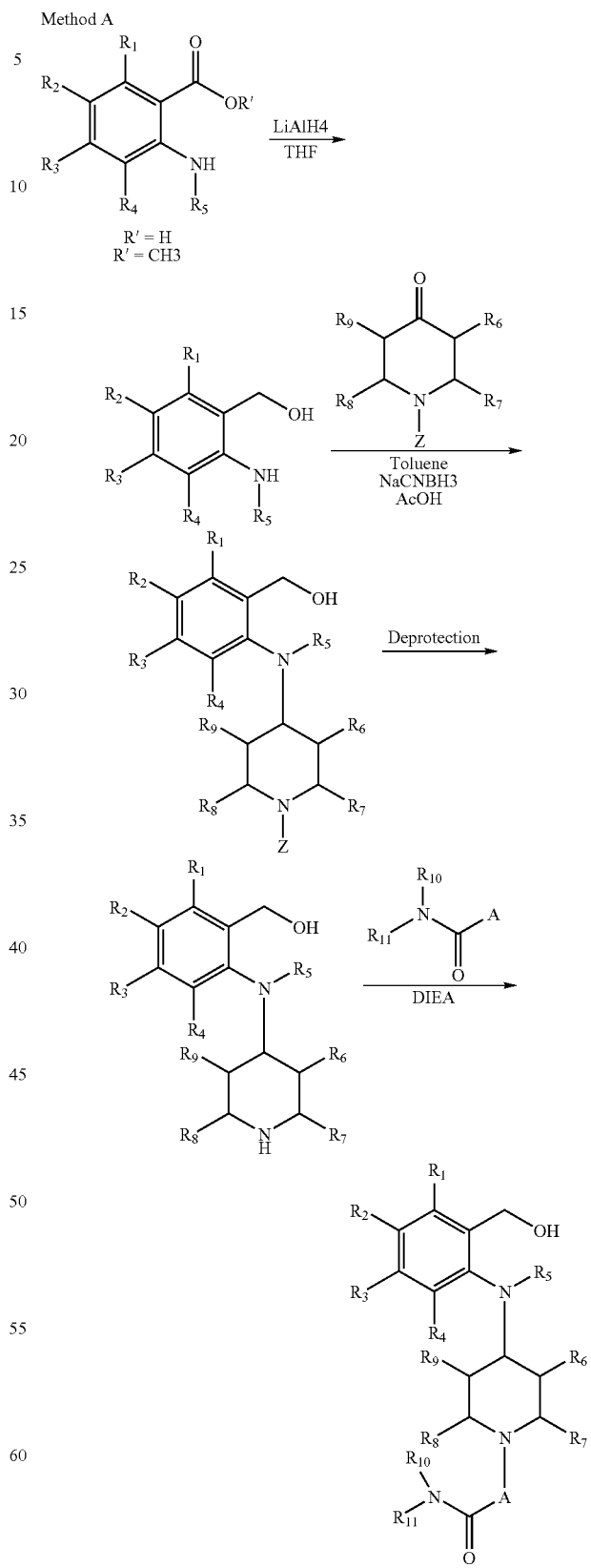

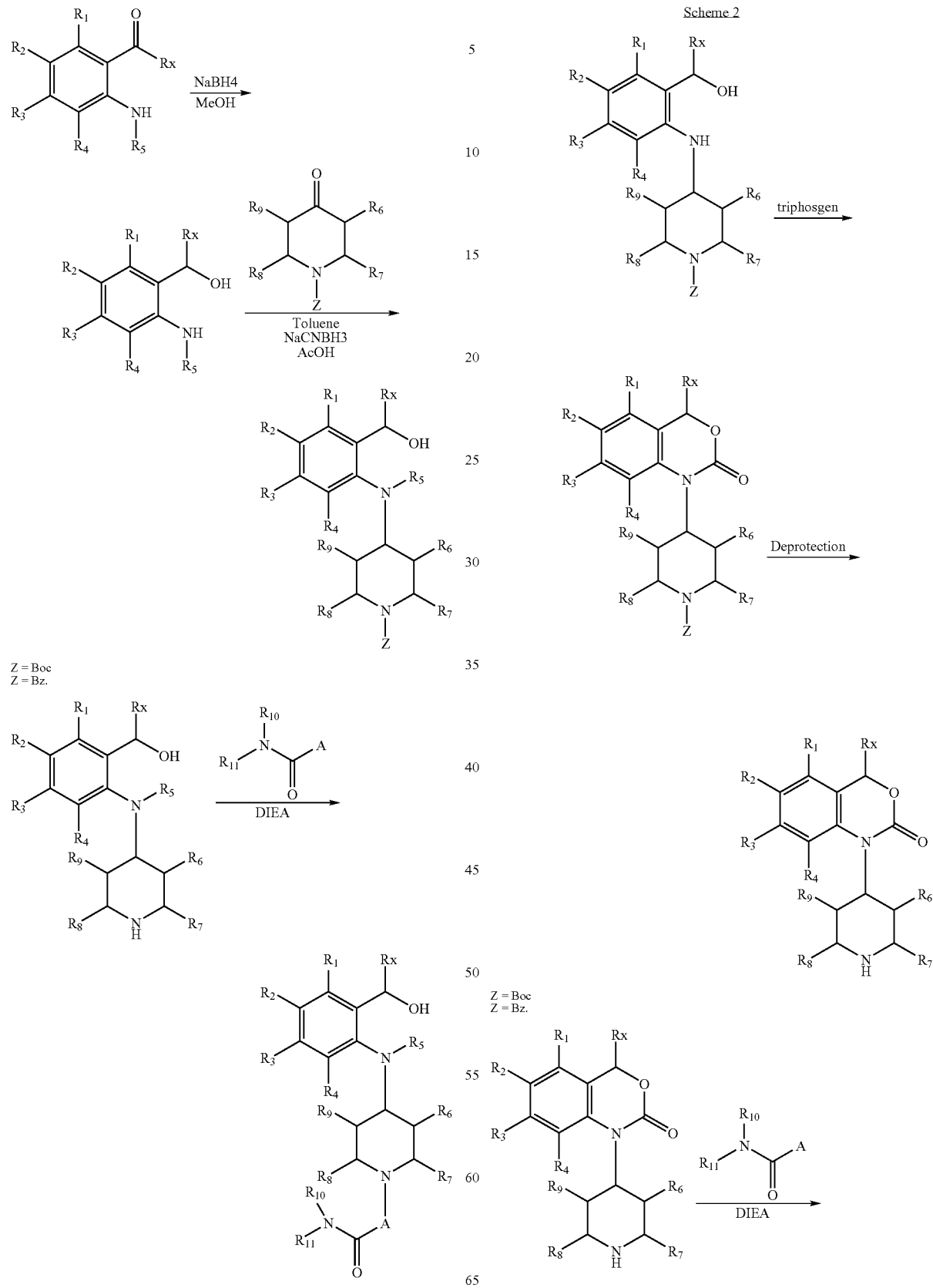

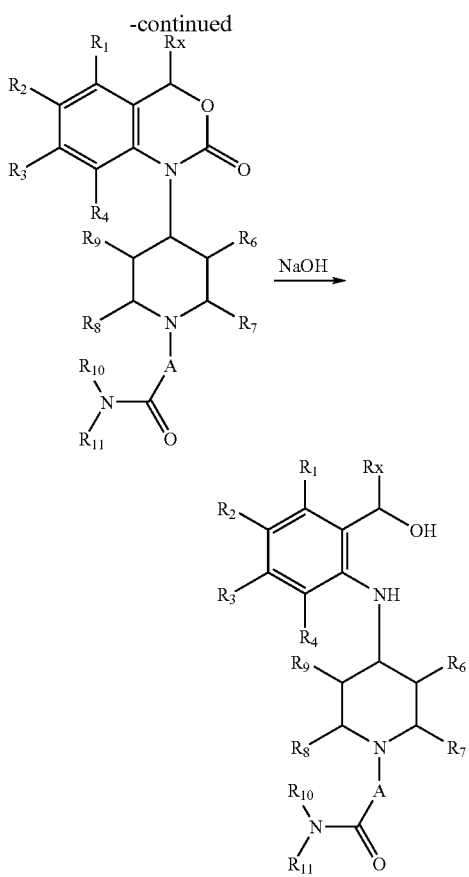

In a further aspect the present invention also provides a process for the preparation of salts of 1,4-disubstituted piperidine compounds of general formula (I), wherein at least one compound of general formula (I) having at least one basic group is reacted with an inorganic and/or organic acid, preferably in the presence of a suitable reaction medium. Suitable reaction media are the ones given above. Suitable inorganic acids are for example hydrochloric acid, hydrobromic acid, phosphoric acid, sulfuric acid, nitric acid, suitable organic acids are e.g. citric acid, maleic acid, fumaric acid, tartaric acid, or derivatives thereof, such as p-toluenesulfonic acid, methanesulfonic acid or camphersulfonic acid.

In yet a further aspect the present invention also provides a process for the preparation of salts of 1,4-disubstituted piperidine compounds of general formula (I), wherein at least one compound of general formula (I) having at least one acidic group is reacted with one or more suitable bases, preferably in the presence of a suitable reaction medium. Suitable bases are e.g. hydroxides, carbonates or alkoxides, which include suitable cations, derived e.g. from alkaline metals, alkaline earth metals or organic cations, e.g. $[NH_nR_{4-n}]^+$, wherein n is 0, 1, 2, 3 or 4 and R represents a branched or unbranched $C_{1-4}$-alkyl-radical.

Solvates, preferably hydrates, of the 1,4-disubstituted piperidine compounds of general formula (I), or corresponding stereoisomers, or corresponding salts may also be obtained by standard procedures known to those skilled in the art.

If the 1,4-disubstituted piperidine compounds of general formula (I) are obtained in form of a mixture of stereoisomers, particularly enantiomers or diastereomers, said mixtures may be separated by standard procedures known to those skilled in the art, e.g. chromatographic methods or crystallization with chiral reagents.

The purification and isolation of the 1,4-disubstituted piperidine compounds of general formula (I) or a corresponding stereoisomer, or a corresponding salt, or corresponding solvate respectively, if required, may be carried out by conventional methods known to those skilled in the art, e.g. chromatographic methods or recrystallization.

The 1,4-disubstituted piperidine compounds of general formula (I), their stereoisomers or the respective salts or solvates are toxicologically acceptable and are therefore suitable as pharmaceutical active substances for the preparation of medicaments.

The present invention therefore also provides for a medicament comprising at least one 1,4-disubstituted piperidine compound of general formula (I), optionally in form of one of its stereoisomers, preferably enantiomers or diastereomers, its racemate or in form of a mixture of at least two of its stereoisomers, preferably enantiomers or diastereomers, in any mixing ratio, or a physiologically acceptable salt thereof, or a solvate, respectively, and optionally one or more pharmaceutically acceptable adjuvants.

Furthermore, the present invention also provides for a pharmaceutical composition comprising at least one 1,4-disubstituted piperidine compound of general formula (I), optionally in form of one of its stereoisomers, preferably enantiomers or diastereomers, its racemate or in form of a mixture of at least two of its stereoisomers in any mixing ratio, or a physiologically acceptable salt thereof, or a solvate, respectively, and optionally one or more pharmaceutically acceptable adjuvants, which is not yet formulated into a medicament.

Preferably the medicament is suitable for the regulation of neuropeptide Y receptors, preferably of neuropeptide Y 5 (NPY5) receptor, for improvement of cognition, regulation of appetite, regulation of body weight, for the regulation of food ingestion (food intake), preferably for the prophylaxis and/or treatment of disorders of food ingestion, preferably obesity, anorexia, bulimia, cachexia or type II diabetes (non insulin dependent diabetes), for the prophylaxis and/or treatment of disorders of the peripheral nervous system, disorders of the central nervous system, diabetes, arthritis, epilepsy, anxiety, depression, cognitive disorders, preferably memory disorders, cardiovascular diseases, pain, hypertensive syndrome, inflammatory diseases or immune diseases.

The present invention also provides for the use of at least one 1,4-disubstituted piperidine compound of general formula (I), optionally in form of one of its stereoisomers, preferably enantiomers or diastereomers, its racemate or in form of a mixture of at least two of its stereoisomers, preferably enantiomers or diastereomers, in any mixing ratio, or a physiologically acceptable salt thereof, or a solvate, respectively, for the manufacture of a medicament for the regulation of neuropeptide Y receptors, preferably of neuropeptide Y 5 (NPY5) receptor, for improvement of cognition, for regulation of appetite, regulation of body weight, for the regulation of food ingestion (food intake), preferably for the prophylaxis and/or treatment of disorders of food ingestion, preferably obesity, anorexia, bulimia, cachexia or type II diabetes (non insulin dependent diabetes), for the prophylaxis and/or treatment of disorders of the peripheral nervous system, disorders of the central nervous system, diabetes, arthritis, epilepsy, anxiety, depression, cognitive disorders, preferably memory disorders, cardiovascular diseases, pain, hypertensive syndrome, inflammatory diseases or immune diseases.

The medicament may be in any form suitable for the application to humans and/or animals, preferably mammals, and can be produced by standard procedures known to those skilled in the art. The composition of the medicament may vary depending on the route of administration.

The medicament of the present invention may e.g. be administered parentally in combination with conventional injectable liquid carriers, such as water or suitable alcohols. Conventional pharmaceutical adjuvants for injection, such as stabilizing agents, solubilizing agents, and buffers, may be included in such injectable compositions. These medicaments may preferably be injected intramuscularly, intraperitoneally, or intravenously.

Medicaments according to the present invention may also be formulated into orally administrable compositions containing one or more physiologically compatible carriers or excipients, in solid or liquid form. These compositions may contain conventional ingredients such as binding agents, fillers, lubricants, and acceptable wetting agents. The compositions may take any convenient form, such as tablets, pellets, capsules, lozenges, multiparticulates such as granules or pellets, optionally compressed into a tablet or filled into a capsule, aqueous or oily solutions, suspensions, emulsions, or dry powdered form suitable for reconstitution with water or other suitable liquid medium before use, for immediate or controlled release.

The liquid oral forms for administration may also contain certain additives such as sweeteners, flavoring, preservatives, and emulsifying agents. Non-aqueous liquid compositions for oral administration may also be formulated, containing e.g. edible oils. Such liquid compositions may be conveniently encapsulated in e.g., gelatin capsules in a unit dosage amount.

The compositions of the present invention may also be administered topically or via a suppository.

The above mentioned compositions include preferably 1 to 60% by weight of one or more of the 1,4-disubstituted piperidine compound of general formula (I), optionally in form of one of its stereoisomers, preferably enantiomers or diastereomers, its racemate or in form of a mixture of at least two of its stereoisomers in any mixing ratio, or a physiologically acceptable salt thereof, or a solvate, respectively, and 40 to 99% by weight of the appropriate pharmaceutical vehicle(s).

The daily dosage for humans and animals may vary depending on factors that have their basis in the respective species or other factors, such as age, weight or degree of illness and so forth. The daily dosage for mammals including humans usually ranges from 1 milligram to 2000 milligram, preferably 1 to 1500 mg, more preferably 1 to 1000 mg of substance to be administered during one or several intakes.

Pharmacological Methods:

Neuropeptide $Y_5$ Receptor Binding Studies:

The methods used for membrane preparation and binding are similar to those described by Y. Hu, B. T. Bloomquist et al. in Y. Hu, B. T. Bloomquist et al., The Journal of Biological Chemistry, 1996, 271, 26315-26319 with modifications. Said literature description is herewith incorporated by reference and forms part of the disclosure. Cells C6 were transfected with the rat Y5 receptor. The cells were grown under standard culture conditions in 150 cm$^2$ dishes and they were harvested using a rubber scraper and 10 ml PBS. The cells from five dishes were collected and centrifuged 2.500 g for 5 min (4° C.). The pellet was washed by resuspending in 3 ml buffer (Tris-HCl 10 mM, pH 7.4), homogenized using a Potter S homogenizer, 10 strokes at 600 rpm and centrifuged 48.000 g for 20 min (4° C.). The pellet was resuspended in 8 ml membrane buffer (Tris-HCl 25 mM, NaCl 120 mM, KCl 5 mM, $KH_2PO_4$ 1.2 mM, $CaCl_2$ 2.5 mM, $MgSO_4$ 1.2 mM, BSA 0.15 mg/ml, Bacitracine 0.5 mg/ml, pH 7.4) and rehomogenized using the Potter S, 10 strokes at 600 rpm. The protein concentration in the incubation was 40 µ/ml. The radioligand was [$^{125}$I]-PYY (100 pM) in a total incubation volume of 200 µl. Following incubation at 25° C. for 2 h, the reaction was stopped by addition of 5 ml ice-cold buffer (Tris-HCl 25 mM, NaCl 120 mM, KCl 5 mM, $KH_2PO_4$ 1.2 mM, $CaCl_2$ 2.5 mM, $MgSO_4$ 1.2 mM, pH 7.4) and rapid filtration in a Harvester Brandell Cell using filters (Schleicher & Schuell GF 3362) pretreated for two hours with 0.5% polyethyleneimine. Filters were washed one time with 5 ml ice-cold buffer. The filters were placed into plastic scintillation vials and 5 ml scintillation cocktail Ecoscint H were added. The quantity of radioactivity present was determined in a Wallac Winspectral 1414 counter. Non specific binding was determined in the presence of 1 µM de pNPY. All binding assays were done in triplicate.

Binding to Neuropeptide $Y_2$

The experimental protocol follows the method by Y. Dumont et al. as described in Y. Dumont, A. Fournier, S. St-Pierre, R. Quirion: Characterization of Neuropeptide Y Binding Sites in Rat Brain Preparations Using [$^{125}$I][Leu$^{31}$, Pro$^{34}$]Peptide YY and [$^{125}$I]Peptide YY$_{3-36}$ as Selective Y1 and Y2 Radioligands, The Journal of Pharmacology and Experimental Therapeutics, 1995, 272, 673-680, with slight modifications. Said literature description is herewith incorporated by reference and forms part of the disclosure.

Male Wistar rats are sacrificed by decapitation, their brains are rapidly removed and the hypoccampus is dissected. Homogenization is performed in cold conditions in the buffer: 120 mM NaCl, 4.7 mM KCl, 2.2 mM $CaCl_2$, 1.2 mM $KH_2PO_4$, 1.2 mM $MgSO_4$, 25 mM $NaHCO_3$, 5.5 mM glucose, pH 7.4, by means of a Ultra-Turrax homogenizer for 15 seconds at 13,500 rpm. The ratio between fresh tissue weight and buffer volume is of ten times. The membrane is centrifuged for 10 min at 48,000 g. The supernatant is discarded and the pellet is washed, resuspended and recentrifuged two more times. The final membrane resuspension is performed in the buffer: 120 mM NaCl, 4.7 mM KCl, 2.2 mM $CaCl_2$, 1.2 mM $KH_2PO_4$, 1.2 mM $MgSO_4$, 25 mM $NaHCO_3$, 5.5 mM glucose, 0.1% BSA, 0.05% bacitracin, pH 7.4, at a 90 ml/g ratio of fresh issue. The radioligand used is [$^{125}$I]-PYY$_{3-36}$ at the concentration of 28 pM. Incubation volume: 500 µl. Incubation is performed at 25° C. for 150 minutes and ended by rapid filtration in a Harvester Brandel Cell through fiber glass filters of the brand Schleicher & Schuell GF 3362 pretreated with a 0.5% polyethylenimine solution. The filters are cold-washed three times with three milliliters of the same buffer used in homogenization. The filters are transferred to vials and 5 ml of Ecoscint H liquid scintillation cocktail are added to each vial. The vials are allowed to reach steady state for a few hours before counting in a Wallac Winspectral 1414 scintillation counter. Non-specific binding is determined in the presence of 1 µM of pNPY (Neuropeptide Y of porcine origin). The assays are performed in triplicate.

Behavioural Models (Food Intake Measurements)

In both test, animals rats (Male W, 200-270 g, obtained from Harlan, S. A) were used. The rats are acclimatized to the animal facility for at least 5 days before being subjected to any experimental procedure. During this period, animals were housed in groups of five in translucid cages and provided with food and water ad libitum. At least 24 hours before the tests, animals are adapted to single-housing conditions.

Nocturnal Feeding:

Food intake is measured in home cages in order to minimize non-specific stress effects on food intake resulting from changes in housing conditions. Food and water is available ad libitum. Immediately before lights turn off, rats are weighed, randomized and dosed (orally or intraperitoneally), either with vehicle or selected 1,4-disubstituted piperidine compounds of general formula (I). Thereafter, rats are returned to home cages and food left on top covers is measured. Remaining food and animal's weight is measured next morning.

The above mentioned methods are described in Ants Kask et al., European Journal of Pharmacology 414 (2001) 215-224 and Turnbull et al., Diabetes, Vol. 51, August 2002, which are hereby incorporated by reference and form part of the disclosure.

Acute Effects of Selected Compounds on Food Intake in Fasted Rats:

Rats were fasted for 23 hours in home cages, and after this period dosed (orally or intraperitoneally), either with vehicle or 1,4-disubstituted piperidine compound of general formula (I). One hour later preweighed food is left on top covers, and cumulative food intake is measured after 1, 2, 4 and 6 hours.

The methods are described in Ants Kask et al., European Journal of Pharmacology 414 (2001) 215-224 and Turnbull et al., Diabetes, Vol. 51, August 2002, which are hereby incorporated by reference and form part of the disclosure.

The following examples are given to illustrate the present invention, but they do not limit the scope of the present invention.

EXAMPLES

General Method for Obtaining Haloamides Derivatives of the General Formula (IV)

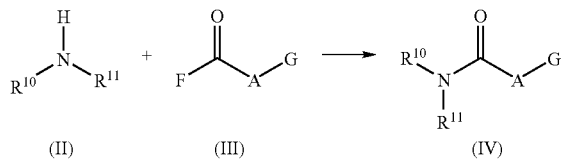

The haloamides used for obtaining the compounds of the present invention are either commercially available or have been prepared according to the scheme 2, employing conventional methods. Essentially the corresponding amines are reacted with chloroacetyl chloride or with a derivative of the general formula (IIIa), the reaction is carried out using an organic solvent, usually dichloromethane, and a base, usually triethylamine.

Example A

2-Chloro-N-(9-oxo-9H-fluoren-3-yl)-acetamide

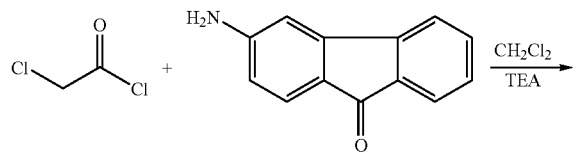

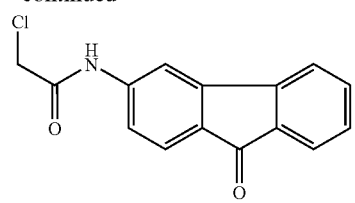

A solution of 3-amino-9-fluorenone (1.95 g, 10 mmols), triethylamine (2.07 ml, 15 mmols), in 25 ml of dried dichloromethane, is cooled to 10° C. and a solution of chloroacetyl chloride (1.18 g, 10.5 mmoles) in 10 ml of dried dichloromethane is then added drop by drop. The resulting mixture is kept stirring for 1 hour at room temperature overnight. The mixture is washed with 2×30 ml of water, dried over sodium sulfate and evaporated. 2.63 g 2-Chloro-N-(9-oxo-9H-fluoren-3-yl)-acetamide (97%) are obtained.

$^1$H RMN (d$_6$-DMSO): 10.7 (s, 1H), 7.98 (s, 1H), 7.66 (d, 1H), 7.57 (m, 3H), 7.50 (d, 1H), 7.37 (t, 1H), 4.32 (s, 2H)

Example 6a

2-{1-[(9-Oxo-9H-fluoren-3-yl-carbamoyl)-methyl]-piperidin-4-yl-amino}benzoic acid methyl ester chlorohydrate

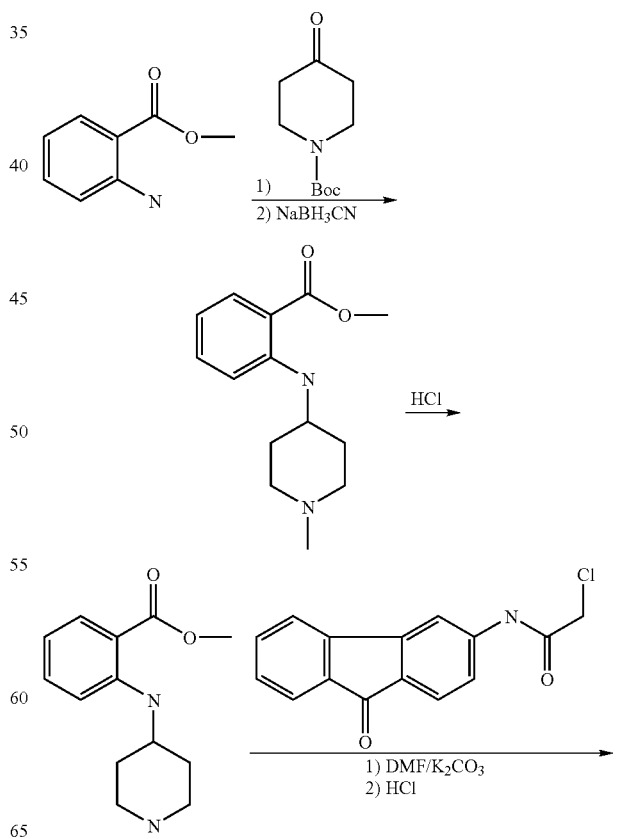

-continued

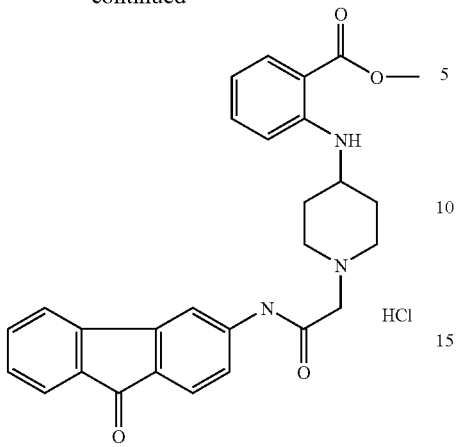

a) 4-(2-metoxycarbonyl-phenylamino)-piperidine-1-tert-butylcarboxylate

A solution of 1-(tert-butyloxycarbonyl)-4-piperidinone (2 g, 0.01 mol), methyl anthranylate (1.66 g, 0.011 mol) y acetic acid (1.4 ml, 0.022 mol) in dried toluene (50 mL) were heated to reflux, removing the water by means of azeotropic distillation with a Dean-Stark, over 30 hours. Then, the mixture was cooled and concentrated under vacuum to the half of the volume. $NaBH_3CN$ (2 g, 0.032 mol) and dried THF (30 mL) is added to a resulting solution.

Afterwards, acetic acid (1 mL, 0.017 mol) was added drop by drop over one hour (1 mL, 0.017 mol). The reaction mixture was stirred at room temperature over 24 hours. The mixture was concentrated under vacuum and the residue was dissolved in ethyl acetate (75 mL), washed with a saturated $NaHCO_3$ (4×25 mL) and a saturated NaCl solution (25 mL), dried and evaporated to dryness. This raw material was used in the following step.

b) 2-(Piperidine-4-yl-amino)-methyl benzoate

A solution of 3.2 g of the raw material obtained in the previous step in 40 mL of dried ethyl acetate, was cooled to 0° C. Then a 5 M hydrogen chloride solution in ethyl ether (40 mL) was added and the resulting mixture was kept at 0° C. over 4 hours. The solvent was evaporated and the residue was suspended in water and was alcalinized with sodium hydroxyde, and was extracted with chloroform (3×20 mL), the combined organic extracts were washed with water, dried over sodium sulfate and evaporated. The raw material was purified via column cromatography by eluting with chloroform:methanol 9:1 (vol/vol). In this way 1.45 g of a yellow solid is obtained.

IR (cm$^{-1}$) KBr.: 3349, 3232, 2941, 2812, 1686, 1578, 1518, 1436, 1253, 1162, 1079, 742.

M.P.: 113-115° C.

c) 2-{1-[(9-Oxo-9H-fluoren-3-yl-carbamoyl)-methyl]-piperidine-4-yl-amino}benzoic acid methyl ester chlorhidrate A mixture of 2-(Piperidine-4-yl-amino)-methyl benzoate (1100 mg, 4.70 mmol), 2-Chloro-N-(9-oxo-9H-fluoren-3-yl)-acetamide (1358 mg, 5 mmol) and $K_2CO_3$ (1380 mg, 10 mmol) in DMF (40 mL) was stirred at 10° C. for 2 hours and then at room temperature overnight. The reaction mixture was added to 50 mL water and 100 mL ethyl acetate, the organic phase was decanted and washed with water (3×50 mL), dried over sodium sulfate and a 2.8 M hydrogen chloride solution in absolute ethanol (1.80 mL) was added, to precipitate the hydrochloride, which was filtered off and washed with ethyl acetate. 1840 mg of a white solid were obtained. Yield: 77%.

Example 7a

Preparation of: 2-[4-2(2-Hidroxymethyl-4-methyl-phenylamino)-piperidine-1-yl]-N-phenyl-acetamide

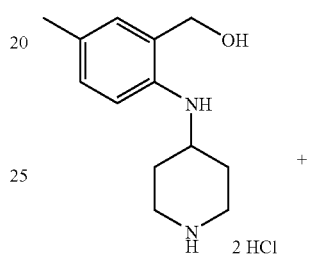

+

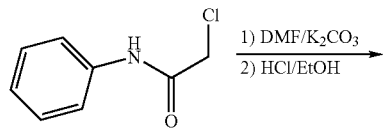

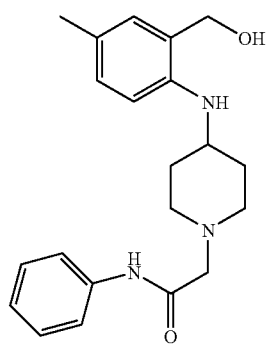

A mixture of 4-methyl-(2-hydroxymethylphenylamino)piperidine dihydrochloride (234 mg, 0.80 mmol), 2-Chloro-N-phenylacetamide (149 mg, 0.88 mmol) and $K_2CO_3$ (440 mg, 3.20 mmol) in DMF (10 mL) was stirred at room temperature overnight. The solvent is evaporated and $H_2O$ (15 mL) are added and the formed precipitate is extracted with ethyl acetate. The resulting phase is washed with water, dried and evaporated to dryness. The raw material was crystallized from ethyl acetate, filtered off and dried to give 178 mg of a white solid. Yield: 63%.

Example 8a

Preparation of 2-[4-(2-Hydroxymethyl-phenylamino)-piperidine-1-yl]-N-(1-oxo-indan-5-yl)-acetamide

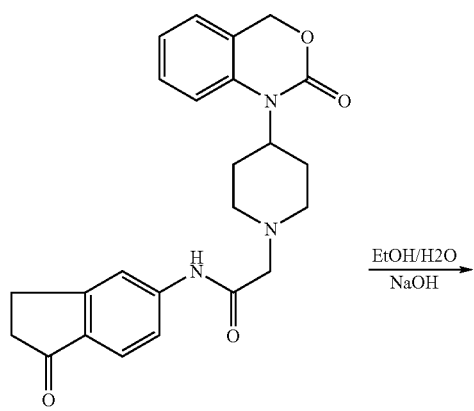

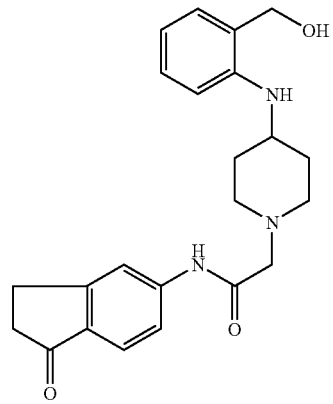

5 mL 10% sodium hydroxide were added to a suspension of 2-[4-(2-oxo-4H-benzo[d][1,3]oxazin-1-yl)-piperidine-1-yl]-N-(1-oxo-indan-5-yl)-acetamide (25 mg, 0.06 mmols) in 5 mL ethanol. The resulting mixture was heated to 50° C. for 2 hours, cooled, the ethanol was evaporated and the aqueous phase was neutralized and extracted with methylene chloride (2×15 mL). The combined organic extracts were washed with water, dried over sodium sulfate and evaporated to dryness. The crude material was purified via a silica gel column, eluting with ethyl acetate. 15 mg of a white solid were obtained, i.e. a yield of 64%.

N-(9-Ethyl-9H-carbazol-3-yl)-2-[4-(2-hydroxymethyl-6-methyl-phenylamino)-piperidin-yl]acetamide dihydrochloride

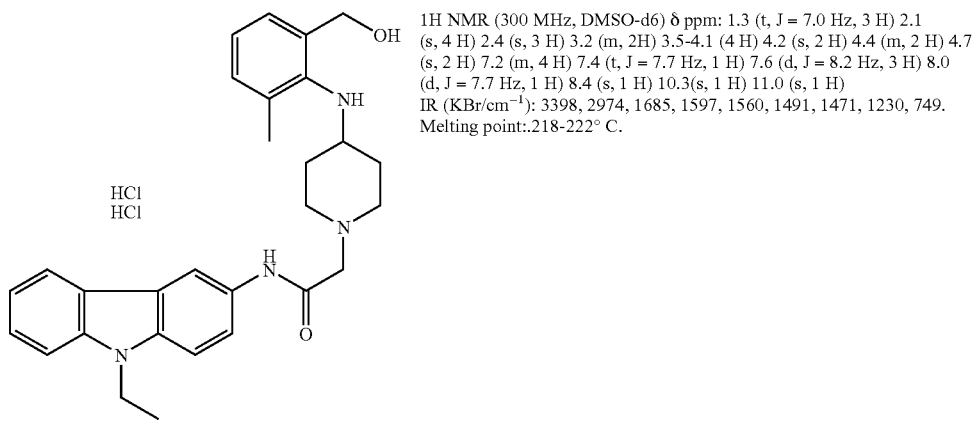

Ex. 1a

1H NMR (300 MHz, DMSO-d6) δ ppm: 1.3 (t, J = 7.0 Hz, 3 H) 2.1 (s, 4 H) 2.4 (s, 3 H) 3.2 (m, 2H) 3.5-4.1 (4 H) 4.2 (s, 2 H) 4.4 (m, 2 H) 4.7 (s, 2 H) 7.2 (m, 4 H) 7.4 (t, J = 7.7 Hz, 1 H) 7.6 (d, J = 8.2 Hz, 3 H) 8.0 (d, J = 7.7 Hz, 1 H) 8.4 (s, 1 H) 10.3(s, 1 H) 11.0 (s, 1 H)
IR (KBr/cm$^{-1}$): 3398, 2974, 1685, 1597, 1560, 1491, 1471, 1230, 749.
Melting point:.218-222° C.

-continued

2-[4-(2-Hydroxymethyl-4-methyl-phenylamino)-piperidin-1-yl]-N-(9-oxo-9H-fluoren-3-yl)-acetamide Ex. 2a

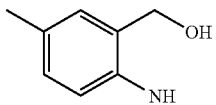
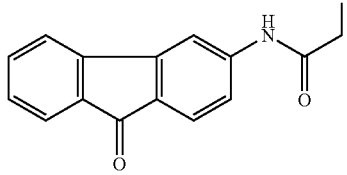

1H NMR (300 MHz, CDCl$_3$-d) δ ppm: 1.6 (m, 2 H) 2.2 (d, J = 13.9 Hz, 2 H) 2.2 (s, 3 H) 2.5 (t, J = 10.2 Hz, 2 H) 2.9 (d, J = 10.6 Hz, 2 H) 3.2 (s, 2 H) 3.4 (m, 1 H) 4.7 (s, 2 H) 6.6 (d, J = 8.2 Hz, 1 H) 6.9 (d, J = 1.6 Hz, 1 H) 7.0 (dd, J = 8.1, 1.7 Hz, 1 H) 7.3 (m, 2 H) 7.5 (td, J = 7.4, 1.1 Hz, 1 H) 7.6 (m, 3 H) 8.0 (d, J = 1.6 Hz, 1 H) 9.5 (s, 1 H)
IR (KBr/cm$^{-1}$): 3330, 3148, 1710, 1590, 1516, 1291, 1109, 980, 722
Melting point: 152° C.

2-[4-(2-Hydroxymethyl-6-methyl-phenylamino)-piperidin-1-yl]-N-(9-oxo-9H-fluoren-3-yl)-acetamide Ex. 3a

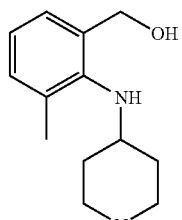
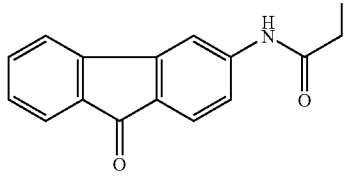

1H NMR (300 MHz, CDCl$_3$-d) δ ppm: 1.6 (d, J = 11.8, 2 H) 2.0 (d, J = 12.3 Hz, 2 H) 2.3 (s, 3 H) 2.4 (m, 2 H) 2.9 (d, J = 7.0 Hz, 2 H) 3.1 (m, 1 H) 3.2 (s, 2 H) 4.7 (s, 2 H) 6.9 (t, J = 7.4 Hz, 1 H) 7.0 (m, 1 H) 7.1 (d, J = 9.2 Hz, 1 H) 7.3 (m, 2 H) 7.5 (td, J = 7.4, 1.1 Hz, 1 H) 7.6 (m, 3 H) 8.0 (d, J = 1.8 Hz, 1 H) 9.4 (s, 1 H)
IR (KBr/cm$^{-1}$): 3414, 3269, 2920, 1710, 1692, 1609, 1508, 1230, 1101, 1002, 737.
Melting point: 113° C.

N-(9-Hydroxy-9H-fluoren-3-yl)-2-[4-(2-hydroxymethyl-4-methyl-phenylamino)-piperidin-1-yl]-acetamide Ex. 4a

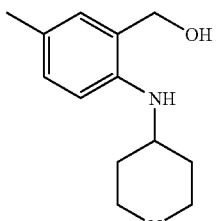
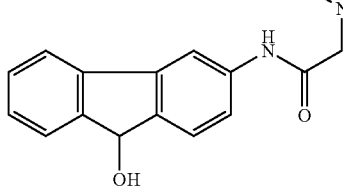

1H NMR (300 MHz, CDCl$_3$-d) δ ppm: 1.6 (m, 2 H) 2.1 (d, J = 14.3 Hz, 2 H) 2.2 (s, 3 H) 2.5 (m, 2 H) 2.9 (d, J = 12.5 Hz, 2 H) 3.1 (s, 2 H) 3.4 (m, 1 H) 4.6 (s, 2 H) 5.6 (s, 1 H) 6.6 (d, J = 8.2 Hz, 1 H) 6.9 (d, J = 1.8 Hz, 1 H) 7.0 (dd, J = 8.1, 1.9 Hz, 1 H) 7.4 (m, 3 H) 7.6 (m, 3 H) 8.0 (d, J = 1.8 Hz, 1 H) 9.3 (s, 1 H)
IR (KBr/cm$^{-1}$): 3300, 2920, 1670, 1613, 1521, 1025, 767.
Melting point: 124° C.

| Ex. 5a | N-(9-Hydroxy-9H-fluoren-3-yl)-2-[4-(2-hydroxymethyl-6-methyl-phenylamino)-piperidin-1-yl]-acetamide | |
|---|---|---|
| | 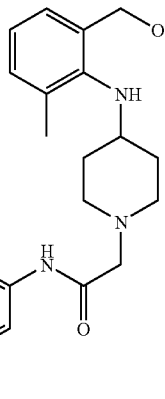 | 1H NMR (300 MHz, CDCl$_3$-d) δ ppm: 1.6 (m, 2 H) 2.0 (d, J = 10.4 Hz, 2 H) 2.3 (m, 5 H) 2.9 (d, J = 11.9 Hz, 2 H) 3.0 (m, 1 H) 3.1 (s, 2 H) 4.7 (s, 2 H) 5.6 (s, 1 H) 6.9 (t, J = 7.4 Hz, 1 H) 7.0 (m, 1 H) 7.1 (d, J = 9.0 Hz, 1 H) 7.4 (m, 3 H) 7.6 (m, 3 H) 8.0 (d, J = 2.0 Hz, 1 H) 9.2 (s, 1 H)<br>IR (KBr/cm$^{-1}$): 3315, 2927, 1676, 1527, 1097, 1025, 771, 737.<br>Melting point: 133° C. |

| Ex. 6a | 2-{1-[(9-Oxo-9H-fluoren-3-ylcarbamoyl)-methyl]-piperidin-4-ylamino}benzoic acid methyl ester hydrochloride | |
|---|---|---|
| | 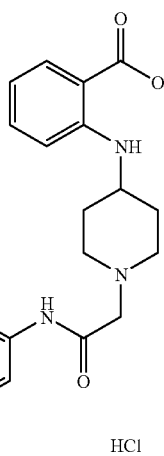 | 1H NMR (300 MHz, DMSO-d6) δ ppm: 1.8 (m, 2 H) 2.2 (d, J = 13.8 Hz, 2 H) 3.3 (m, 2 H) 3.6 (d, J = 10.8 Hz, 2 H) 3.8 (s, 3 H) 3.8 (m, 1 H) 4.2 (s, 2 H) 6.6 (t, J = 7.8 Hz, 1 H) 6.9 (d, J = 8.6 Hz, 1 H) 7.3 (m, 2 H) 7.5 (m, 4 H) 7.6 (m, 1 H) 7.8 (dd, J = 8.0, 1.6 Hz, 1 H) 8.0 (d, J = 1.3 Hz, 1 H) 10.1 (s, 1 H) 11.1 (s, 1 H)<br>IR (KBr/cm$^{-1}$): 2946, 2539, 1700, 1684, 1603, 1560, 1255, 748.<br>Melting point: 258° C. |

| Ex. 7a | 2-[4-(2-Hydroxymethyl-4-methyl-phenylamino)-piperidin-1-yl]-N-phenyl-acetamide | |
|---|---|---|
| | 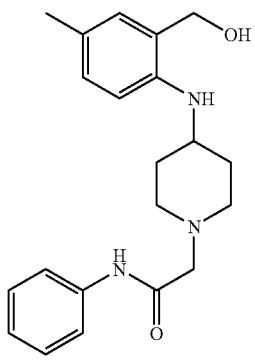 | 1H NMR (300 MHz, CDCl$_3$-d) δ ppm: 1.6 (m, 2 H) 2.1 (d, J = 13.0 Hz, 2 H) 2.2 (s, 3 H) 2.4 (t, J = 10.3 Hz, 2 H) 2.9 (d, J = 11.9 Hz, 2 H) 3.1 (s, 2 H) 3.4 (m, 1 H) 4.6 (s, 2 H) 6.6 (d, J = 8.2 Hz, 1 H) 6.9 (s, 1 H) 7.0 (dd, J = 8.2, 1.5 Hz, 1 H) 7.1 (t, J = 7.4 Hz, 1 H) 7.3 (t, J = 7.9 Hz, 2 H) 7.6 (d, J = 7.7 Hz, 2 H) 9.2 (s, 1 H)<br>IR (KBr/cm$^{-1}$): 3346, 1691, 1598, 1543, 1438, 1317, 748.<br>Melting point: 128° C. |

| Ex. | | | |
|---|---|---|---|
| 8 | 2-[4-(2-Hydroxymethyl-phenylamino)-piperidin-1-yl]-N-phenyl-acetamide 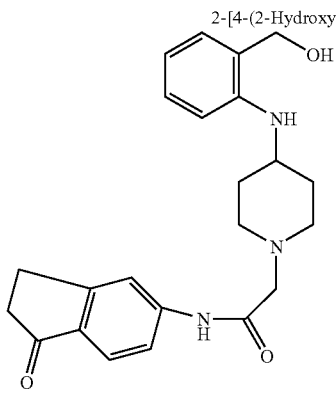 | IR (KBr): 3398, 2923, 1710, 1655, 1590, 1541, 1425, 1287, 1126, 1013<br>melting point: 138-140° C. | |

Example 9a

Example of a Tablet Formulation

| | |
|---|---|
| Compound according to example 6a | 5 mg |
| Lactose | 60 mg |
| Crystalline cellulose | 25 mg |
| Povidone K 90 | 5 mg |
| Pregelanitized starch | 3 mg |

-continued

| | |
|---|---|
| Colloidal silica dioxide | 1 mg |
| Magnesium stearate | 1 mg |
| Total weight per tablet | 100 mg |

The above mentioned ingredients were mixed and compressed into a tablet by conventional methods known to those skilled in the art.

The compounds according to the following list B have also been prepared by the methods described above:

List B:

| N° | Structure | Name Autonom® | MS APCI M + H⁺ | NMR |
|---|---|---|---|---|
| 1 | 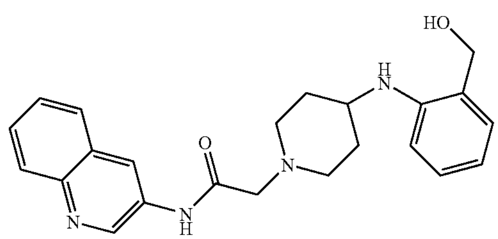 | 2-[4-(2-ydroxymethyl-phenylamino)-piperidin-1-yl]-N-quinolin-3-yl-acetamide | 391 | 1H NMR (300 MHz, DMSO-D6) δ ppm 1.56 (m, 2 H), 1.96 (d, J = 11.71 Hz, 2 H), 2.38 (m, 2 H), 2.87 (m, 2 H), 3.22 (s, 2 H), 4.41 (m, 2 H), 4.97 (d, J = 7.32 Hz, 1 H), 5.20 (s, 1 H), 6.51 (t, J = 7.17 Hz, 1 H), 6.63 (d, J = 7.76 Hz, 1 H), 7.04 (m, 2 H), 7.59 (m, 2 H), 7.93 (t, J = 8.20 Hz, 2 H), 8.71 (d, J = 2.49 Hz, 1 H), 9.00 (d, J = 2.49 Hz, 1 H), 10.19 (s, 1 H) |
| 2 | 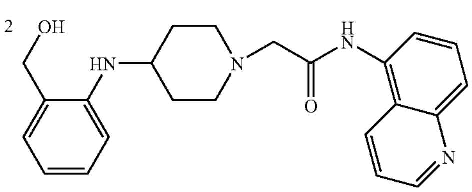 | 2-[4-(2-Hydroxymethyl-phenylamino)-piperidin-1-yl]-N-quinolin-5-yl-acetamide | 391 | 1H NMR (300 MHz, DMSO-D6) δ ppm 1.59 (q, J = 9.32 Hz, 2 H), 2.01 (m, 2 H), 2.44 (m, 2 H), 2.94 (d, J = 10.69 Hz, 2 H), 3.27 (s, 2 H), 4.42 (d, J = 5.27 Hz, 2 H), 4.99 (d, J = 7.61 Hz, 1 H), 5.17 (t, J = 5.27 Hz, 1 H), 6.52 (t, J = 7.25 Hz, 1 H), 6.64 (d, J = 7.91 Hz, 1 H), 7.04 (m, 2 H), 7.58 (dd, J = 8.49, 4.25 Hz, 1 H), 7.73 (m, 1 H), 7.84 (m, 2 H), 8.31 (d, J = 8.20 Hz, 1 H), 8.91 (d, J = 4.39 Hz, 1 H), 10.07 (s, 1 H) |

-continued

| N° | Structure | Name Autonom ® | MS APCI M + H⁺ | NMR |
|---|---|---|---|---|
| 3 | 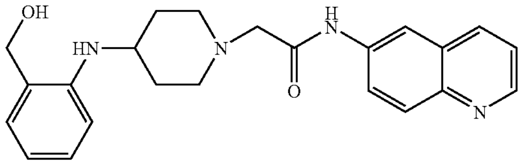 | 2-[4-(2-Hydroxymethyl-phenylamino)-piperidin-1-yl]-N-quinolin-6-yl-acetamide | 391 | 1H NMR (300 MHz, DMSO-D6) δ ppm 1.55 (m, 2 H), 1.96 (d, J = 10.84 Hz, 2 H), 2.38 (t, J = 10.10 Hz, 2 H), 2.86 (d, J = 9.08 Hz, 2 H), 3.20 (s, 2 H), 4.41 (d, J = 5.12 Hz, 2 H), 4.97 (d, J = 7.32 Hz, 1 H), 5.16 (t, J = 5.27 Hz, 1 H), 6.51 (t, J = 7.32 Hz, 1 H), 6.62 (d, J = 8.05 Hz, 1 H), 7.05 (m, 2 H), 7.46 (dd, J = 8.27, 4.32 Hz, 1 H), 7.91 (m, 2 H), 8.27 (m, 1 H), 8.39 (d, J = 2.20 Hz, 1 H), 8.77 (dd, J = 4.17, 1.68 Hz, 1 H), 10.03 (s, 1 H) |
| 4 | 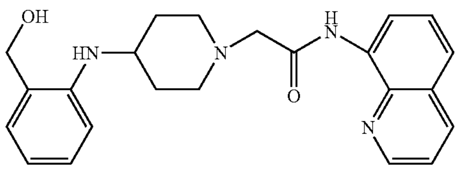 | 2-[4-(2-Hydroxymethyl-phenylamino)-piperidin-1-yl]-N-quinolin-8-yl-acetamide | 391 | |
| 5 | 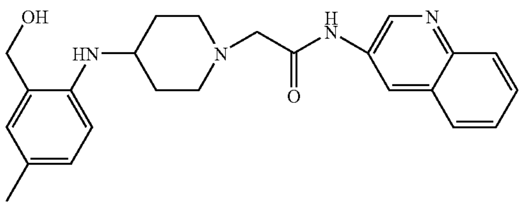 | 2-[4-(2-Hydroxymethyl-4-methyl-phenylamino)-piperidin-1-yl]-N-quinolin-3-yl-acetamide | 405 | 1H NMR (300 MHz, DMSO-D6) δ ppm 1.54 (m, 2 H), 1.95 (d, J = 11.42 Hz, 2 H), 2.13 (s, 3 H), 2.36 (m, 2 H), 2.86 (d, J = 9.37 Hz, 2 H), 3.22 (s, 2 H), 4.38 (d, J = 5.27 Hz, 2 H), 4.75 (m, 1 H), 5.11 (m, 1 H), 6.53 (d, J = 7.91 Hz, 1 H), 6.87 (m, 2 H), 7.60 (m, 2 H), 7.92 (t, J = 8.42 Hz, 2 H), 8.71 (d, J = 2.34 Hz, 1 H), 9.00 (d, J = 2.49 Hz, 1 H), 10.16 (s, 1 H) |
| 6 | 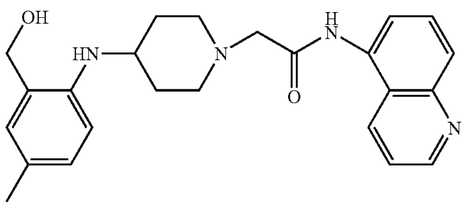 | 2-[4-(2-Hydroxymethyl-4-methyl-phenylamino)-piperidin-1-yl]-N-quinolin-5-yl-acetamide | 405 | 1H NMR (300 MHz, DMSO-D6) δ ppm 1.57 (m, 2 H), 2.00 (m, 2 H), 2.14 (s, 3 H), 2.41 (m, 2 H), 2.93 (d, J = 9.08 Hz, 2 H), 3.26 (s, 2 H), 4.38 (d, J = 5.12 Hz, 2 H), 4.78 (d, J = 7.76 Hz, 1 H), 5.12 (t, J = 5.20 Hz, 1 H), 6.55 (d, J = 7.61 Hz, 1 H), 6.86 (m, 2 H), 7.58 (dd, J = 8.57, 4.17 Hz, 1 H), 7.73 (m, 1 H), 7.84 (m, 2 H), 8.31 (m, 1 H), 8.91 (dd, J = 4.10, 1.46 Hz, 1 H), 10.07 (s, 1 H) |
| 7 | 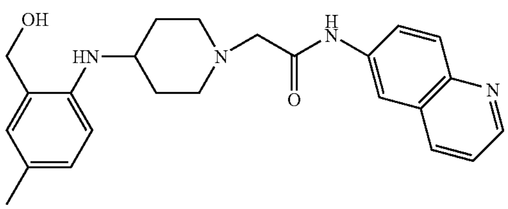 | 2-[4-(2-Hydroxymethyl-4-methyl-phenylamino)-piperidin-1-yl]-N-quinolin-6-yl-acetamide | 405 | 1H NMR (300 MHz, DMSO-D6) δ ppm 1.52 (m, 2 H), 1.94 (d, J = 9.81 Hz, 2 H), 2.13 (s, 3 H), 2.36 (t, J = 10.91 Hz, 2 H), 2.87 (m, 2 H), 3.19 (s, 2 H), 4.37 (d, J = 4.98 Hz, 2 H), 4.76 (d, J = 7.76 Hz, 1 H), 5.12 (t, J = 5.34 Hz, 1 H), 6.53 (d, J = 8.20 Hz, 1 H), 6.87 (m, 2 H), 7.46 (m, 1 H), 7.92 (m, 2 H), 8.26 (s, 1 H), 8.38 (s, 1 H), 8.77 (d, J = 4.25 Hz, 1 H), 10.03 (s, 1 H) |
| 8 | 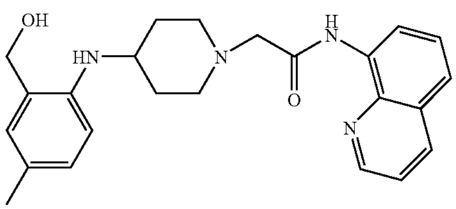 | 2-[4-(2-Hydroxymethyl-4-methyl-phenylamino)-piperidin-1-yl]-N-quinolin-8-yl-acetamide | 405 | 1H NMR (300 MHz, DMSO-D6) δ ppm 1.63 (m, 2 H), 2.03 (m, 2 H), 2.14 (s, 3 H), 2.42 (m, 2 H), 2.89 (m, 2 H), 3.25 (s, 2 H), 4.42 (d, J = 5.42 Hz, 2 H), 4.86 (d, J = 7.61 Hz, 1 H), 5.18 (t, J = 5.20 Hz, 1 H), 6.56 (d, J = 8.79 Hz, 1 H), 6.88 (m, 2 H), 7.62 (m, 3 H), 8.40 (dd, J = 8.35, 1.61 Hz, 1 H), 8.64 (dd, J = 7.47, 1.46 Hz, 1 H), 8.92 (dd, J = 4.25, 1.61 Hz, 1 H), 11.38 (s, 1 H) |
| 9 | 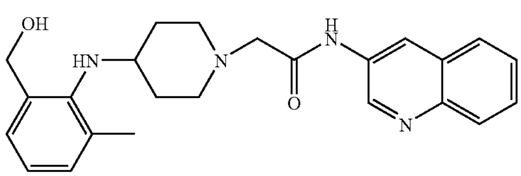 | 2-[4-(2-Hydroxymethyl-6-methyl-phenylamino)-piperidin-1-yl]-N-quinolin-3-yl-acetamide | 405 | 1H NMR (300 MHz, DMSO-D6) δ ppm 1.55 (m, 2 H), 1.76 (d, J = 10.40 Hz, 2 H), 2.20 (m, 5 H), 2.87 (m, 2 H), 3.19 (s, 2 H), 4.12 (d, J = 10.40 Hz, 1 H), 4.48 (d, J = 5.27 Hz, 2 H), 5.19 (t, J = 5.20 Hz, 1 H), 6.75 (t, J = 7.39 Hz, 1 H), 7.00 (d, J = 6.88 Hz, 1 H), 7.56 (m, 1 H), 7.61 (s, 1 H), 7.92 (t, J = 8.86 Hz, 2 H), 8.69 (d, J = 2.34 Hz, 1 H), 8.98 (d, J = 2.34 Hz, 1 H), 10.15 (s, 1 H) |

| N° | Structure | Name Autonom ® | MS APCI M + H⁺ | NMR |
|---|---|---|---|---|
| 10 | (structure) | 2-[4-(2-Hydroxymethyl-6-methyl-phenylamino)-piperidin-1-yl]-N-quinolin-5-yl-acetamide | 405 | 1H NMR (300 MHz, DMSO-D6) δ ppm 1.58 (m, 2 H), 1.80 (d, J = 10.10 Hz, 2 H), 2.22 (s, 3 H), 2.26 (m, 2 H), 2.94 (d, J = 11.13 Hz, 2 H), 3.23 (s, 2 H), 4.14 (d, J = 10.40 Hz, 1 H), 4.49 (d, J = 5.27 Hz, 2 H), 5.19 (t, J = 5.27 Hz, 1 H), 6.76 (t, J = 7.47 Hz, 1 H), 7.01 (d, J = 14.35 Hz, 1 H), 7.59 (dd, J = 8.49, 4.10 Hz, 1 H), 7.78 (m, 3 H), 8.31 (dd, J = 7.76, 0.73 Hz, 1 H), 8.92 (dd, J = 4.17, 1.39 Hz, 1 H), 10.05 (s, 1 H) |
| 11 | (structure) | 2-[4-(2-Hydroxymethyl-6-methyl-phenylamino)-piperidin-1-yl]-N-quinolin-6-yl-acetamide | 405 | 1H NMR (300 MHz, DMSO-D6) δ ppm 1.54 (m, 2 H), 1.76 (d, J = 10.69 Hz, 2 H), 2.20 (m, 5 H), 2.86 (d, J = 10.98 Hz, 3 H), 3.16 (s, 2 H), 4.11 (d, J = 10.40 Hz, 1 H), 4.48 (d, J = 5.42 Hz, 2 H), 5.19 (t, J = 5.27 Hz, 1 H), 6.75 (t, J = 7.39 Hz, 1 H), 7.02 (m, 2 H), 7.46 (dd, J = 8.20, 4.25 Hz, 1 H), 7.87 (m, 1 H), 7.95 (m, 1 H), 8.28 (m, 1 H), 8.37 (d, J = 2.20 Hz, 1 H), 8.77 (m, 1 H), 10.00 (s, 1 H) |
| 12 | (structure) | 2-[4-(2-Hydroxymethyl-6-methyl-phenylamino)-piperidin-1-yl]-N-quinolin-8-yl-acetamide | 405 | 1H NMR (300 MHz, DMSO-D6) δ ppm 1.65 (m, 2 H), 1.83 (d, J = 9.52 Hz, 2 H), 2.24 (s, 3 H), 2.28 (m, 2 H), 2.89 (d, J = 10.25 Hz, 2 H), 3.22 (s, 2 H), 4.26 (d, J = 9.96 Hz, 1 H), 4.54 (d, J = 4.83 Hz, 2 H), 5.29 (t, J = 5.20 Hz, 1 H), 6.77 (t, J = 7.39 Hz, 1 H), 7.05 (m, 2 H), 7.57 (t, J = 7.91 Hz, 1 H), 7.66 (m, 1 H), 8.41 (dd, J = 8.20, 1.32 Hz, 1 H), 8.63 (d, J = 7.03 Hz, 1 H), 8.98 (m, 1 H), 11.40 (s, 1 H) |
| 13 | (structure) | N-(4-Benzoyl-phenyl)-2-[4-(2-hydroxymethyl-phenylamino)-piperidin-1-yl]-acetamide | 444 | 1H NMR (300 MHz, DMSO-D6) δ ppm 1.53 (m, 2 H), 1.95 (m, 2 H), 2.35 (t, J = 10.32 Hz, 2 H), 2.84 (m, 2 H), 3.18 (s, 2 H), 4.40 (d, J = 5.27 Hz, 2 H), 4.95 (d, J = 7.61 Hz, 1 H), 5.16 (t, J = 5.34 Hz, 1 H), 6.51 (t, J = 7.25 Hz, 1 H), 6.62 (d, J = 7.91 Hz, 1 H), 7.05 (m, 2 H), 7.53 (m, 2 H), 7.68 (m, 5 H), 7.84 (m, 2 H), 10.09 (s, 1 H) |
| 14 | (structure) | N-(4-Benzoyl-phenyl)-2-[4-(2-hydroxymethyl-4-methyl-phenylamino)-piperidin-1-yl]-acetamide | 458 | 1H NMR (300 MHz, DMSO-D6) δ ppm 1.50 (m, 2 H), 1.93 (d, J = 10.54 Hz, 2 H), 2.13 (s, 3 H), 2.34 (m, 2 H), 2.81 (m, 2 H), 3.17 (s, 2 H), 4.37 (d, J = 5.27 Hz, 2 H), 4.75 (d, J = 7.76 Hz, 1 H), 5.10 (m, 1 H), 6.52 (d, J = 7.91 Hz, 1 H), 6.87 (m, 2 H), 7.53 (m, 2 H), 7.68 (m, 5 H), 7.83 (m, 2 H), 10.09 (s, 1 H) |
| 15 | (structure) | N-(4-Benzoyl-phenyl)-2-[4-(2-hydroxymethyl-6-methyl-phenylamino)-piperidin-1-yl]-acetamide | 458 | 1H NMR (300 MHz, DMSO-D6) δ ppm 1.51 (m, 2 H), 1.75 (d, J = 11.13 Hz, 2 H), 2.17 (m, 2 H), 2.20 (s, 3 H), 2.83 (m, 3 H), 3.14 (s, 2 H), 4.11 (d, J = 10.69 Hz, 1 H), 4.47 (d, J = 5.12 Hz, 2 H), 5.18 (t, J = 5.20 Hz, 1 H), 6.75 (t, J = 7.39 Hz, 1 H), 7.02 (dd, J = 14.42, 7.39 Hz, 2 H), 7.54 (t, J = 7.39 Hz, 2 H), 7.68 (m, 5 H), 7.82 (m, 2 H), 10.06 (s, 1 H) |

| N° | Structure | Name Autonom ® | MS APCI M + H⁺ | NMR |
|---|---|---|---|---|
| 16 | 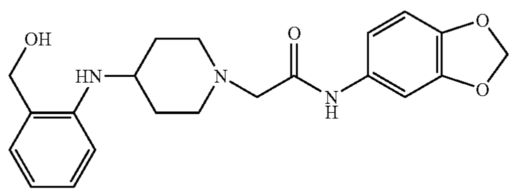 | N-Benzo[1,3]dioxol-5-yl-2-[4-(2-hydroxymethyl-phenylamino)-piperidin-1-yl]-acetamide | 384 | |
| 17 | 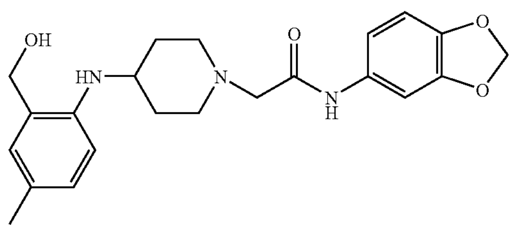 | N-Benzo[1,3]dioxol-5-yl-2-[4-(2-hydroxymethyl-4-methyl-phenylamino)-piperidin-1-yl]-acetamide | 398 | 1H NMR (300 MHz, DMSO-D6) δ ppm 1.49 (q, J = 9.71 Hz, 2 H), 1.92 (d, J = 10.69 Hz, 2 H), 2.13 (s, 3 H), 2.30 (t, J = 10.84 Hz, 2 H), 2.79 (d, J = 11.27 Hz, 2 H), 3.07 (s, 2 H), 3.26 (m, 1 H), 4.36 (d, J = 5.42 Hz, 2 H), 4.74 (d, J = 7.61 Hz, 1 H), 5.11 (t, J = 5.34 Hz, 1 H), 5.96 (s, 2 H), 6.52 (d, J = 7.76 Hz, 1 H), 6.83 (m, 3 H), 7.03 (dd, J = 8.49, 2.05 Hz, 1 H), 7.33 (d, J = 1.90 Hz, 1 H), 9.58 (s, 1 H) |
| 18 | 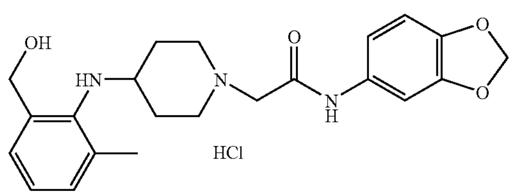 | N-Benzo[1,3]dioxol-5-yl-2-[4-(2-hydroxymethyl-6-methyl-phenylamino)-piperidin-1-yl]-acetamide hydrochloride | | |
| 19 | 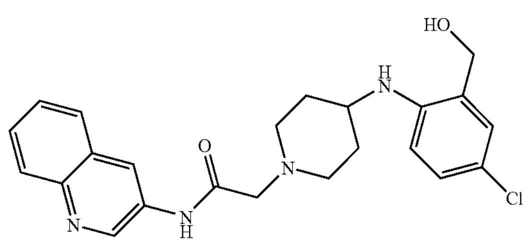 | 2-[4-(4-Chloro-2-hydroxymethyl-phenylamino)-piperidin-1-yl]-N-quinolin-3-yl-acetamide | | |
| 20 | 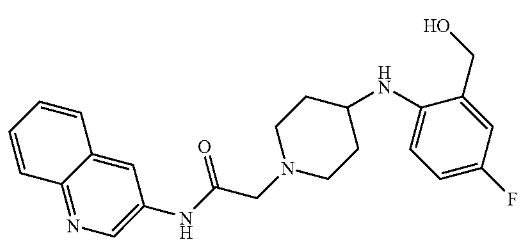 | 2-[4-(4-Fluoro-2-hydroxymethyl-phenylamino)-piperidin-1-yl]-N-quinolin-3-yl-acetamide | | |
| 21 | 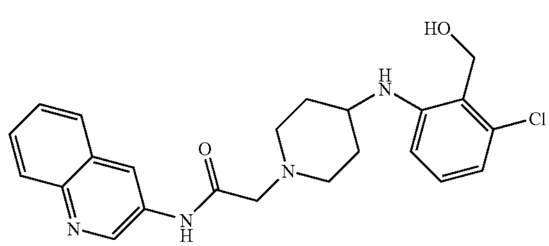 | 2-[4-(3-Chloro-2-hydroxymethyl-phenylamino)-piperidin-1-yl]-N-quinolin-3-yl-acetamide | | |

-continued

| N° | Structure | Name Autonom ® | MS APCI M + H⁺ | NMR |
|---|---|---|---|---|
| 22 | 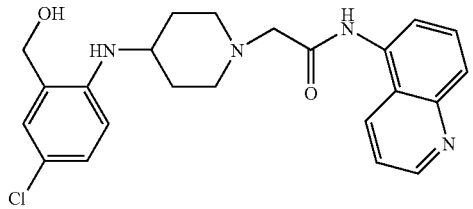 | 2-[4-(4-Chloro-2-hydroxymethyl-phenylamino)-piperidin-1-yl]-N-quinolin-5-yl-acetamide | | |
| 23 | 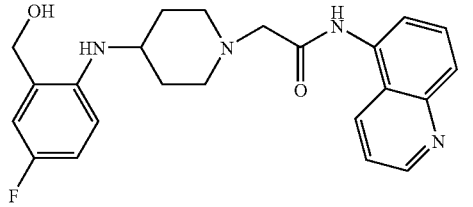 | 2-[4-(4-Fluoro-2-hydroxymethyl-phenylamino)-piperidin-1-yl]-N-quinolin-5-yl-acetamide | | |
| 24 | 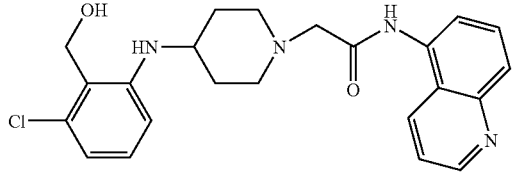 | 2-[4-(3-Chloro-2-hydroxymethyl-phenylamino)-piperidin-1-yl]-N-quinolin-5-yl-acetamide | | |
| 25 | 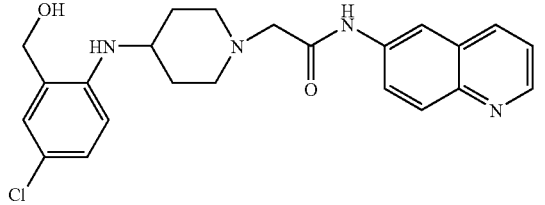 | 2-[4-(4-Chloro-2-hydroxymethyl-phenylamino)-piperidin-1-yl]-N-quinolin-6-yl-acetamide | | |
| 26 | 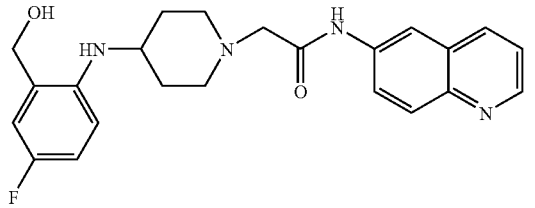 | 2-[4-(4-Fluoro-2-hydroxymethyl-phenylamino)-piperidin-1-yl]-N-quinolin-6-yl-acetamide | | |
| 27 | 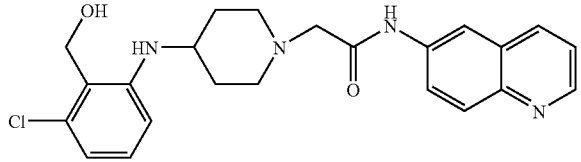 | 2-[4-(3-Chloro-2-hydroxymethyl-phenylamino)-piperidin-1-yl]-N-quinolin-6-yl-acetamide | | |
| 28 | 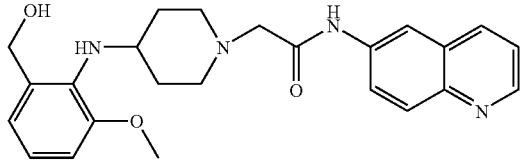 | 2-[4-(2-Hydroxymethyl-6-methoxy-phenylamino)-piperidin-1-yl]-N-quinolin-6-yl-acetamide | | |

| N° | Structure | Name Autonom® | MS APCI M + H⁺ | NMR |
|---|---|---|---|---|
| 29 | 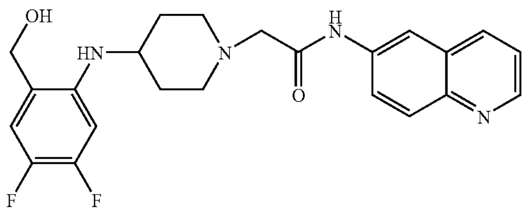 | 2-[4-(4,5-Difluoro-2-hydroxymethyl-phenylamino)-piperidin-1-yl]-N-quinolin-6-yl-acetamide | | |
| 30 | 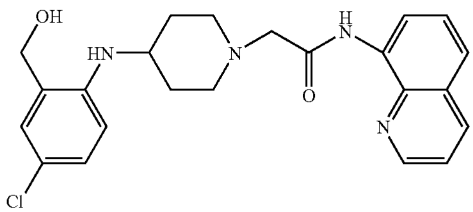 | 2-[4-(4-Chloro-2-hydroxymethyl-phenylamino)-piperidin-1-yl]-N-quinolin-8-yl-acetamide | | |
| 31 | 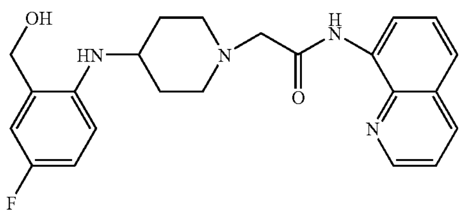 | 2-[4-(4-Fluoro-2-hydroxymethyl-phenylamino)-piperidin-1-yl]-N-quinolin-8-yl-acetamide | | |
| 32 | 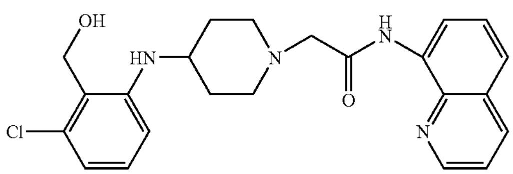 | 2-[4-(3-Chloro-2-hydroxymethyl-phenylamino)-piperidin-1-yl]-N-quinolin-8-yl-acetamide | | |
| 33 | 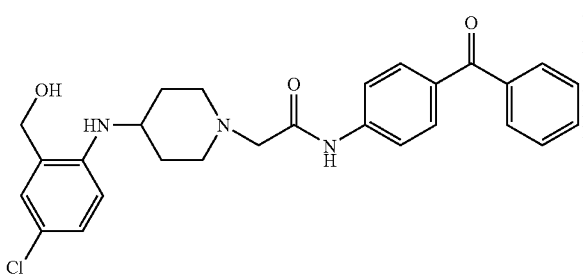 | N-(4-Benzoyl-phenyl)-2-[4-(4-chloro-2-hydroxymethyl-phenylamino)-piperidin-1-yl]-acetamide | | |
| 34 | 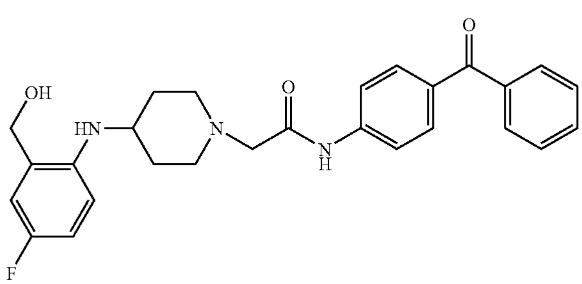 | N-(4-Benzoyl-phenyl)-2-[4-(4-fluoro-2-hydroxymethyl-phenylamino)-piperidin-1-yl]-acetamide | | |

-continued

| N° | Structure | Name Autonom ® | MS APCI M + H⁺ | NMR |
|---|---|---|---|---|
| 35 | 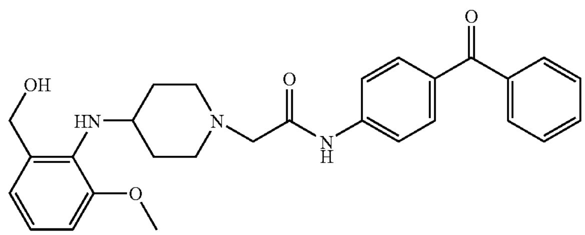 | N-(4-Benzoyl-phenyl)-2-[4-(2-hydroxymethyl-6-methoxy-phenylamino)-piperidin-1-yl]-acetamide | | |
| 36 | 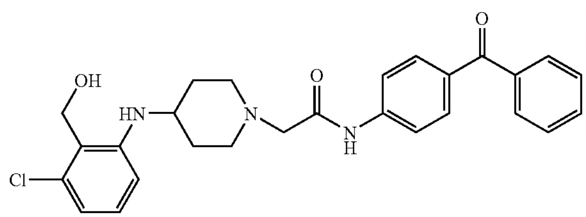 | N-(4-Benzoyl-phenyl)-2-[4-(3-chloro-2-hydroxymethyl-phenylamino)-piperidin-1-yl]-acetamide | | |
| 37 | 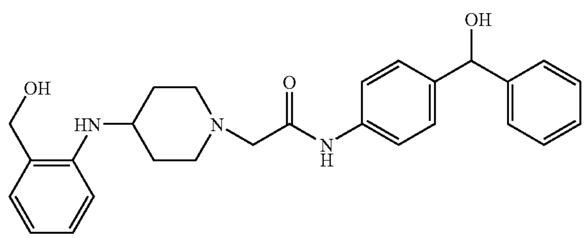 | 2-[4-(2-Hydroxymethyl-phenylamino)-piperidin-1-yl]-N-[4-(hydroxy-phenyl-methyl)-phenyl]-acetamide | | |
| 38 | 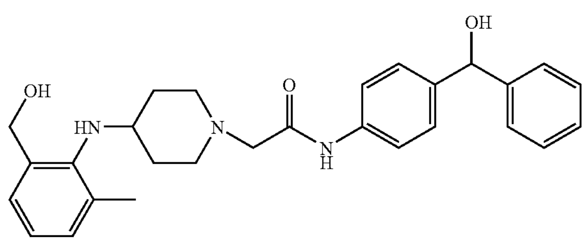 | 2-[4-(2-Hydroxymethyl-6-methyl-phenylamino)-piperidin-1-yl]-N-[4-(hydroxy-phenyl-methyl)-phenyl]-acetamide | | |
| 39 | 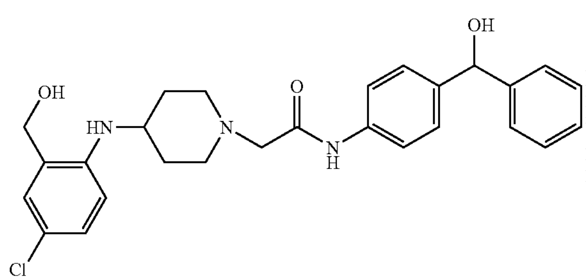 | 2-[4-(4-Chloro-2-hydroxymethyl-phenylamino)-piperidin-1-yl]-N-[4-(hydroxy-phenyl-methyl)-phenyl]-acetamide | | |
| 40 | 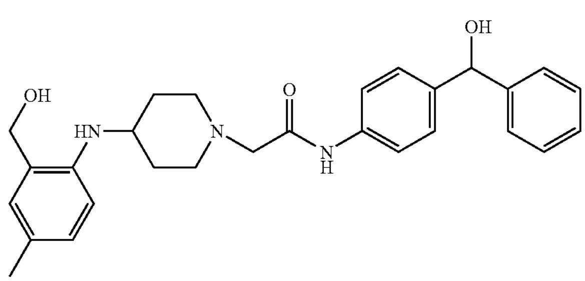 | 2-[4-(2-Hydroxymethyl-4-methyl-phenylamino)-piperidin-1-yl]-N-[4-(hydroxy-phenyl-methyl)-phenyl]-acetamide | | |

| N° | Structure | Name Autonom ® | MS APCI M + H⁺ | NMR |
|----|-----------|----------------|----------------|-----|
| 41 | 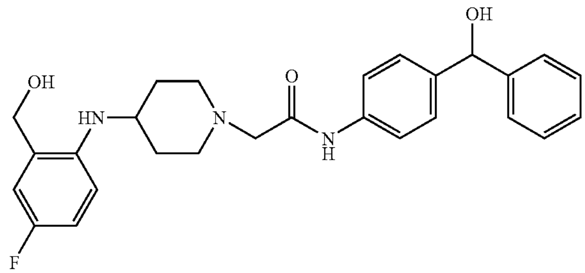 | 2-[4-(4-Fluoro-2-hydroxymethyl-phenylamino)-piperidin-1-yl]-N-[4-(hydroxy-phenyl-methyl)-phenyl]-acetamide | | |
| 42 | 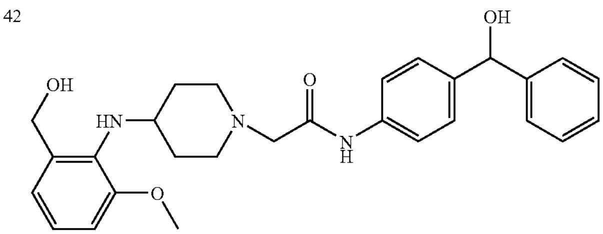 | 2-[4-(2-Hydroxymethyl-6-methoxy-phenylamino)-piperidin-1-yl]-N-[4-(hydroxy-phenyl-methyl)-phenyl]-acetamide | | |
| 43 | 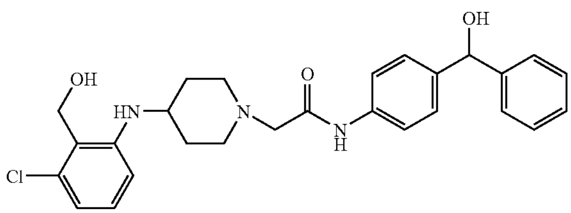 | 2-[4-(3-Chloro-2-hydroxymethyl-phenylamino)-piperidin-1-yl]-N-[4-(hydroxy-phenyl-methyl)-phenyl]-acetamide | | |
| 44 | 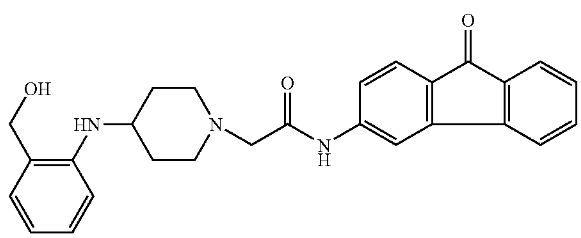 | 2-[4-(2-Hydroxymethyl-phenylamino)-piperidin-1-yl]-N-(9-oxo-9H-fluoren-3-yl)-acetamide | | |
| 45 | 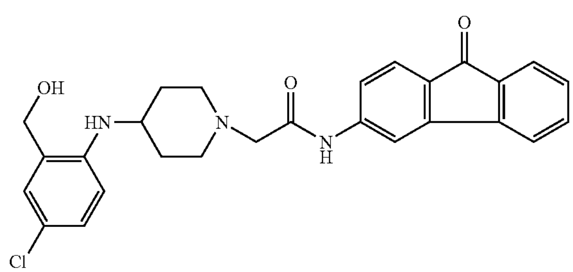 | 2-[4-(4-Chloro-2-hydroxymethyl-phenylamino)-piperidin-1-yl]-N-(9-oxo-9H-fluoren-3-yl)-acetamide | | |
| 46 | 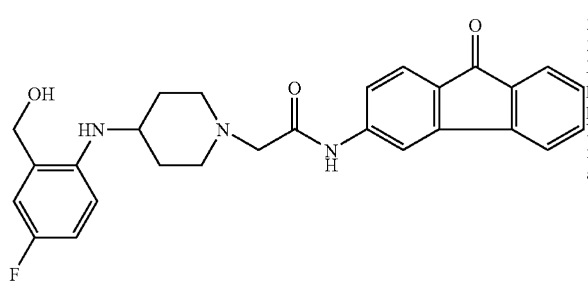 | 2-[4-(4-Fluoro-2-hydroxymethyl-phenylamino)-piperidin-1-yl]-N-(9-oxo-9H-fluoren-3-yl)-acetamide | | |

-continued

| N° | Structure | Name Autonom® | MS APCI M + H⁺ | NMR |
|---|---|---|---|---|
| 47 | 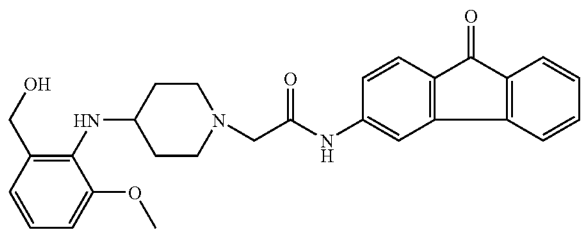 | 2-[4-(2-Hydroxymethyl-6-methoxy-phenylamino)-piperidin-1-yl]-N-(9-oxo-9H-fluoren-3-yl)-acetamide | | |
| 48 | 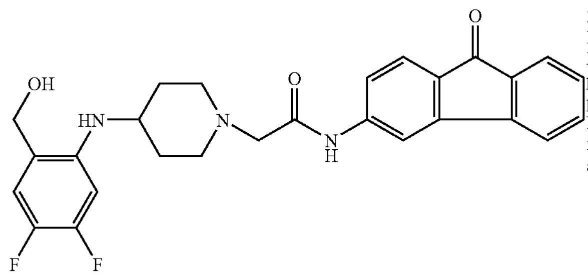 | 2-[4-(4,5-Difluoro-2-hydroxymethyl-phenylamino)-piperidin-1-yl]-N-(9-oxo-9H-fluoren-3-yl)-acetamide | | |
| 49 | 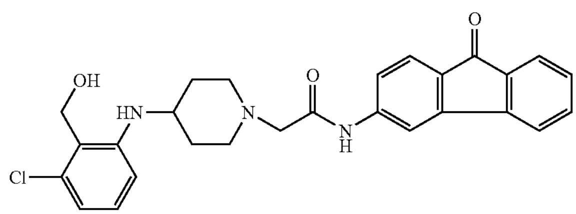 | 2-[4-(3-Chloro-2-hydroxymethyl-phenylamino)-piperidin-1-yl]-N-(9-oxo-9H-fluoren-3-yl)-acetamide | | |
| 50 | 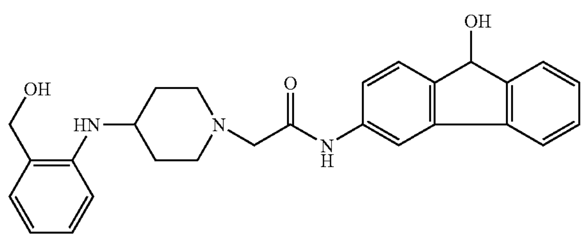 | N-(9-Hydroxy-9H-fluoro-3-yl)-2-[4-(2-hydroxymethyl-phenylamino)-piperidin-1-yl]-acetamide | | |
| 51 | 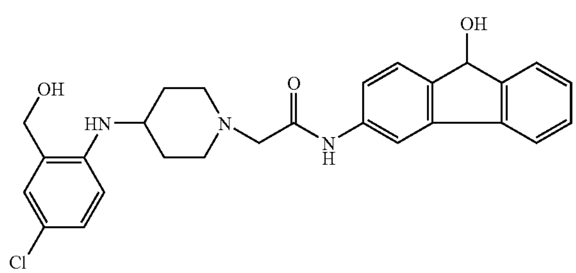 | 2-[4-(4-Chloro-2-hydroxymethyl-phenylamino)-piperidin-1-yl]-N-(9-hydroxy-9H-fluoren-3-yl)-acetamide | | |
| 52 | 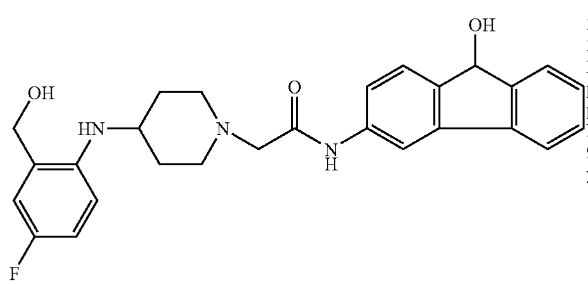 | 2-[4-(4-Fluoro-2-hydroxymethyl-phenylamino)-piperidin-1-yl]-N-(9-hydroxy-9H-fluoren-3-yl)-acetamide | | |

| N° | Structure | Name Autonom ® | MS APCI M + H⁺ | NMR |
|---|---|---|---|---|
| 53 | 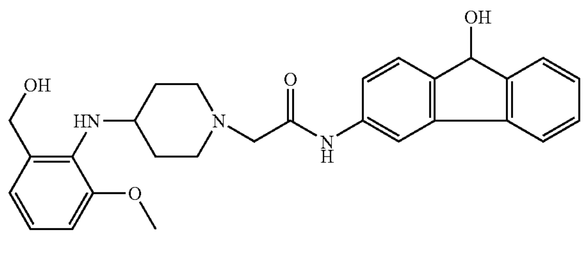 | N-(9-hydroxy-9H-fluoren-3-yl)-2-[4-(2-hydroxymethyl-6-methoxy-phenylamino)-piperidin-1-yl]-acetamide | | |
| 54 | 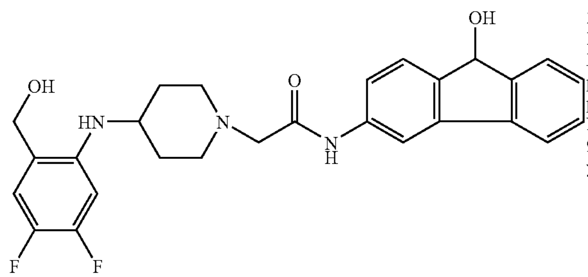 | 2-[4-(4,5-Difluoro-2-hydroxymethyl-phenylamino)-piperidin-1-yl]-N-(9-hydroxy-9H-fluoren-3-yl)-acetamide | | |
| 55 | 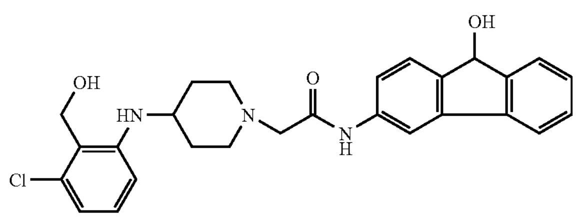 | 2-[4-(3-Chloro-2-hydroxymethyl-phenylamino)-piperidin-1-yl]-N-(9-hydroxy-9H-fluoren-3-yl)-acetamide | | |
| 56 | 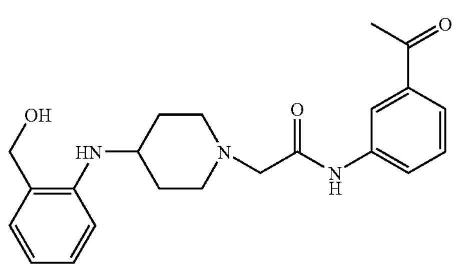 | N-(3-Acetyl-phenyl)-2-[4-(2-hydroxymethyl-phenylamino)-piperidin-1-yl]-acetamide | | |
| 57 | 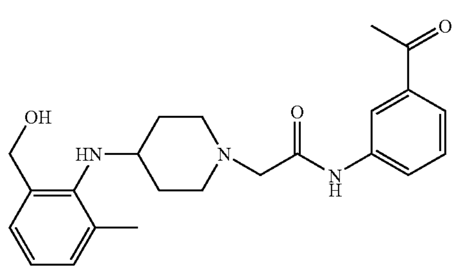 | N-(3-Acetyl-phenyl)-2-[4-(2-hydroxymethyl-6-methyl-phenylamino)-piperidin-1-yl]-acetamide | | |

-continued

| N° | Structure | Name Autonom ® | MS APCI M + H⁺ | NMR |
|---|---|---|---|---|
| 58 | 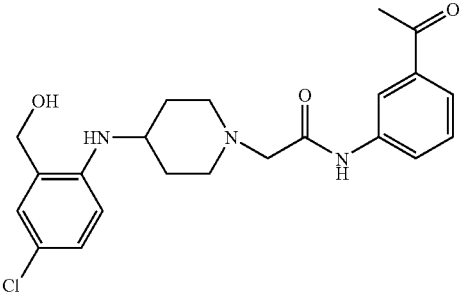 | N-(3-Acetyl-phenyl)-2-[4-(2-chloro-2-hydroxymethyl-phenylamino)-piperidin-1-yl]-acetamide | | |
| 59 | 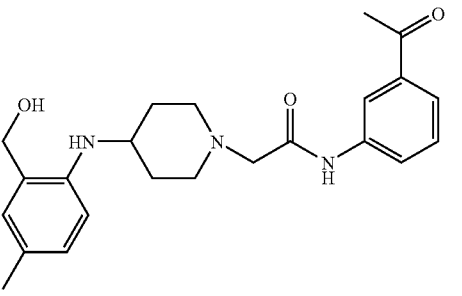 | N-(3-Acetyl-phenyl)-2-[4-(2-hydroxymethyl-4-methyl-phenylamino)-piperidin-1-yl]-acetamide | | |
| 60 | 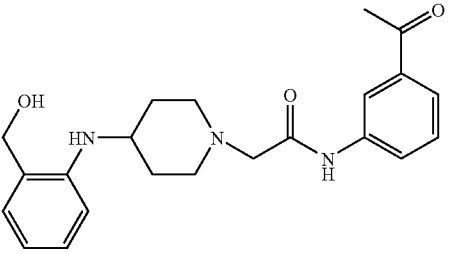 | N-[3-(1-Hydroxy-ethyl)-phenyl)-2-[4-(2-hydroxymethyl-phenylamino)-piperidin-1-yl]-acetamide | | |
| 61 | 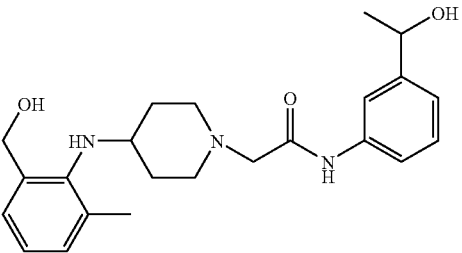 | N-[3-(1-Hydroxy-ethyl)-phenyl)-2-[4-(2-hydroxymethyl-6-methyl-phenylamino)-piperidin-1-yl]-acetamide | | |
| 62 | 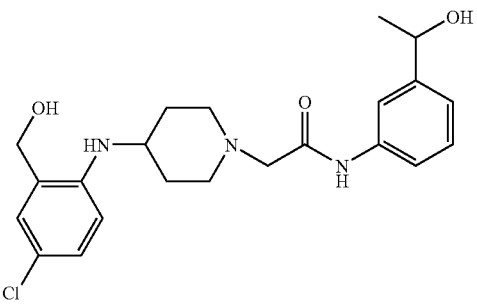 | 2-[4-(4-Chloro-2-hydroxymethyl-phenylamino)-piperidin-1-yl]-N-[3-(1-hydroxy-ethyl)-phenyl]-acetamide | | |

| N° | Structure | Name Autonom ® | MS APCI M + H⁺ | NMR |
|---|---|---|---|---|
| 63 | 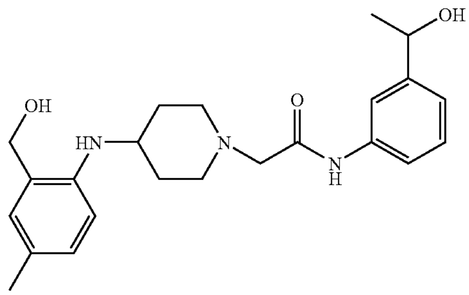 | N-[3-(1-Hydroxy-ethyl)-phenyl)-2-[4-(2-hydroxymethyl-4-methyl-phenylamino)-piperidin-1-yl]-acetamide | | |
| 64 | 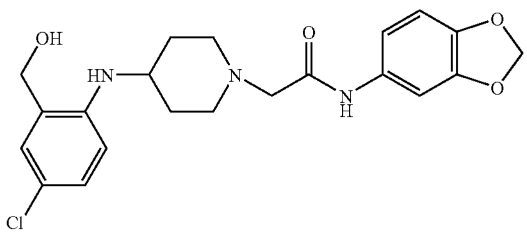 | N-Benzol[1,3]diox-ol-5-yl-2-[4-(4-chloro-2-hydroxymethyl-phenylamino)-piperidin-1-yl]-acetamide | | |
| 65 | 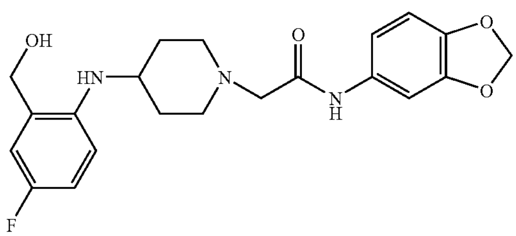 | N-Benzol[1,3]diox-ol-5-yl-2-[4-(4-fluoro-2-hydroxymethyl-phenylamino)-piperidin-1-yl]-acetamide | | |
| 66 | 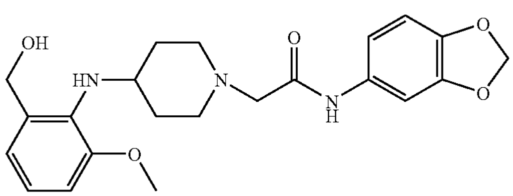 | N-Benzol[1,3]diox-ol-5-yl-2-[4-(2-hydroxymethyl-6-methoxy-phenylamino)-piperidin-1-yl]-acetamide | | |
| 67 | 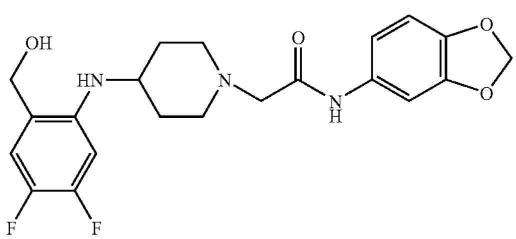 | N-Benzol[1,3]diox-ol-5-yl-2-[4-(4,5-difluoro-2-hydroxymethyl-phenylamino)-piperidin-1-yl]-acetamide | | |
| 68 | 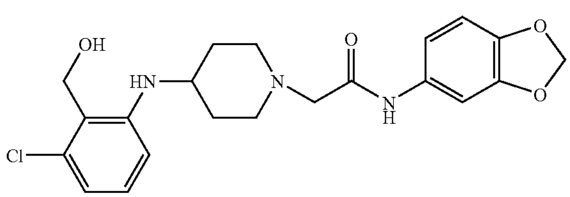 | N-Benzol[1,3]diox-ol-5-yl-2-[4-(3-chloro-2-hydroxymethyl-phenylamino)-piperidin-1-yl]-acetamide | | |

-continued

| N° | Structure | Name Autonom® | MS APCI M + H+ | NMR |
|---|---|---|---|---|
| 69 | 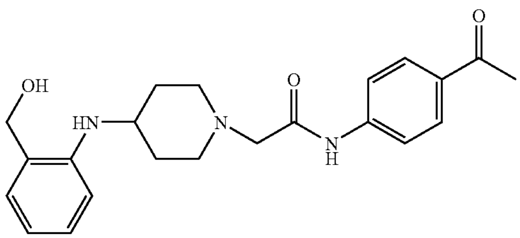 | N-(4-Acetyl-phenyl)-2-[4-(2-hydroxymethyl-phenylamino)-piperidin-1-yl]-acetamide | | |
| 70 | 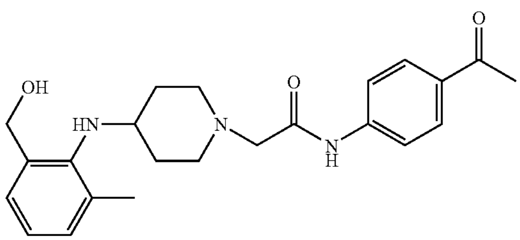 | N-(4-Acetyl-phenyl)-2-[4-(2-hydroxymethyl-6-methyl-phenylamino)-piperidin-1-yl]-acetamide | | |
| 71 | 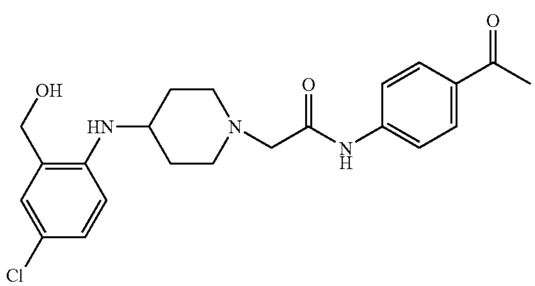 | N-(4-Acetyl-phenyl)-2-[4-(4-chloro-2-hydroxymethyl-phenylamino)-piperidin-1-yl]-acetamide | | |
| 72 | 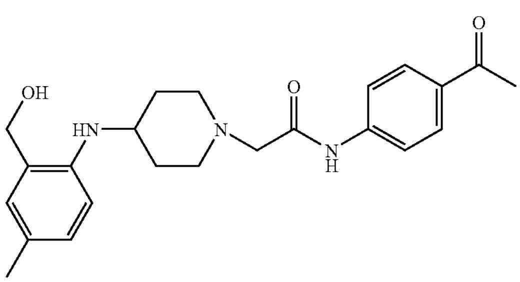 | N-(4-Acetyl-phenyl)-2-[4-(2-hydroxymethyl-4-methyl-phenylamino)-piperidin-1-yl]-acetamide | | |
| 73 | 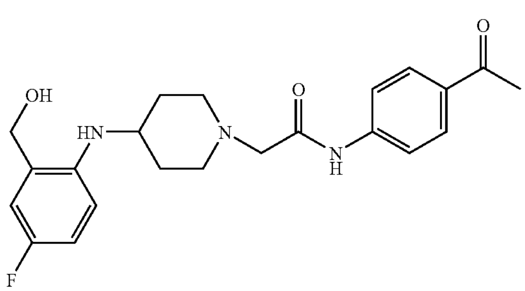 | N-(4-Acetyl-phenyl)-2-[4-(4-fluoro-2-hydroxymethyl-phenylamino)-piperidin-1-yl]-acetamide | | |

-continued

| N° | Structure | Name Autonom® | MS APCI M + H⁺ | NMR |
|---|---|---|---|---|
| 74 | 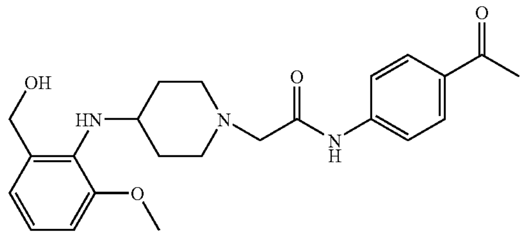 | N-(4-Acetyl-phenyl)-2-[4-(2-hydroxymethyl-6-methyl-phenylamino)-piperidin-1-yl]-acetamide | | |
| 75 | 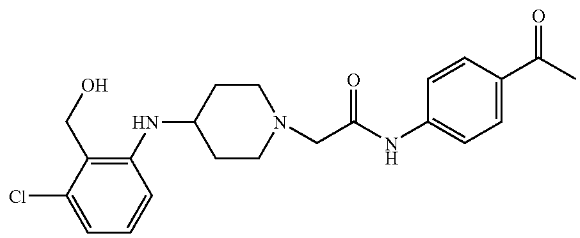 | N-(4-Acetyl-phenyl)-2-[4-(3-chloro-2-hydroxymethyl-phenylamino)-piperidin-1-yl]-acetamide | | |
| 76 | 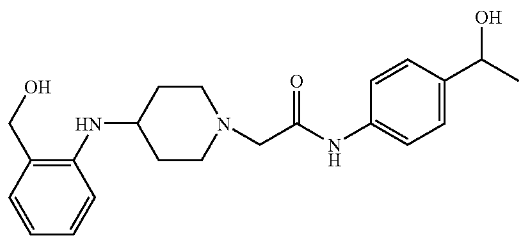 | N-[4-(1-Hydroxy-ethyl)-phenyl]-2-[4-(2-hydroxymethyl-phenylamino)-piperidin-1-yl]-acetamide | | |
| 77 | 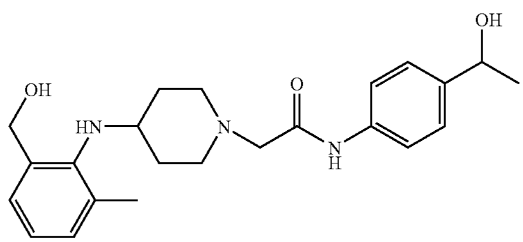 | N-[4-(1-Hydroxy-ethyl)-phenyl]-2-[4-(2-hydroxymethyl-6-methyl-phenylamino)-piperidin-1-yl]-acetamide | | |
| 78 | 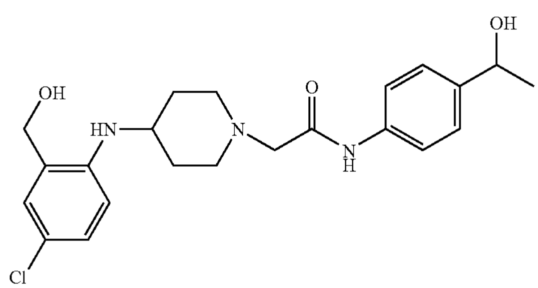 | 2-[4-(4-Chloro-2-hydroxymethyl-phenylamino)-piperidin-1-yl]-N-[4-(1-hydroxy-ethyl)-phenyl]-acetamide | | |
| 79 | 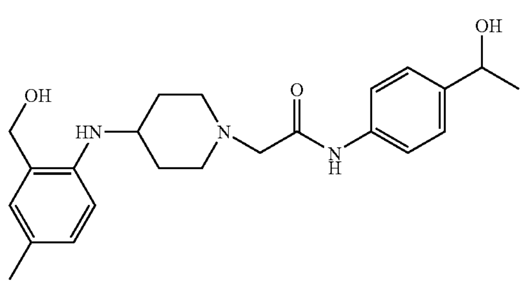 | N-[4-(1-Hydroxy-ethyl)-phenyl]-2-[4-(2-hydroxymethyl-4-methyl-phenylamino)-piperidin-1-yl]-acetamide | | |

-continued

| N° | Structure | Name Autonom ® | MS APCI M + H⁺ | NMR |
|---|---|---|---|---|
| 80 | 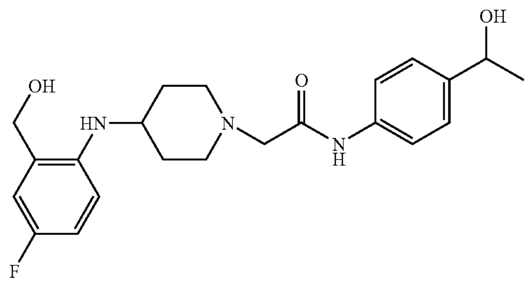 | 2-[4-(4-Fluoro-2-hydroxymethyl-phenylamino)-piperidin-1-yl-]N-[4-(1-hydroxy-ethyl)-phenyl]-acetamide | | |
| 81 | 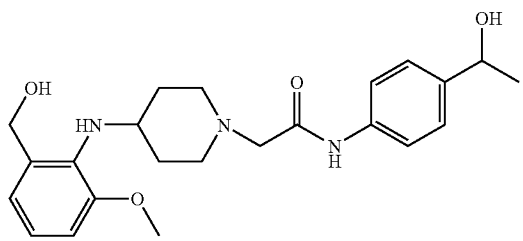 | N-[4-(1-Hydroxy-ethyl)-phenyl]-2-[4-(2-hydroxymethyl-6-methoxy-phenylamino)-piperidin-1-yl]-acetamide | | |
| 82 | 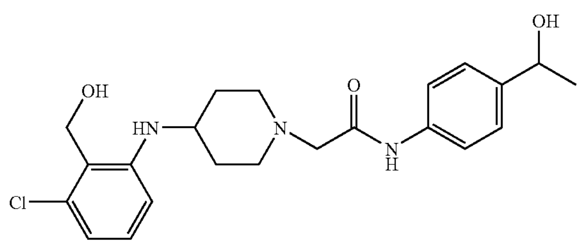 | 2-[4-(3-Chloro-2-hydroxymethyl-phenylamino)-piperidin-1-yl]-N-[4-(1-hydroxy-ethyl)-phenyl]-acetamide | | |
| 83 | 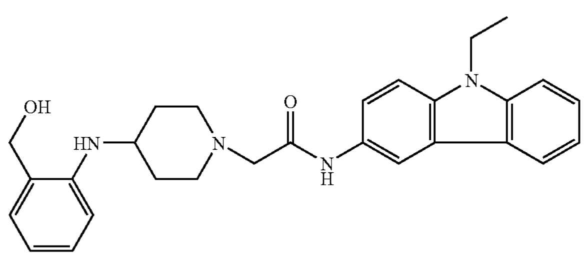 | N-(9-Ethyl-9H-carbazol-3-yl)-2-[4-(2-hydroxymethyl-phenylamino)-piperidin-1-yl]-acetamide | | |
| 84 | 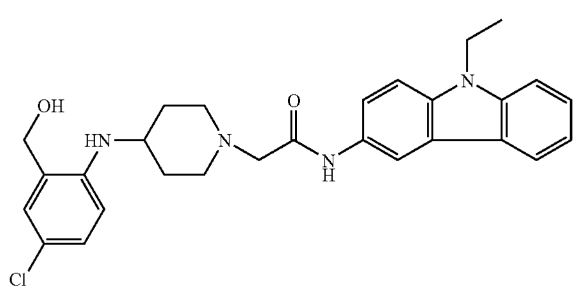 | 2-[4-(4-Chloro-2-hydroxymethyl-phenylamino)-piperidin-1-yl]-N-(9-ethyl-9H-carbazol-3-yl)-acetamide | | |

| N° | Structure | Name Autonom ® | MS APCI M + H+ | NMR |
|---|---|---|---|---|
| 85 | 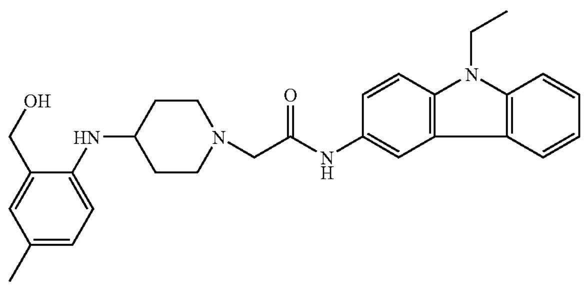 | N-(9-Ethyl-9H-carbazol-3-yl)-2-[4-(2-hydroxymethyl-4-methyl-phenylamino)-piperidin-1-yl]-acetamide | | |
| 86 | 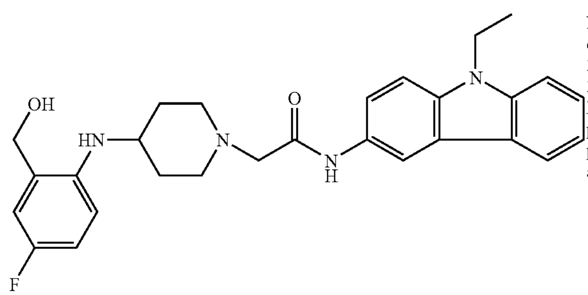 | N-(9-Ethyl-9H-carbazol-3-yl)-2-[4-(4-fluoro-2-hydroxymethyl-phenylamino)-piperidin-1-yl]-acetamide | | |
| 87 | 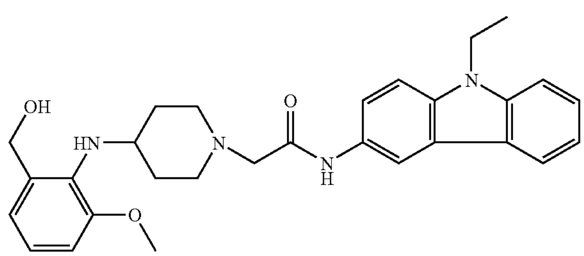 | N-(9-Ethyl-9H-carbazol-3-yl)-2-[4-(2-hydroxymethyl-6-methoxy-phenylamino)-piperidin-1-yl]-acetamide | | |
| 88 | 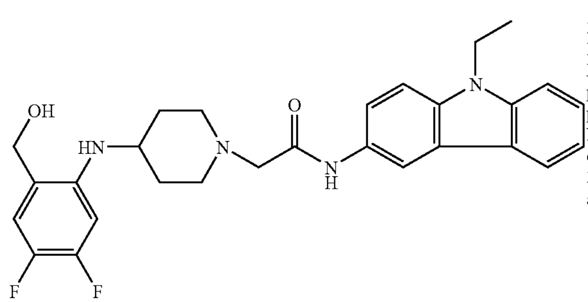 | 2-[4-(4,5-Difluoro-2-hydroxymethyl-phenylamino)-piperidin-1-yl]-N-(9-Ethyl-9H-carbazol-3-yl)-2-[4-(2-acetamide | | |
| 89 | 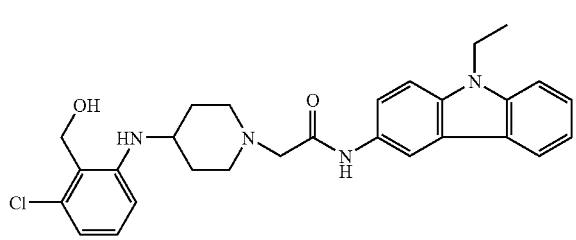 | 2-[4-(3-Chloro-2-hydroxymethyl-phenylamino)-piperidin-1-yl]-N-(9-ethyl-9H-carbazol-3-yl)-acetamide | | |

| N° | Structure | Name Autonom ® | MS APCI M + H+ | NMR |
|---|---|---|---|---|
| 90 | 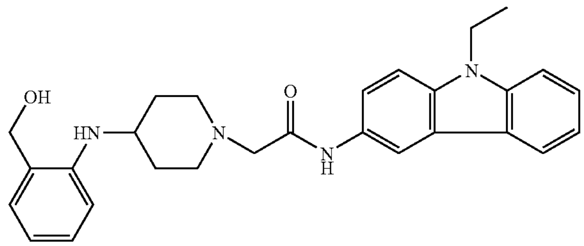 | 2-[4-(2-Hydroxymethyl-phenylamino)-piperidin-1-yl]-N-(9-methyl-9H-carbazol-3-yl)-acetamide | | |
| 91 | 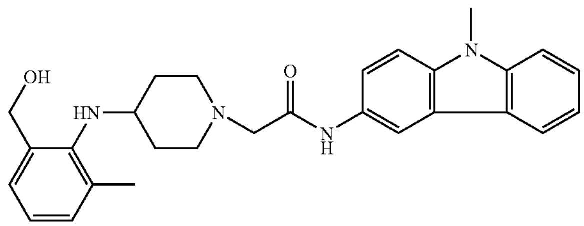 | 2-[4-(2-Hydroxymethyl-6-methyl-phenylamino)-piperidin-1-yl]-N-(9-methyl-9H-carbazol-3-yl)-acetamide | | |
| 92 | 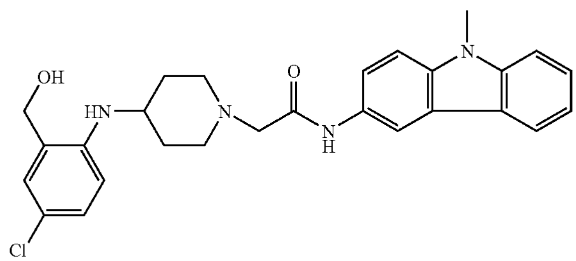 | 2-[4-(4-Chloro-2-hydroxymethyl-phenylamino)-piperidin-1-yl]-N-(9-methyl-9H-carbazol-3-yl)-acetamide | | |
| 93 | 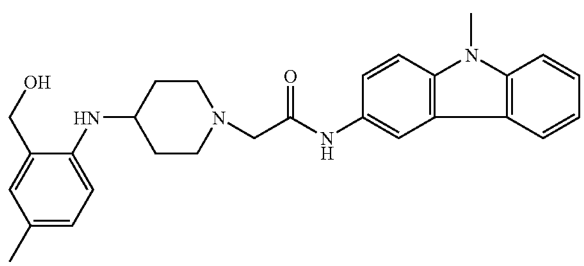 | 2-[4-(2-Hydroxymethyl-4-methyl-phenylamino)-piperidin-1-yl]-N-(9-methyl-9H-carbazol-3-yl)-acetamide | | |
| 94 | 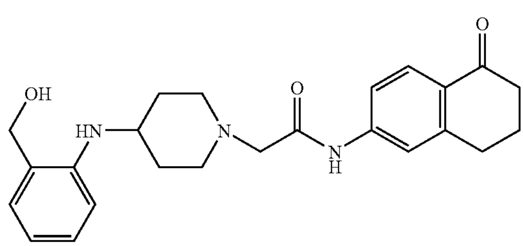 | 2-[4-(2-Hydroxymethyl-phenylamino)-piperidin-1-yl]-N-(5-oxo-5,6,7,8-tetrahydro-naphthalen-2-yl)-acetamide | | |
| 95 | 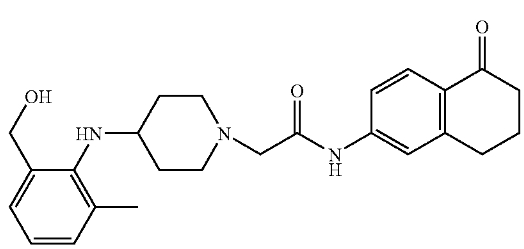 | 2-[4-(2-Hydroxymethyl-6-methyl-phenylamino)-piperidin-1-yl]-N-(5-oxo-5,6,7,8-tetrahydro-naphthalen-2-yl)-acetamide | | |

| N° | Structure | Name Autonom ® | MS APCI M + H⁺ | NMR |
|----|-----------|----------------|----------------|-----|
| 96 | 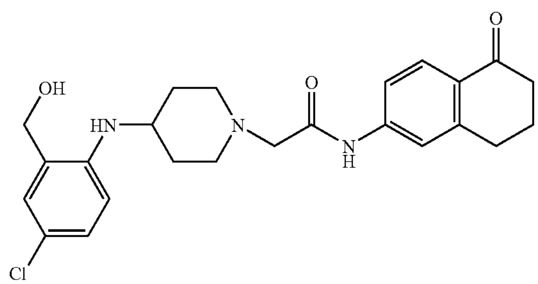 | 2-[4-(4-Chloro-2-hydroxymethyl-phenylamino)-piperidin-1-yl]-N-(5-oxo-5,6,7,8-tetrahydro-naphthalen-2-yl)-acetamide | | |
| 97 | 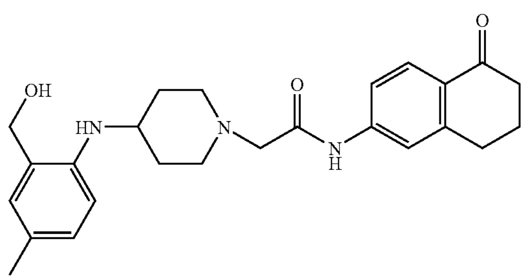 | 2-[4-(2-Hydroxymethyl-4-methyl-phenylamino)-piperidin-1-yl]-N-(5-oxo-5,6,7,8-tetrahydro-naphthalen-2-yl)-acetamide | | |
| 98 | 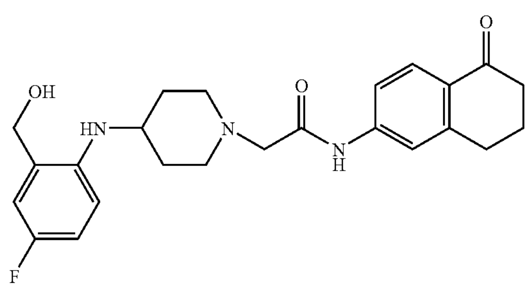 | 2-[4-(4-Fluoro-2-hydroxymethyl-phenylamino)-piperidin-1-yl]-N-(5-oxo-5,6,7,8-tetrahydro-naphthalen-2-yl)-acetamide | | |
| 99 | 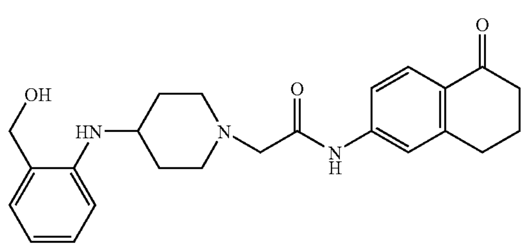 | 2-[4-(2-Hydroxymethyl-phenylamino)-piperidin-1-yl]-N-(5-hydroxy-5,6,7,8-tetrahydro-naphthalen-2-yl)-acetamide | | |
| 100 | 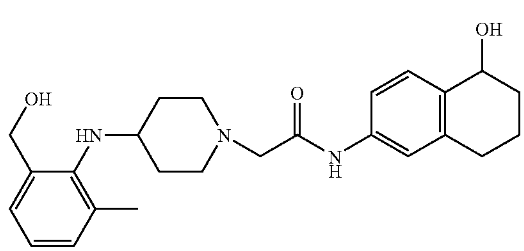 | 2-[4-(2-Hydroxymethyl-6-methyl-phenylamino)-piperidin-1-yl]-N-(5-hydroxy-5,6,7,8-tetrahydro-naphthalen-2-yl)-acetamide | | |

| N° | Structure | Name Autonom® | MS APCI M + H+ | NMR |
|---|---|---|---|---|
| 101 | 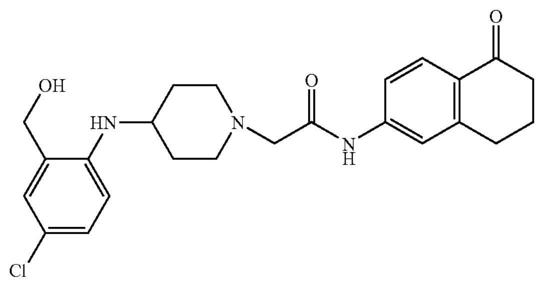 | 2-[4-(4-Chloro-2-hydroxymethyl-phenylamino)-piperidin-1-yl]-N-(5-hydroxy-5,6,7,8-tetrahydro-naphthalen-2-yl)-acetamide | | |
| 102 | 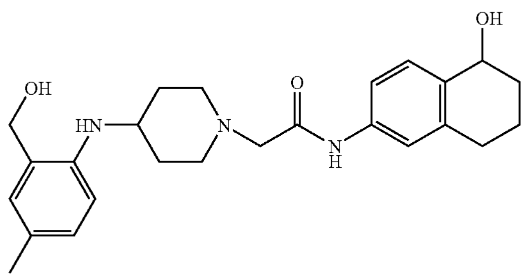 | 2-[4-(2-Hydroxymethyl-4-methyl-phenylamino)-piperidin-1-yl]-N-(5-hydroxy-5,6,7,8-tetrahydro-naphthalen-2-yl)-acetamide | | |
| 103 | 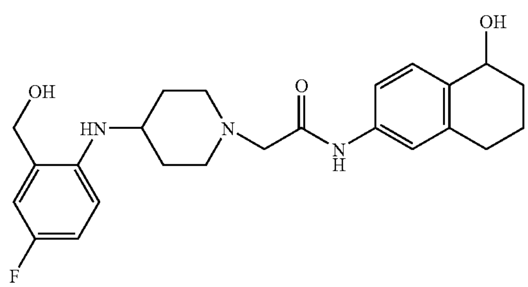 | 2-[4-(4-Fluoro-2-hydroxymethyl-phenylamino)-piperidin-1-yl]-N-(5-hydroxy-5,6,7,8-tetrahydro-naphthalen-2-yl)-acetamide | | |
| 104 | 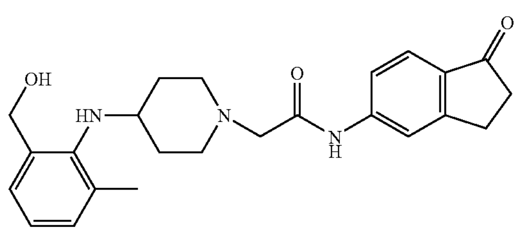 | 2-[4-(2-Hydroxymethyl-6-methyl-phenylamino)-piperidin-1-yl]-N-(1-oxo-indan-5-yl)-acetamide | | |
| 105 | 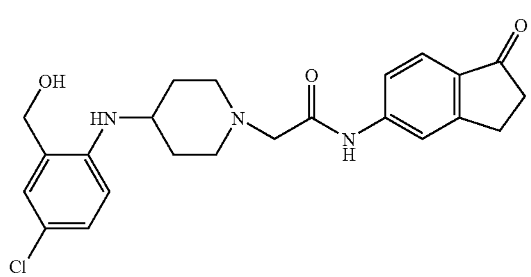 | 2-[4-(4-Chloro-2-hydroxymethyl-phenylamino)-piperidin-1-yl]-N-(1-oxo-indan-5-yl)-acetamide | | |

| N° | Structure | Name Autonom ® | MS APCI M + H⁺ | NMR |
|---|---|---|---|---|
| 106 | 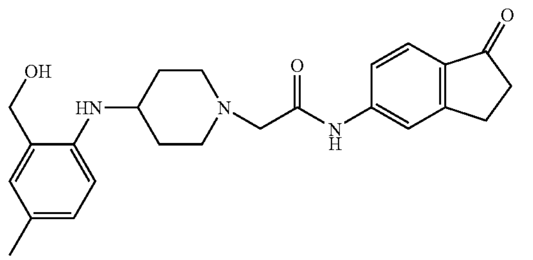 | 2-[4-(2-Hydroxymethyl-4-methyl-phenylamino)-piperidin-1-yl]-N-(1-oxo-indan-5-yl)-acetamide | | |
| 107 | 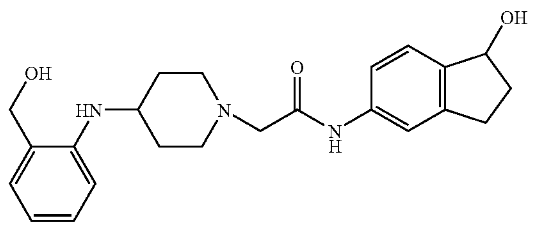 | N-(1-Hydroxy-indan-5-yl)-2-[4-(2-hydroxymethyl-phenylamino)-piperidin-1-yl]-acetamide | | |
| 108 | 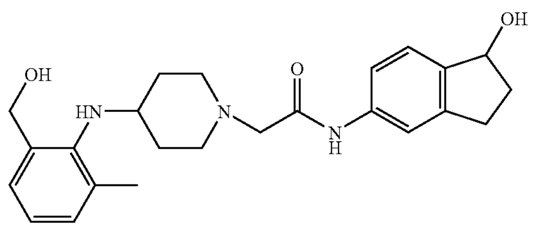 | N-(1-Hydroxy-indan-5-yl)-2-[4-(2-hydroxymethyl-6-methyl-phenylamino)-piperidin-1-yl]-acetamide | | |
| 109 | 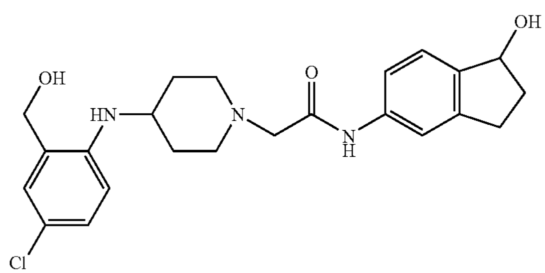 | 2-[4-(4-Chloro-2-hydroxymethyl-phenylamino)-piperidin-1-yl]-N-(1-hydroxy-indan-5-yl)-acetamide | | |
| 110 | 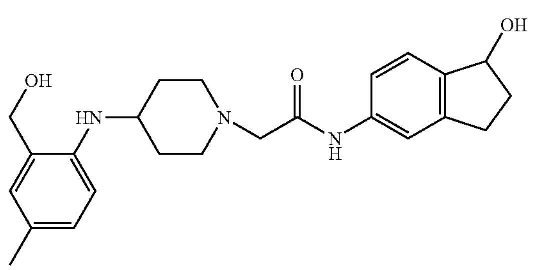 | N-(1-Hydroxy-indan-5-yl)-2-[4-(2-hydroxymethyl-4-methyl-phenylamino)-piperidin-1-yl]-acetamide | | |
| 111 | 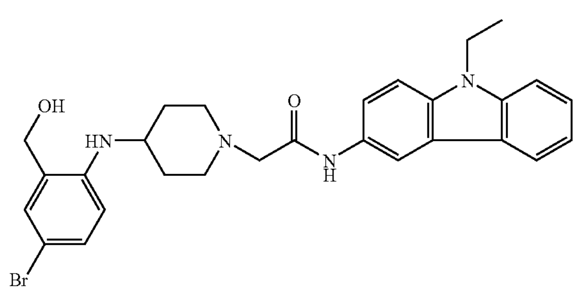 | 2-[4-(4-Bromo-2-hydroxymethyl-phenylamino)-piperidin-1-yl]-N-(9-ethyl-9H-carbazol-3-yl)-acetamide | | |

-continued

| N° | Structure | Name Autonom ® | MS APCI M + H⁺ | NMR |
|---|---|---|---|---|
| 112 | 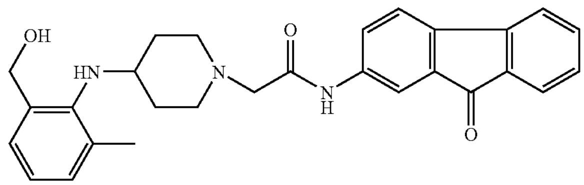 | 2-[4-(2-Hydroxymethyl-6-methyl-phenylamino)-piperidin-1-yl]-N-(9-oxo-9H-fluoren-2-yl)-acetamide | | |
| 113 | 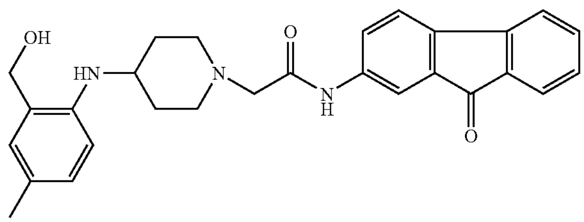 | 2-[4-(2-Hydroxymethyl-4-methyl-phenylamino)-piperidin-1-yl]-N-(9-oxo-9H-fluoren-2-yl)-acetamide | | |
| 114 | 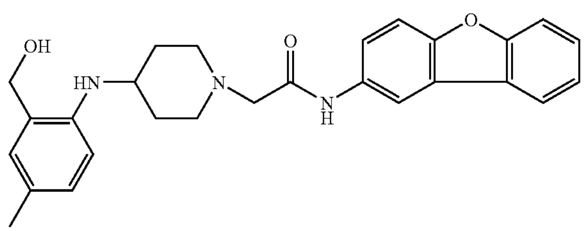 | N-Dibenzofuran-2-yl-2-[4-(2-hydroxymethyl-4-methyl-phenylamino)-piperidin-1-yl]-acetamide | | |
| 115 | 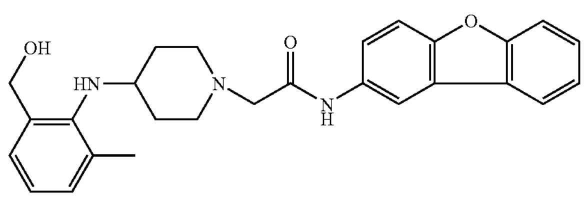 | N-Dibenzofuran-2-yl-2-[4-(2-hydroxymethyl-6-methyl-phenylamino)-piperidin-1-yl]-acetamide | | |
| 116 | 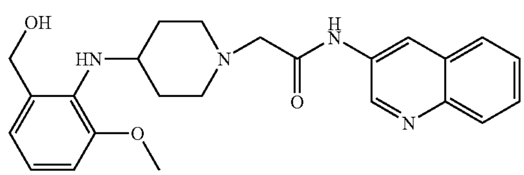 | 2-[4-(2-Hydroxymethyl-6-methyl-phenylamino)-piperidin-1-yl]-N-quinolin-3-yl-acetamide | | |
| 117 | 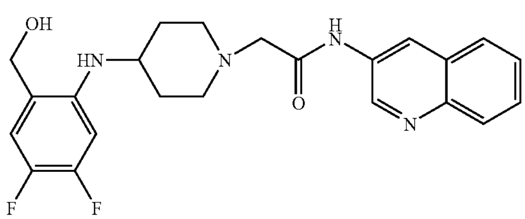 | 2-[4-(4-(4,5-Difluoro-2-hydroxymethyl-phenylamino)-piperidin-1-yl]-N-quinolin-3-yl-acetamide | | |
| 118 | 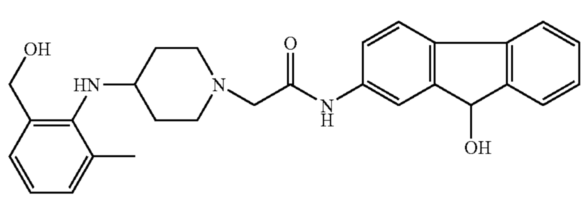 | N-(9-Hydroxy-9H-fluoren-2-yl)-2-[4-(2-hydroxymethyl-6-methyl-phenylamino)-piperidin-1-yl]-acetamide | | |

-continued

| N° | Structure | Name Autonom ® | MS APCI M + H⁺ | NMR |
|---|---|---|---|---|
| 119 | 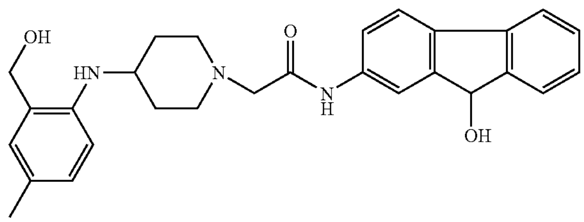 | N-(9-Hydroxy-9H-fluoren-2-yl)-2-[4-(2-hydroxymethyl-4-methyl-phenylamino)-piperidin-1-yl]-acetamide | | |
| 120 | 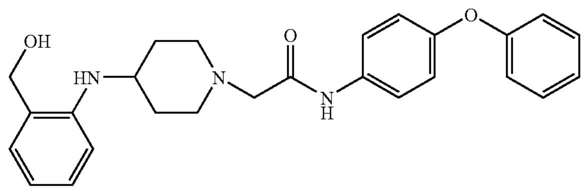 | 2-[4-(2-Hydroxymethyl-phenylamino)-piperidin-1-yl]-N-(4-phenoxy-phenyl)-acetamide | | |
| 121 | 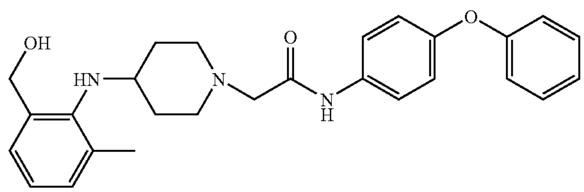 | 2-[4-(2-Hydroxymethyl-6-methyl-phenylamino)-piperidin-1-yl]-N-(4-phenoxy-phenyl)-acetamide | | |
| 122 | 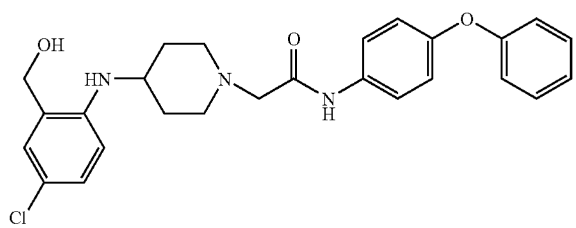 | 2-[4-(4-Chloro-2-hydroxymethyl-phenylamino)-piperidin-1-yl]-N-(4-phenoxy-phenyl)-acetamide | | |
| 123 | 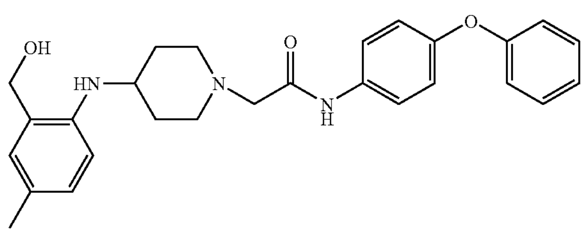 | 2-[4-(2-Hydroxymethyl-4-methyl-phenylamino)-piperidin-1-yl]-N-(4-phenoxy-phenyl)-acetamide | | |
| 124 | 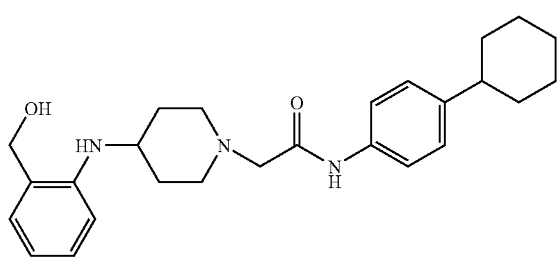 | N-(4-Cyclohexyl-phenyl)-2-[4-(2-hydroxymethyl-phenylamino)-piperidin-1-yl]-acetamide | | |
| 125 | 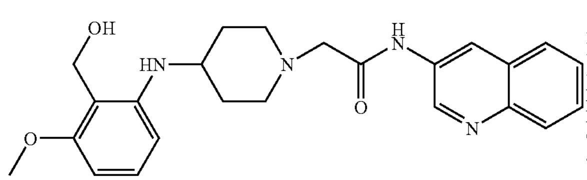 | 2-[4-(2-Hydroxymethyl-3-methoxy-phenylamino)-piperidin-1-yl]-N-quinolin-3-yl-acetamide | | |

-continued

| N° | Structure | Name Autonom ® | MS APCI M + H⁺ | NMR |
|---|---|---|---|---|
| 126 | 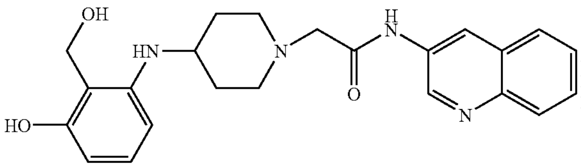 | 2-[4-(3-Hydroxy-2-hydroxymethyl-phenylamino)-piperidin-1-yl]-N-quinolin-3-yl-acetamide | | |
| 127 | 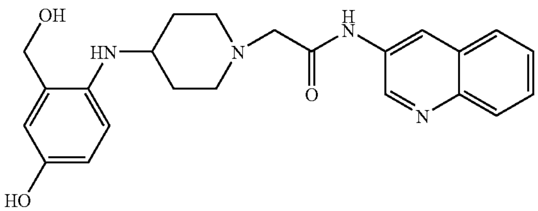 | 2-[4-(4-Hydroxy-2-hydroxymethyl-phenylamino)-piperidin-1-yl]-N-quinolin-3-yl-acetamide | | |
| 128 | 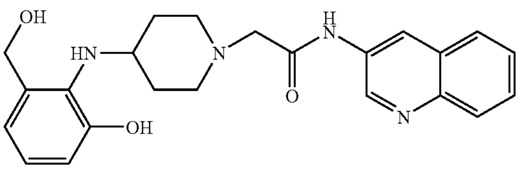 | 2-[4-(2-Hydroxy-6-hydroxymethyl-phenylamino)-piperidin-1-yl]-N-quinolin-3-yl-acetamide | | |
| 129 | 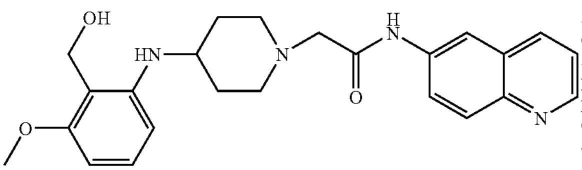 | 2-[4-(2-Hydroxymethyl-3-methoxy-phenylamino)-piperidin-1-yl]-N-quinolin-6-yl-acetamide | | |
| 130 | 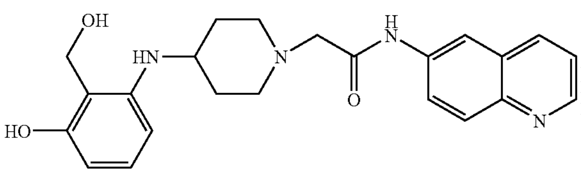 | 2-[4-(3-Hydroxy-2-hydroxymethyl-phenylamino)-piperidin-1-yl]-N-quinolin-6-yl-acetamide | | |
| 131 | 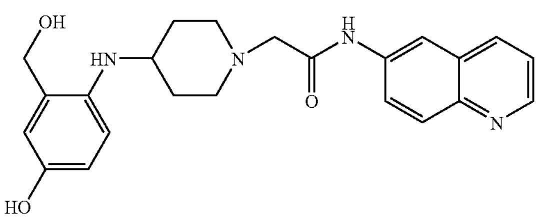 | 2-[4-(4-Hydroxy-2-hydroxymethyl-phenylamino)-piperidin-1-yl]-N-quinolin-6-yl-acetamide | | |
| 132 | 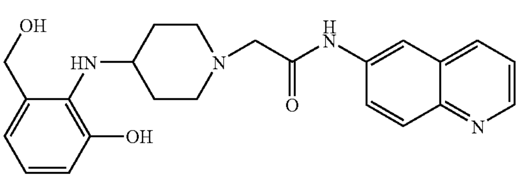 | 2-[4-(2-Hydroxy-6-hydroxymethyl-phenylamino)-piperidin-1-yl]-N-quinolin-6-yl-acetamide | | |
| 133 | 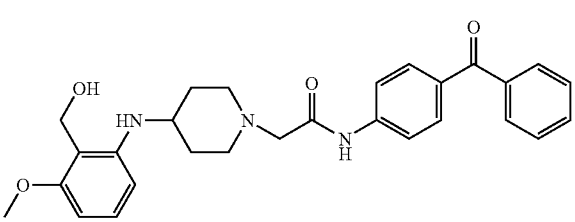 | N-(4-Benzoyl-phenyl)-2-[4-(2-hydroxymethyl-3-methoxy-phenylamino)-piperidin-1-yl]-acetamide | | |

| N° | Structure | Name Autonom ® | MS APCI M + H+ | NMR |
|---|---|---|---|---|
| 134 | 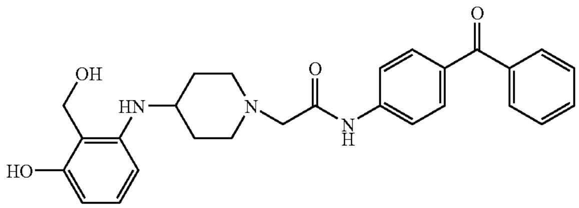 | N-(4-Benzoyl-phenyl)-2-[4-(3-hydroxy-2-hydroxymethyl-phenylamino)-piperidin-1-yl]-acetamide | | |
| 135 | 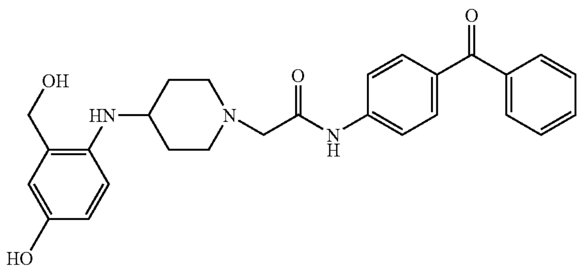 | N-(4-Benzoyl-phenyl)-2-[4-(4-hydroxy-2-hydroxymethyl-phenylamino)-piperidin-1-yl]-acetamide | | |
| 136 | 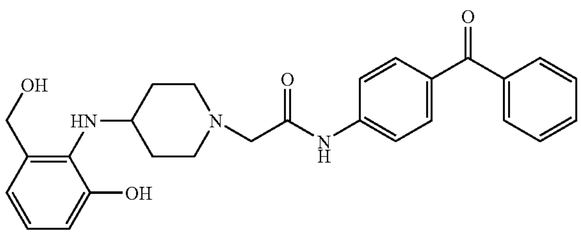 | N-(4-Benzoyl-phenyl)-2-[4-(2-hydroxy-6-hydroxymethyl-phenylamino)-piperidin-1-yl]-acetamide | | |
| 137 | 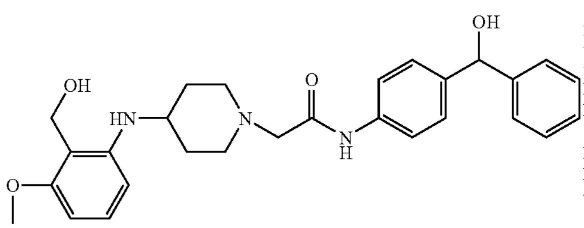 | 2-[4-(2-Hydroxymethyl-3-methoxy-phenylamino)-piperidin-1-yl]-N-[4-(hydroxy-phenyl-methyl)-phenyl]-acetamide | | |
| 138 | 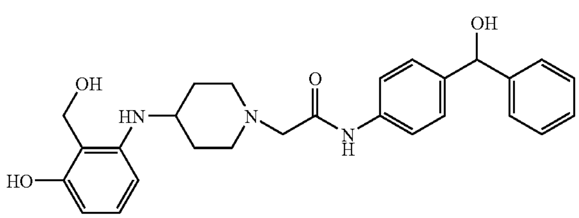 | 2-[4-(3-Hydroxy-2-hydroxymethyl-phenylamino)-piperidin-1-yl]-N-[4-(hydroxy-phenyl-methyl)-phenyl]-acetamide | | |
| 139 | 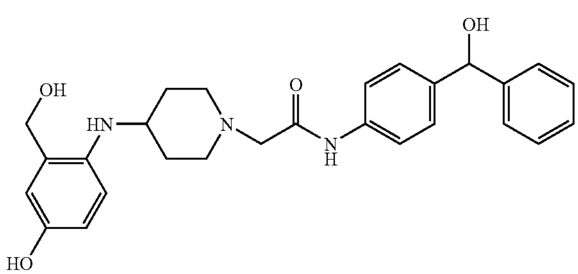 | 2-[4-(4-Hydroxy-2-hydroxymethyl-phenylamino)-piperidin-1-yl]-N-[4-(hydroxy-phenyl-methyl)-phenyl]-acetamide | | |

| N° | Structure | Name Autonom ® | MS APCI M + H⁺ | NMR |
|---|---|---|---|---|
| 140 | 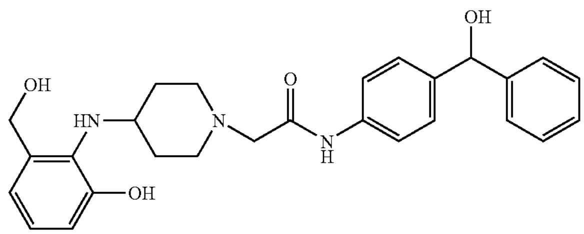 | 2-[4-(2-Hydroxy-6-hydroxymethyl-phenylamino)-piperidin-1-yl]-N-[4-(hydroxy-phenyl-methyl)-phenyl]-acetamide | | |
| 141 | 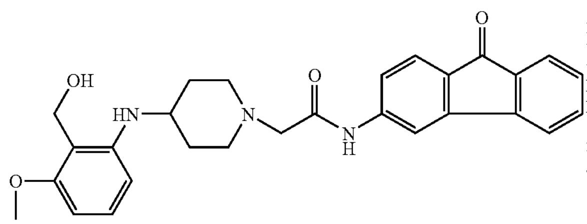 | 2-[4-(2-Hydroxymethyl-3-methoxy-phenylamino)-piperidin-1-yl]-N-(9-oxy-9H-fluoren-3-yl)-acetamide | | |
| 142 | 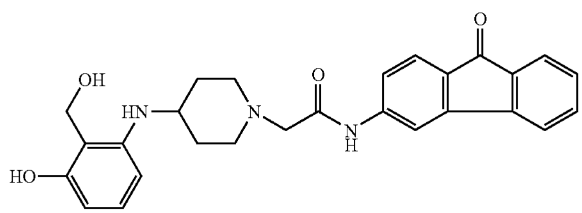 | 2-[4-(3-Hydroxy-2-hydroxymethyl-phenylamino)-piperidin-1-yl]-N-(9-oxy-9H-fluoren-3-yl)-acetamide | | |
| 143 | 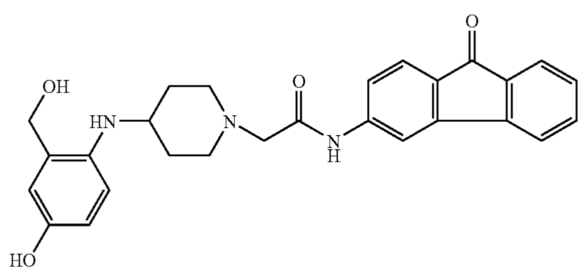 | 2-[4-(4-Hydroxy-2-hydroxymethyl-phenylamino)-piperidin-1-yl]-N-(9-oxy-9H-fluoren-3-yl)-acetamide | | |
| 144 | 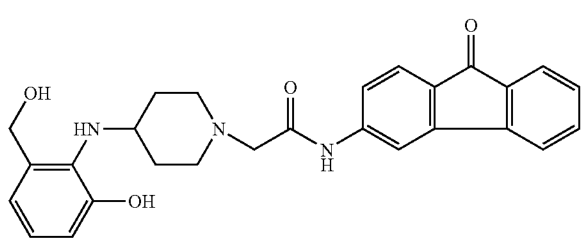 | 2-[4-(2-Hydroxy-6-hydroxymethyl-phenylamino)-piperidin-1-yl]-N-(9-oxy-9H-fluoren-3-yl)-acetamide | | |
| 145 | 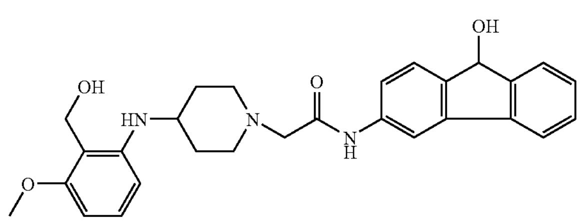 | N-(9-Hydroxy-9H-fluoren-3-yl)-2-[4-(2-hydroxymethyl-3-methoxy-phenylamino)-piperidin-1-yl]-acetamide | | |

-continued

| N° | Structure | Name Autonom ® | MS APCI M + H⁺ | NMR |
|---|---|---|---|---|
| 146 | 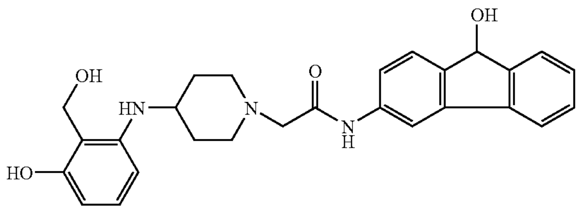 | N-(9-Hydroxy-9H-fluoren-3-yl)-2-[4-(3-hydroxy-2-hydroxymethyl-phenylamino)-piperidin-1-yl]-acetamide | | |
| 147 | 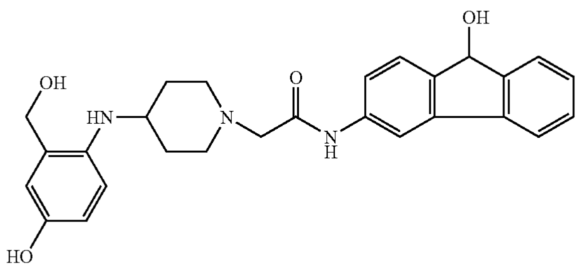 | N-(9-Hydroxy-9H-fluoren-3-yl)-2-[4-(4-hydroxy-2-hydroxymethyl-phenylamino)-piperidin-1-yl]-acetamide | | |
| 148 | 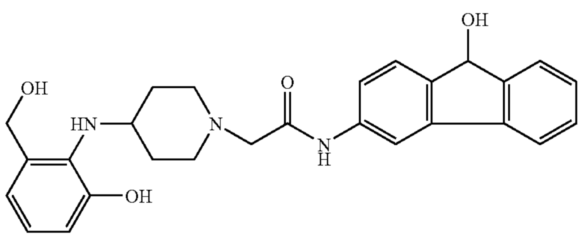 | N-(9-Hydroxy-9H-fluoren-3-yl)-2-[4-(2-hydroxy-6-hydroxymethyl-phenylamino)-piperidin-1-yl]-acetamide | | |
| 149 | 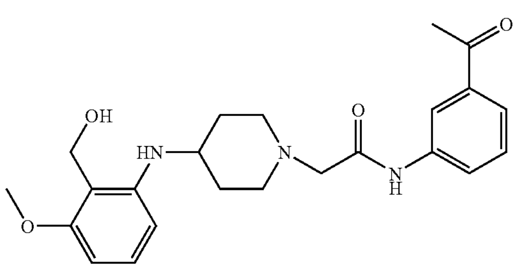 | N-(3-Acetyl-phenyl)-2-[4-(2-hydroxymethyl-3-methoxy-phenylamino)-piperidin-1-yl]-acetamide | | |
| 150 | 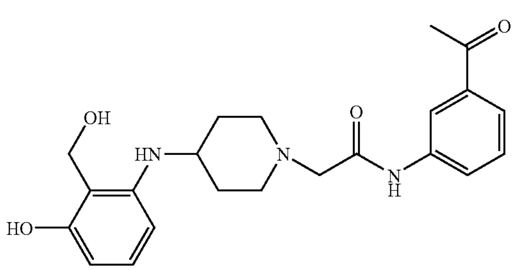 | N-(3-Acetyl-phenyl)-2-[4-(3-hydroxy-2-hydroxymethyl-phenylamino)-piperidin-1-yl]-acetamide | | |

-continued

| N° | Structure | Name Autonom® | MS APCI M + H⁺ | NMR |
|---|---|---|---|---|
| 151 | 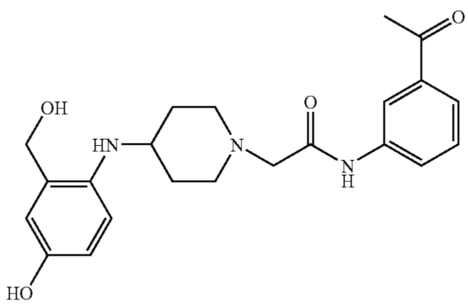 | N-(3-Acetyl-phenyl)-2-[4-(4-hydroxy-2-hydroxymethyl-phenylamino)-piperidin-1-yl]-acetamide | | |
| 152 | 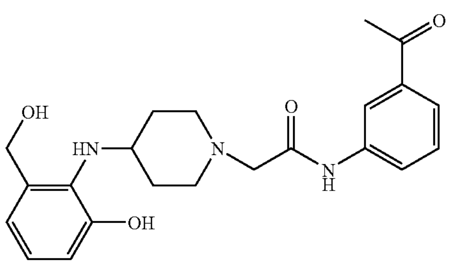 | N-(3-Acetyl-phenyl)-2-[4-(2-hydroxy-6-hydroxymethyl-phenylamino)-piperidin-1-yl]-acetamide | | |
| 153 | 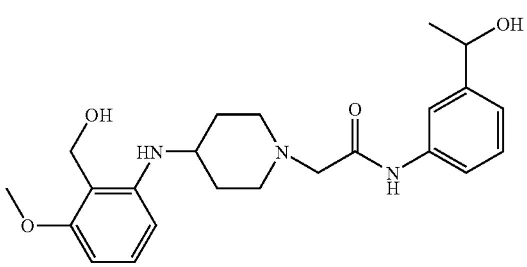 | N-[3-(1-Hydroxy-ethyl)-phenyl]-2-[4-(2-hydroxymethyl-3-methoxy-phenylamino)-piperidin-1-yl]-acetamide | | |
| 154 | 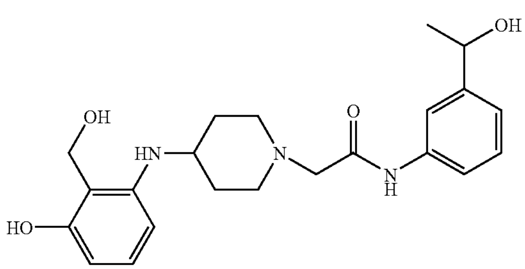 | N-[3-(1-Hydroxy-ethyl)-phenyl]-2-[4-(3-hydroxy-2-hydroxymethyl-phenylamino)-piperidin-1-yl]-acetamide | | |
| 155 | 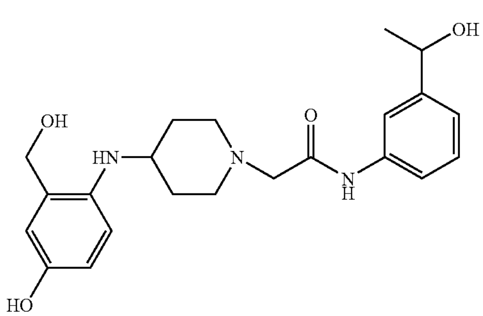 | N-[3-(1-Hydroxy-ethyl)-phenyl]-2-[4-(4-hydroxy-2-hydroxymethyl-phenylamino)-piperidin-1-yl]-acetamide | | |

-continued

| N° | Structure | Name Autonom ® | MS APCI M + H⁺ | NMR |
|---|---|---|---|---|
| 156 | 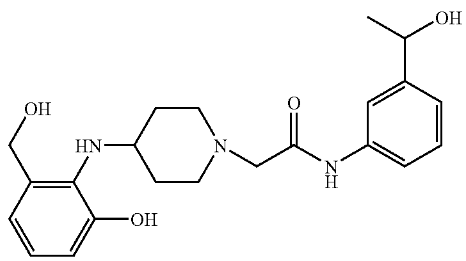 | N-[3-(1-Hydroxy-ethyl)-phenyl]-2-[4-(2-hydroxy-6-hydroxymethyl-phenylamino)-piperidin-1-yl]-acetamide | | |
| 157 | 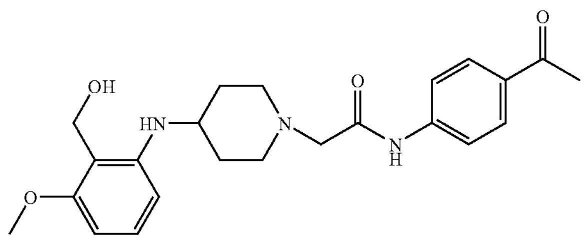 | N-(4-Acetyl-phenyl)-2-[4-(2-hydroxymethyl-3-methoxy-phenylamino)-piperidin-1-yl]-acetamide | | |
| 158 | 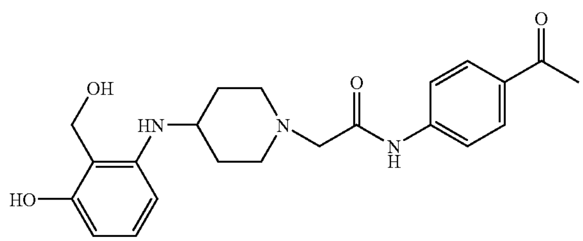 | N-(4-Acetyl-phenyl)-2-[4-(3-hydroxy-2-hydroxymethyl-phenylamino)-piperidin-1-yl]-acetamide | | |
| 159 | 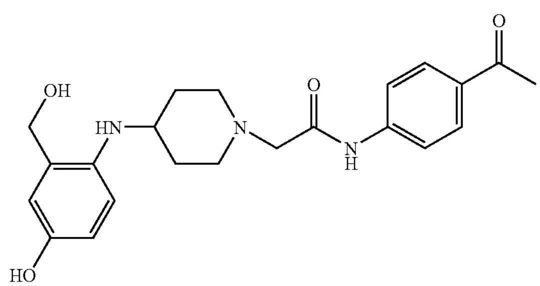 | N-(4-Acetyl-phenyl)-2-[4-(4-hydroxy-2-hydroxymethyl-phenylamino)-piperidin-1-yl]-acetamide | | |
| 160 | 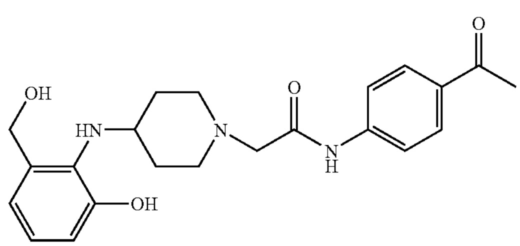 | N-(4-Acetyl-phenyl)-2-[4-(2-hydroxy-6-hydroxymethyl-phenylamino)-piperidin-1-yl]-acetamide | | |
| 161 | 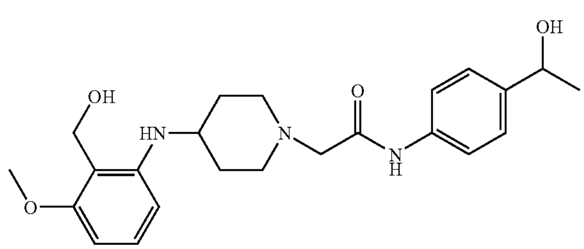 | N-[4-(1-Hydroxy-ethyl)-phenyl]-2-[4-(2-hydroxymethyl-3-methoxy-phenylamino)-piperidin-1-yl]-acetamide | | |

| N° | Structure | Name Autonom ® | MS APCI M + H⁺ | NMR |
|---|---|---|---|---|
| 162 | 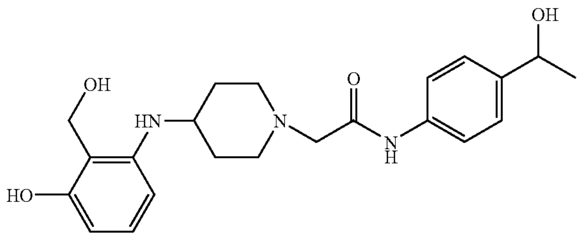 | N-[4-(1-Hydroxy-ethyl)-phenyl]-2-[4-(3-hydroxy-2-hydroxymethyl-phenylamino)-piperidin-1-yl]-acetamide | | |
| 163 | 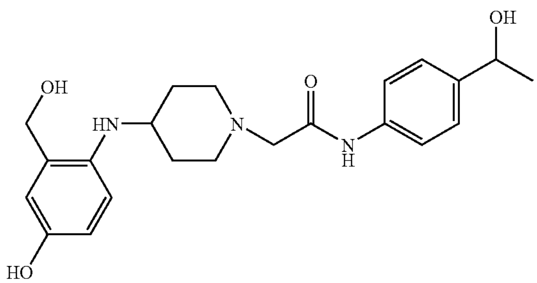 | N-[4-(1-Hydroxy-ethyl)-phenyl]-2-[4-(4-hydroxy-2-hydroxymethyl-phenylamino)-piperidin-1-yl]-acetamide | | |
| 164 | 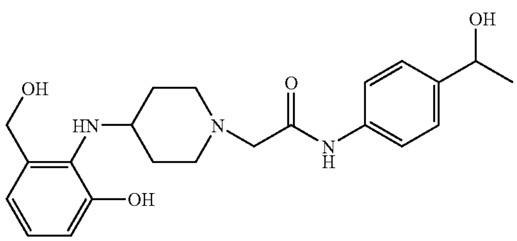 | N-[4-(1-Hydroxy-ethyl)-phenyl]-2-[4-(2-hydroxy-6-hydroxymethyl-phenylamino)-piperidin-1-yl]-acetamide | | |
| 165 | 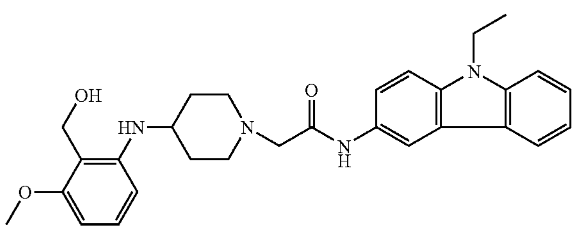 | N-(9-Ethyl-9H-carbazol-3-yl)-2-[4-(2-hydroxymethyl-3-methoxy-phenylamino)-piperidin-1-yl]-acetamide | | |
| 166 | 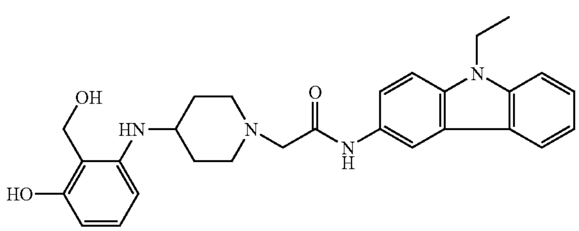 | N-(9-Ethyl-9H-carbazol-3-yl)-2-[4-(3-hydroxy-2-hydroxymethyl-phenylamino)-piperidin-1-yl]-acetamide | | |
| 167 | 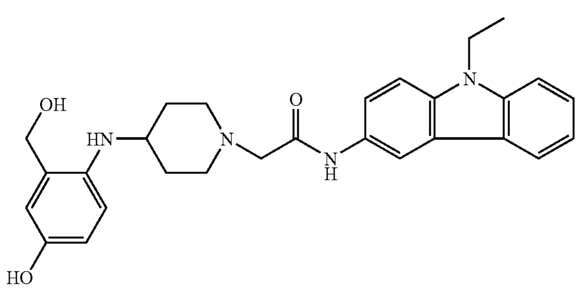 | N-(9-Ethyl-9H-carbazol-3-yl)-2-[4-(4-hydroxy-2-hydroxymethyl-phenylamino)-piperidin-1-yl]-acetamide | | |

| N° | Structure | Name Autonom ® | MS APCI M + H⁺ | NMR |
|---|---|---|---|---|
| 168 | 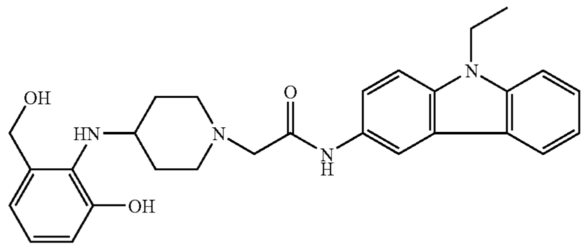 | N-(9-Ethyl-9H-carbazol-3-yl)-2-[4-(2-hydroxy-6-hydroxymethyl-phenylamino)-piperidin-1-yl]-acetamide | | |
| 169 | 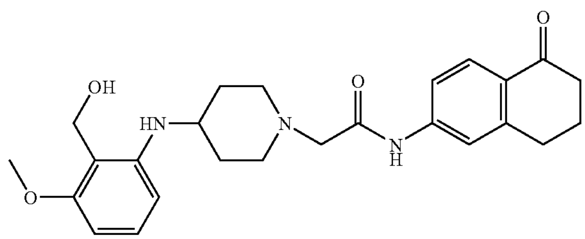 | 2-[4-(2-Hydroxymethyl-3-methoxy-phenylamino)-piperidin-1-yl]-N-(5-oxo-5,6,7,8-tetrahydro-naphthalen-2-yl)-acetamide | | |
| 170 | 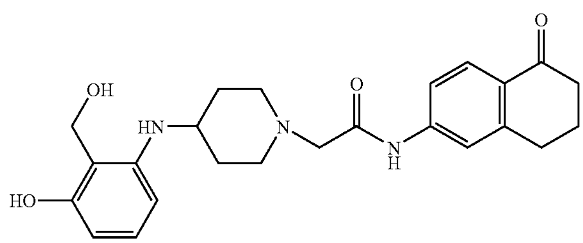 | 2-[4-(3-Hydroxy-2-hydroxymethyl-phenylamino)-piperidin-1-yl]-N-(5-oxo-5,6,7,8-tetrahydro-naphthalen-2-yl)-acetamide | | |
| 171 | 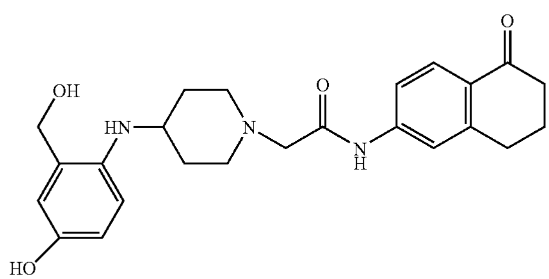 | 2-[4-(4-Hydroxy-2-hydroxymethyl-phenylamino)-piperidin-1-yl]-N-(5-oxo-5,6,7,8-tetrahydro-naphthalen-2-yl)-acetamide | | |
| 172 | 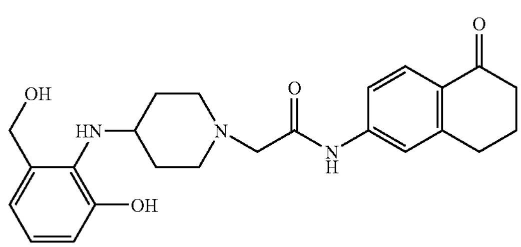 | 2-[4-(2-Hydroxy-6-hydroxymethyl-phenylamino)-piperidin-1-yl]-N-(5-oxo-5,6,7,8-tetrahydro-naphthalen-2-yl)-acetamide | | |
| 173 | 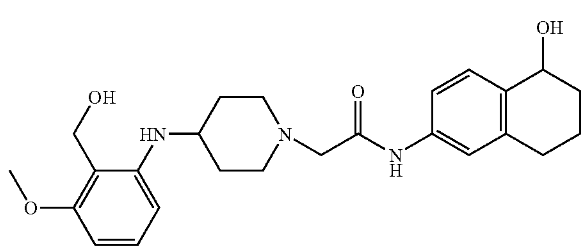 | 2-[4-(2-Hydroxymethyl-3-methoxy-phenylamino)-piperidin-1-yl]-N-(5-hydroxy-5,6,7,8-tetrahydro-naphthalen-2-yl)-acetamide | | |

-continued

| N° | Structure | Name Autonom® | MS APCI M + H⁺ | NMR |
|---|---|---|---|---|
| 174 | 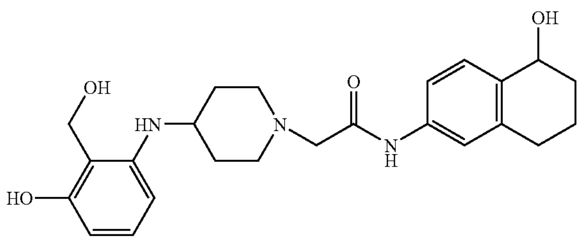 | 2-[4-(3-Hydroxy-2-hydroxymethyl-phenylamino)-piperidin-1-yl]-N-(5-hydroxy-5,6,7,8-tetrahydro-naphthalen-2-yl)-acetamide | | |
| 175 | 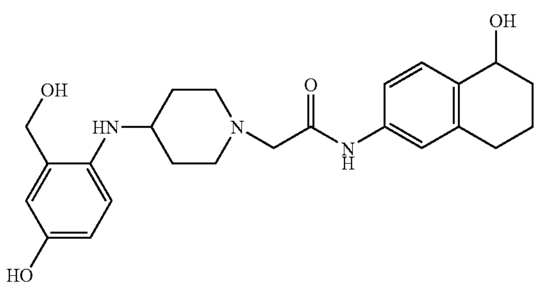 | 2-[4-(4-Hydroxy-2-hydroxymethyl-phenylamino)-piperidin-1-yl]-N-(5-hydroxy-5,6,7,8-tetrahydro-naphthalen-2-yl)-acetamide | | |
| 176 | 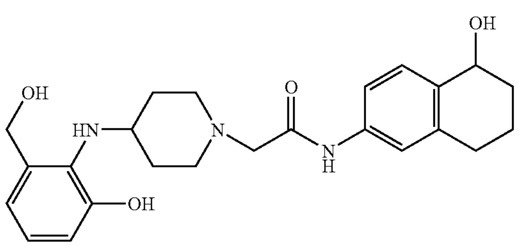 | 2-[4-(2-Hydroxy-6-hydroxymethyl-phenylamino)-piperidin-1-yl]-N-(5-hydroxy-5,6,7,8-tetrahydro-naphthalen-2-yl)-acetamide | | |
| 177 | 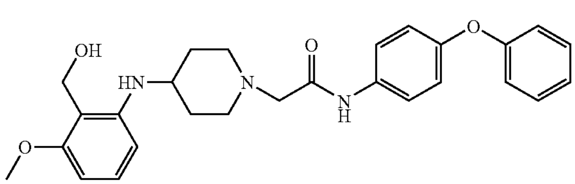 | 2-[4-(2-Hydroxymethyl-3-methoxy-phenylamino)-piperidin-1-yl]-N-(4-phenoxy-phenyl)-acetamide | | |
| 178 | 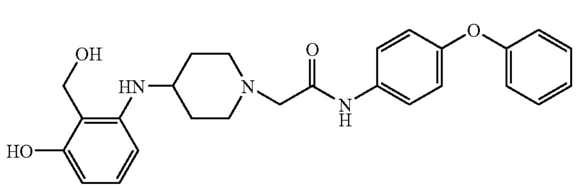 | 2-[4-(3-Hydroxy-2-hydroxymethyl-phenylamino)-piperidin-1-yl]-N-(4-phenoxy-phenyl)-acetamide | | |

-continued

| N° | Structure | Name Autonom® | MS APCI M + H⁺ | NMR |
|---|---|---|---|---|
| 179 | 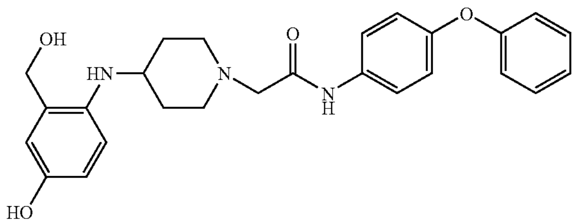 | 2-[4-(4-Hydroxy-2-hydroxymethyl-phenylamino)-piperidin-1-yl]-N-(4-phenoxy-phenyl)-acetamide | | |
| 180 | 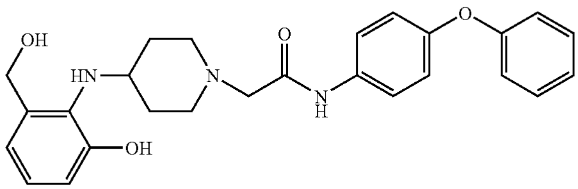 | 2-[4-(2-Hydroxy-6-hydroxymethyl-phenylamino)-piperidin-1-yl]-N-(4-phenoxy-phenyl)-acetamide | | |

Pharmacological Data:

(a)

According to the methods given above Neuropeptide $Y_5$ and $Y_2$ Binding of the 1,4-disubstituted piperidine compounds of general formula (I) has been determined. Some of the $Y_5$ values are given in the following tables 1 and 2.

TABLE 1

| Compound according to Example | Neuropeptide $Y_5$ Binding IC50 (nm) |
|---|---|
| 1a | 50 |
| 2a | 80.9 |
| 3a | 36.3 |
| 5a | 40.1 |

TABLE 2

| Compound according to example | Binding of Neuropeptide $Y_5$ % Inhibition $10^{-6}$ M |
|---|---|
| 5 | 86.2 |
| 7 | 82.3 |
| 9 | 80.4 |
| 11 | 73.9 |
| 13 | 81.5 |
| 14 | 88.9 |
| 15 | 93.2 |

What is claimed is:

1. A 1,4-disubstituted piperidine compounds of general formula (I), wherein

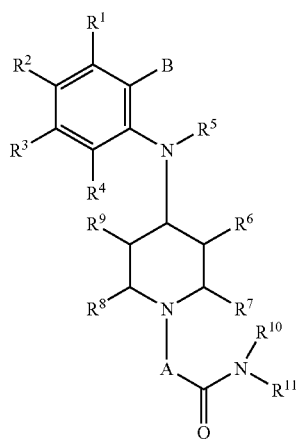

(I)

$R^1$, $R^2$, $R^3$, $R^4$ are each independently selected from the group consisting of H, F, Cl, Br, OH, $CH_3$, and $OCH_3$, B represents a —$CH_2$—OH or —(C=O)—O—$CH_3$ group, $R^{11}$ is selected from the group consisting of unsubstituted phenyl, phenyl that is optionally at least mono-substituted with one or more substituents independently selected from the group consisting of cyclohexyl, phenyl, phenoxy, benzoyl, —C(=O)—$C_{1-2}$-alkyl, —C(H)(OH)(phenyl) and —C(H)(OH)($CH_3$), a group of formula (A)

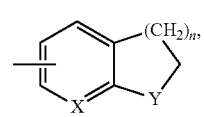

(A)

wherein
n is 1 or 2,
X represents CH,
Y represents CH—OH or C(=O),
a group of formula (B),

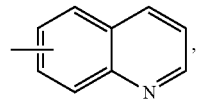
(B)

a group of formula (C),

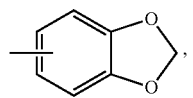
(C)

and a group of formula (E),

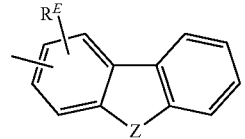
(E)

wherein
$R^E$ represents H, a branched or unbranched $C_{1-4}$-alkyl radical or a branched or unbranched $C_{1-4}$-alkoxy radical,
Z represents $CH_2$, O, S, CH—OH, C(=O) or N—$R^F$ where $R^F$ represents H or a branched or unbranched $C_{1-4}$-alkyl-radical,
optionally in form of one of its stereoisomers, its racemate or in form of a mixture of at least two of its stereoisomers, or a salt.

2. The compound according to claim 1 selected from the group consisting of:

| N° | |
|---|---|
| 1 | 2-[4-(2-Hydroxymethyl-phenylamino)-piperidin-1-yl]-N-quinolin-3-yl-acetamide |
| 2 | 2-[4-(2-Hydroxymethyl-phenylamino)-piperidin-1-yl]-N-quinolin-5-yl-acetamide |
| 3 | 2-[4-(2-Hydroxymethyl-phenylamino)-piperidin-1-yl]-N-quinolin-6-yl-acetamide |
| 4 | 2-[4-(2-Hydroxymethyl-phenylamino)-piperidin-1-yl]-N-quinolin-8-yl-acetamide |
| 5 | 2-[4-(2-Hydroxymethyl-4-methyl-phenylamino)-piperidin-1-yl]-N-quinolin-3-yl-acetamide |
| 6 | 2-[4-(2-Hydroxymethyl-4-methyl-phenylamino)-piperidin-1-yl]-N-quinolin-5-yl-acetamide |
| 7 | 2-[4-(2-Hydroxymethyl-4-methyl-phenylamino)-piperidin-1-yl]-N-quinolin-6-yl-acetamide |
| 8 | 2-[4-(2-Hydroxymethyl-4-methyl-phenylamino)-piperidin-1-yl]-N-quinolin-8-yl-acetamide |
| 9 | 2-[4-(2-Hydroxymethyl-6-methyl-phenylamino)-piperidin-1-yl]-N-quinolin-3-yl-acetamide |
| 10 | 2-[4-(2-Hydroxymethyl-6-methyl-phenylamino)-piperidin-1-yl]-N-quinolin-5-yl-acetamide |
| 11 | 2-[4-(2-Hydroxymethyl-6-methyl-phenylamino)-piperidin-1-yl]-N-quinolin-6-yl-acetamide |
| 12 | 2-[4-(2-Hydroxymethyl-6-methyl-phenylamino)-piperidin-1-yl]-N-quinolin-8-yl-acetamide |
| 13 | N-(4-Benzoyl-phenyl)-2-[4-(2-hydroxymethyl-phenylamino)-piperidin-1-yl]-acetamide |
| 14 | N-(4-Benzoyl-phenyl)-2-[4-(2-hydroxymethyl-4-methyl-phenylamino)-piperidin-1-yl]-acetamide |
| 15 | N-(4-Benzoyl-phenyl)-2-[4-(2-hydroxymethyl-6-methyl-phenylamino)-piperidin-1-yl]-acetamide |
| 16 | N-Benzo[1,3]dioxol-5-yl-2-[4-(2-hydroxymethyl-phenylamino)-piperidin-1-yl]-acetamide |
| 17 | N-Benzo[1,3]dioxol-5-yl-2-[4-(2-hydroxymethyl-4-methyl-phenylamino)-piperidin-1-yl]-acetamide |
| 18 | N-Benzo[1,3]dioxol-5-yl-2-[4-(2-hydroxymethyl-6-methyl-phenylamino)-piperidin-1-yl]-acetamide hydrochloride |
| 19 | 2-[4-(4-Chloro-2-hydroxymethyl-phenylamino)-piperidin-1-yl]-N-quinolin-3-yl-acetamide |
| 20 | 2-[4-(4-Fluoro-2-hydroxymethyl-phenylamino)-piperidin-1-yl]-N-quinolin-3-yl-acetamide |
| 21 | 2-[4-(3-Chloro-2-hydroxymethyl-phenylamino)-piperidin-1-yl]-N-quinolin-3-yl-acetamide |
| 22 | 2-[4-(4-Chloro-2-hydroxymethyl-phenylamino)-piperidin-1-yl]-N-quinolin-5-yl-acetamide |
| 23 | 2-[4-(4-Fluoro-2-hydroxymethyl-phenylamino)-piperidin-1-yl]-N-quinolin-5-yl-acetamide |
| 24 | 2-[4-(3-Chloro-2-hydroxymethyl-phenylamino)-piperidin-1-yl]-N-quinolin-5-yl-acetamide |
| 25 | 2-[4-(4-Chloro-2-hydroxymethyl-phenylamino)-piperidin-1-yl]-N-quinolin-6-yl-acetamide |
| 26 | 2-[4-(4-Fluoro-2-hydroxymethyl-phenylamino)-piperidin-1-yl]-N-quinolin-6-yl-acetamide |
| 27 | 2-[4-(3-Chloro-2-hydroxymethyl-phenylamino)-piperidin-1-yl]-N-quinolin-6-yl-acetamide |
| 28 | 2-[4-(2-Hydroxymethyl-6-methoxy-phenylamino)-piperidin-1-yl]-N-quinolin-6-yl-acetamide |
| 29 | 2-[4-(4,5-Difluoro-2-hydroxymethyl-phenylamino)-piperidin-1-yl]-N-quinolin-6-yl-acetamide |
| 30 | 2-[4-(4-Chloro-2-hydroxymethyl-phenylamino)-piperidin-1-yl]-N-quinolin-8-yl-acetamide |
| 31 | 2-[4-(4-Fluoro-2-hydroxymethyl-phenylamino)-piperidin-1-yl]-N-quinolin-8-yl-acetamide |
| 32 | 2-[4-(3-Chloro-2-hydroxymethyl-phenylamino)-piperidin-1-yl]-N-quinolin-8-yl-acetamide |
| 33 | N-(4-Benzoyl-phenyl)-2-[4-(4-chloro-2-hydroxymethyl-phenylamino)-piperidin-1-yl]-acetamide |
| 34 | N-(4-Benzoyl-phenyl)-2-[4-(4-fluoro-2-hydroxymethyl-phenylamino)-piperidin-1-yl]-acetamide |
| 35 | N-(4-Benzoyl-phenyl)-2-[4-(2-hydroxymethyl-6-methoxy-phenylamino)-piperidin-1-yl]-acetamide |
| 36 | N-(4-Benzoyl-phenyl)-2-[4-(3-chloro-2-hydroxymethyl-phenylamino)-piperidin-1-yl]-acetamide |
| 37 | 2-[4-(2-Hydroxymethyl-phenylamino)-piperidin-1-yl]-N-[4-(hydroxy-phenyl-methyl)-phenyl]-acetamide |
| 38 | 2-[4-(2-Hydroxymethyl-6-methyl-phenylamino)-piperidin-1-yl]-N-[4-(hydroxy-phenyl-methyl)-phenyl]-acetamide |
| 39 | 2-[4-(4-Chloro-2-hydroxymethyl-phenylamino)-piperidin-1-yl]-N-[4-(hydroxy-phenyl-methyl)-phenyl]-acetamide |
| 40 | 2-[4-(2-Hydroxymethyl-4-methyl-phenylamino)-piperidin-1-yl]-N-[4-(hydroxy-phenyl-methyl)-phenyl]-acetamide |
| 41 | 2-[4-(4-Fluoro-2-hydroxymethyl-phenylamino)-piperidin-1-yl]-N-[4-(hydroxy-phenyl-methyl)-phenyl]-acetamide |
| 42 | 2-[4-(2-Hydroxymethyl-6-methoxy-phenylamino)-piperidin-1-yl]-N-[4-(hydroxy-phenyl-methyl)-phenyl]-acetamide |
| 43 | 2-[4-(3-Chloro-2-hydroxymethyl-phenylamino)-piperidin-1-yl]-N-[4-(hydroxy-phenyl-methyl)-phenyl]-acetamide |
| 44 | 2-[4-(2-Hydroxymethyl-phenylamino)-piperidin-1-yl]-N-(9-oxo-9H-fluoren-3-yl)-acetamide |
| 45 | 2-[4-(4-Chloro-2-hydroxymethyl-phenylamino)-piperidin-1-yl]-N-(9-oxo-9H-fluoren-3-yl)-acetamide |
| 46 | 2-[4-(4-Fluoro-2-hydroxymethyl-phenylamino)-piperidin-1-yl]-N-(9-oxo-9H-fluoren-3-yl)-acetamide |
| 47 | 2-[4-(2-Hydroxymethyl-6-methoxy-phenylamino)-piperidin-1-yl]-N-(9-oxo-9H-fluoren-3-yl)-acetamide |

-continued

| N° | |
|---|---|
| 48 | 2-[4-(4,5-Difluoro-2-hydroxymethyl-phenylamino)-piperidin-1-yl]-N-(9-oxo-9H-fluoren-3-yl)-acetamide |
| 49 | 2-[4-(3-Chloro-2-hydroxymethyl-phenylamino)-piperidin-1-yl]-N-(9-oxo-9H-fluoren-3-yl)-acetamide |
| 50 | N-(9-Hydroxy-9H-fluoren-3-yl)-2-[4-(2-hydroxymethyl-phenylamino)-piperidin-1-yl]-acetamide |
| 51 | 2-[4-(4-Chloro-2-hydroxymethyl-phenylamino)-piperidin-1-yl]-N-(9-hydroxy-9H-fluoren-3-yl)-acetamide |
| 52 | 2-[4-(4-Fluoro-2-hydroxymethyl-phenylamino)-piperidin-1-yl]-N-(9-hydroxy-9H-fluoren-3-yl)-acetamide |
| 53 | N-(9-Hydroxy-9H-fluoren-3-yl)-2-[4-(2-hydroxymethyl-6-methoxy-phenylamino)-piperidin-1-yl]-acetamide |
| 54 | 2-[4-(4,5-Difluoro-2-hydroxymethyl-phenylamino)-piperidin-1-yl]-N-(9-hydroxy-9H-fluoren-3-yl)-acetamide |
| 55 | 2-[4-(3-Chloro-2-hydroxymethyl-phenylamino)-piperidin-1-yl]-N-(9-hydroxy-9H-fluoren-3-yl)-acetamide |
| 56 | N-(3-Acetyl-phenyl)-2-[4-(2-hydroxymethyl-phenylamino)-piperidin-1-yl]-acetamide |
| 57 | N-(3-Acetyl-phenyl)-2-[4-(2-hydroxymethyl-6-methyl-phenylamino)-piperidin-1-yl]-acetamide |
| 58 | N-(3-Acetyl-phenyl)-2-[4-(4-chloro-2-hydroxymethyl-phenylamino)-piperidin-1-yl]-acetamide |
| 59 | N-(3-Acetyl-phenyl)-2-[4-(2-hydroxymethyl-4-methyl-phenylamino)-piperidin-1-yl]-acetamide |
| 60 | N-[3-(1-Hydroxy-ethyl)-phenyl]-2-[4-(2-hydroxymethyl-phenylamino)-piperidin-1-yl]-acetamide |
| 61 | N-[3-(1-Hydroxy-ethyl)-phenyl]-2-[4-(2-hydroxymethyl-6-methyl-phenylamino)-piperidin-1-yl]-acetamide |
| 62 | 2-[4-(4-Chloro-2-hydroxymethyl-phenylamino)-piperidin-1-yl]-N-[3-(1-hydroxy-ethyl)-phenyl]-acetamide |
| 63 | N-[3-(1-Hydroxy-ethyl)-phenyl]-2-[4-(2-hydroxymethyl-4-methyl-phenylamino)-piperidin-1-yl]-acetamide |
| 64 | N-Benzo[1,3]dioxol-5-yl-2-[4-(4-chloro-2-hydroxymethyl-phenylamino)-piperidin-1-yl]-acetamide |
| 65 | N-Benzo[1,3]dioxol-5-yl-2-[4-(4-fluoro-2-hydroxymethyl-phenylamino)-piperidin-1-yl]-acetamide |
| 66 | N-Benzo[1,3]dioxol-5-yl-2-[4-(2-hydroxymethyl-6-methoxy-phenylamino)-piperidin-1-yl]-acetamide |
| 67 | N-Benzo[1,3]dioxol-5-yl-2-[4-(4,5-difluoro-2-hydroxymethyl-phenylamino)-piperidin-1-yl]-acetamide |
| 68 | N-Benzo[1,3]dioxol-5-yl-2-[4-(3-chloro-2-hydroxymethyl-phenylamino)-piperidin-1-yl]-acetamide |
| 69 | N-(4-Acetyl-phenyl)-2-[4-(2-hydroxymethyl-phenylamino)-piperidin-1-yl]-acetamide |
| 70 | N-(4-Acetyl-phenyl)-2-[4-(2-hydroxymethyl-6-methyl-phenylamino)-piperidin-1-yl]-acetamide |
| 71 | N-(4-Acetyl-phenyl)-2-[4-(4-chloro-2-hydroxymethyl-phenylamino)-piperidin-1-yl]-acetamide |
| 72 | N-(4-Acetyl-phenyl)-2-[4-(2-hydroxymethyl-4-methyl-phenylamino)-piperidin-1-yl]-acetamide |
| 73 | N-(4-Acetyl-phenyl)-2-[4-(4-fluoro-2-hydroxymethyl-phenylamino)-piperidin-1-yl]-acetamide |
| 74 | N-(4-Acetyl-phenyl)-2-[4-(2-hydroxymethyl-6-methoxy-phenylamino)-piperidin-1-yl]-acetamide |
| 75 | N-(4-Acetyl-phenyl)-2-[4-(3-chloro-2-hydroxymethyl-phenylamino)-piperidin-1-yl]-acetamide |
| 76 | N-[4-(1-Hydroxy-ethyl)-phenyl]-2-[4-(2-hydroxymethyl-phenylamino)-piperidin-1-yl]-acetamide |
| 77 | N-[4-(1-Hydroxy-ethyl)-phenyl]-2-[4-(2-hydroxymethyl-6-methyl-phenylamino)-piperidin-1-yl]-acetamide |
| 78 | 2-[4-(4-Chloro-2-hydroxymethyl-phenylamino)-piperidin-1-yl]-N-[4-(1-hydroxy-ethyl)-phenyl]-acetamide |
| 79 | N-[4-(1-Hydroxy-ethyl)-phenyl]-2-[4-(2-hydroxymethyl-4-methyl-phenylamino)-piperidin-1-yl]-acetamide |
| 80 | 2-[4-(4-Fluoro-2-hydroxymethyl-phenylamino)-piperidin-1-yl]-N-[4-(1-hydroxy-ethyl)-phenyl]-acetamide |
| 81 | N-[4-(1-Hydroxy-ethyl)-phenyl]-2-[4-(2-hydroxymethyl-6-methoxy-phenylamino)-piperidin-1-yl]-acetamide |
| 82 | 2-[4-(3-Chloro-2-hydroxymethyl-phenylamino)-piperidin-1-yl]-N-[4-(1-hydroxy-ethyl)-phenyl]-acetamide |
| 83 | N-(9-Ethyl-9H-carbazol-3-yl)-2-[4-(2-hydroxymethyl-phenylamino)-piperidin-1-yl]-acetamide |
| 84 | 2-[4-(4-Chloro-2-hydroxymethyl-phenylamino)-piperidin-1-yl]-N-(9-ethyl-9H-carbazol-3-yl)-acetamide |
| 85 | N-(9-Ethyl-9H-carbazol-3-yl)-2-[4-(2-hydroxymethyl-4-methyl-phenylamino)-piperidin-1-yl]-acetamide |
| 86 | N-(9-Ethyl-9H-carbazol-3-yl)-2-[4-(4-fluoro-2-hydroxymethyl-phenylamino)-piperidin-1-yl]-acetamide |
| 87 | N-(9-Ethyl-9H-carbazol-3-yl)-2-[4-(2-hydroxymethyl-6-methoxy-phenylamino)-piperidin-1-yl]-acetamide |
| 88 | 2-[4-(4,5-Difluoro-2-hydroxymethyl-phenylamino)-piperidin-1-yl]-N-(9-ethyl-9H-carbazol-3-yl)-acetamide |
| 89 | 2-[4-(3-Chloro-2-hydroxymethyl-phenylamino)-piperidin-1-yl]-N-(9-ethyl-9H-carbazol-3-yl)-acetamide |
| 90 | 2-[4-(2-Hydroxymethyl-phenylamino)-piperidin-1-yl]-N-(9-methyl-9H-carbazol-3-yl)-acetamide |
| 91 | 2-[4-(2-Hydroxymethyl-6-methyl-phenylamino)-piperidin-1-yl]-N-(9-methyl-9H-carbazol-3-yl)-acetamide |
| 92 | 2-[4-(4-Chloro-2-hydroxymethyl-phenylamino)-piperidin-1-yl]-N-(9-methyl-9H-carbazol-3-yl)-acetamide |
| 93 | 2-[4-(2-Hydroxymethyl-4-methyl-phenylamino)-piperidin-1-yl]-N-(9-methyl-9H-carbazol-3-yl)-acetamide |
| 94 | 2-[4-(2-Hydroxymethyl-phenylamino)-piperidin-1-yl]-N-(5-oxo-5,6,7,8-tetrahydro-naphthalen-2-yl)-acetamide |
| 95 | 2-[4-(2-Hydroxymethyl-6-methyl-phenylamino)-piperidin-1-yl]-N-(5-oxo-5,6,7,8-tetrahydro-naphthalen-2-yl)-acetamide |
| 96 | 2-[4-(4-Chloro-2-hydroxymethyl-phenylamino)-piperidin-1-yl]-N-(5-oxo-5,6,7,8-tetrahydro-naphthalen-2-yl)-acetamide |
| 97 | 2-[4-(2-Hydroxymethyl-4-methyl-phenylamino)-piperidin-1-yl]-N-(5-oxo-5,6,7,8-tetrahydro-naphthalen-2-yl)-acetamide |
| 98 | 2-[4-(4-Fluoro-2-hydroxymethyl-phenylamino)-piperidin-1-yl]-N-(5-oxo-5,6,7,8-tetrahydro-naphthalen-2-yl)-acetamide |
| 99 | 2-[4-(2-Hydroxymethyl-phenylamino)-piperidin-1-yl]-N-(5-hydroxy-5,6,7,8-tetrahydro-naphthalen-2-yl)-acetamide |
| 100 | 2-[4-(2-Hydroxymethyl-6-methyl-phenylamino)-piperidin-1-yl]-N-(5-hydroxy-5,6,7,8-tetrahydro-naphthalen-2-yl)-acetamide |
| 101 | 2-[4-(4-Chloro-2-hydroxymethyl-phenylamino)-piperidin-1-yl]-N-(5-hydroxy-5,6,7,8-tetrahydro-naphthalen-2-yl)-acetamide |
| 102 | 2-[4-(2-Hydroxymethyl-4-methyl-phenylamino)-piperidin-1-yl]-N-(5-hydroxy-5,6,7,8-tetrahydro-naphthalen-2-yl)-acetamide |
| 103 | 2-[4-(4-Fluoro-2-hydroxymethyl-phenylamino)-piperidin-1-yl]-N-(5-hydroxy-5,6,7,8-tetrahydro-naphthalen-2-yl)-acetamide |
| 104 | 2-[4-(2-Hydroxymethyl-6-methyl-phenylamino)-piperidin-1-yl]-N-(1-oxo-indan-5-yl)-acetamide |
| 105 | 2-[4-(4-Chloro-2-hydroxymethyl-phenylamino)-piperidin-1-yl]-N-(1-oxo-indan-5-yl)-acetamide |
| 106 | 2-[4-(2-Hydroxymethyl-4-methyl-phenylamino)-piperidin-1-yl]-N-(1-oxo-indan-5-yl)-acetamide |
| 107 | N-(1-Hydroxy-indan-5-yl)-2-[4-(2-hydroxymethyl-phenylamino)-piperidin-1-yl]-acetamide |
| 108 | N-(1-Hydroxy-indan-5-yl)-2-[4-(2-hydroxymethyl-6-methyl-phenylamino)-piperidin-1-yl]-acetamide |
| 109 | 2-[4-(4-Chloro-2-hydroxymethyl-phenylamino)-piperidin-1-yl]-N-(1-hydroxy-indan-5-yl)-acetamide |
| 110 | N-(1-Hydroxy-indan-5-yl)-2-[4-(2-hydroxymethyl-4-methyl-phenylamino)-piperidin-1-yl]-acetamide |
| 111 | 2-[4-(4-Bromo-2-hydroxymethyl-phenylamino)-piperidin-1-yl]-N-(9-ethyl-9H-carbazol-3-yl)-acetamide |
| 112 | 2-[4-(2-Hydroxymethyl-6-methyl-phenylamino)-piperidin-1-yl]-N-(9-oxo-9H-fluoren-2-yl)-acetamide |
| 113 | 2-[4-(2-Hydroxymethyl-4-methyl-phenylamino)-piperidin-1-yl]-N-(9-oxo-9H-fluoren-2-yl)-acetamide |
| 114 | N-Dibenzofuran-2-yl-2-[4-(2-hydroxymethyl-4-methyl-phenylamino)-piperidin-1-yl]-acetamide |
| 115 | N-Dibenzofuran-2-yl-2-[4-(2-hydroxymethyl-6-methyl-phenylamino)-piperidin-1-yl]-acetamide |
| 116 | 2-[4-(2-Hydroxymethyl-6-methoxy-phenylamino)-piperidin-1-yl]-N-quinolin-3-yl-acetamide |

-continued

| N° | |
|---|---|
| 117 | 2-[4-(4,5-Difluoro-2-hydroxymethyl-phenylamino)-piperidin-1-yl]-N-quinolin-3-yl-acetamide |
| 118 | N-(9-Hydroxy-9H-fluoren-2-yl)-2-[4-(2-hydroxymethyl-6-methyl-phenylamino)-piperidin-1-yl]-acetamide |
| 119 | N-(9-Hydroxy-9H-fluoren-2-yl)-2-[4-(2-hydroxymethyl-4-methyl-phenylamino)-piperidin-1-yl]-acetamide |
| 120 | 2-[4-(2-Hydroxymethyl-phenylamino)-piperidin-1-yl]-N-(4-phenoxy-phenyl)-acetamide |
| 121 | 2-[4-(2-Hydroxymethyl-6-methyl-phenylamino)-piperidin-1-yl]-N-(4-phenoxy-phenyl)-acetamide |
| 122 | 2-[4-(4-Chloro-2-hydroxymethyl-phenylamino)-piperidin-1-yl]-N-(4-phenoxy-phenyl)-acetamide |
| 123 | 2-[4-(2-Hydroxymethyl-4-methyl-phenylamino)-piperidin-1-yl]-N-(4-phenoxy-phenyl)-acetamide |
| 124 | N-(4-Cyclohexyl-phenyl)-2-[4-(2-hydroxymethyl-phenylamino)-piperidin-1-yl]-acetamide |
| 125 | 2-[4-(2-Hydroxymethyl-3-methoxy-phenylamino)-piperidin-1-yl]-N-quinolin-3-yl-acetamide |
| 126 | 2-[4-(3-Hydroxy-2-hydroxymethyl-phenylamino)-piperidin-1-yl]-N-quinolin-3-yl-acetamide |
| 127 | 2-[4-(4-Hydroxy-2-hydroxymethyl-phenylamino)-piperidin-1-yl]-N-quinolin-3-yl-acetamide |
| 128 | 2-[4-(2-Hydroxy-6-hydroxymethyl-phenylamino)-piperidin-1-yl]-N-quinolin-3-yl-acetamide |
| 129 | 2-[4-(2-Hydroxymethyl-3-methoxy-phenylamino)-piperidin-1-yl]-N-quinolin-6-yl-acetamide |
| 130 | 2-[4-(3-Hydroxy-2-hydroxymethyl-phenylamino)-piperidin-1-yl]-N-quinolin-6-yl-acetamide |
| 131 | 2-[4-(4-Hydroxy-2-hydroxymethyl-phenylamino)-piperidin-1-yl]-N-quinolin-6-yl-acetamide |
| 132 | 2-[4-(2-Hydroxy-6-hydroxymethyl-phenylamino)-piperidin-1-yl]-N-quinolin-6-yl-acetamide |
| 133 | N-(4-Benzoyl-phenyl)-2-[4-(2-hydroxymethyl-3-methoxy-phenylamino)-piperidin-1-yl]-acetamide |
| 134 | N-(4-Benzoyl-phenyl)-2-[4-(3-hydroxy-2-hydroxymethyl-phenylamino)-piperidin-1-yl]-acetamide |
| 135 | N-(4-Benzoyl-phenyl)-2-[4-(4-hydroxy-2-hydroxymethyl-phenylamino)-piperidin-1-yl]-acetamide |
| 136 | N-(4-Benzoyl-phenyl)-2-[4-(2-hydroxy-6-hydroxymethyl-phenylamino)-piperidin-1-yl]-acetamide |
| 137 | 2-[4-(2-Hydroxymethyl-3-methoxy-phenylamino)-piperidin-1-yl]-N-[4-(hydroxy-phenyl-methyl)-phenyl]-acetamide |
| 138 | 2-[4-(3-Hydroxy-2-hydroxymethyl-phenylamino)-piperidin-1-yl]-N-[4-(hydroxy-phenyl-methyl)-phenyl]-acetamide |
| 139 | 2-[4-(4-Hydroxy-2-hydroxymethyl-phenylamino)-piperidin-1-yl]-N-[4-(hydroxy-phenyl-methyl)-phenyl]-acetamide |
| 140 | 2-[4-(2-Hydroxy-6-hydroxymethyl-phenylamino)-piperidin-1-yl]-N-[4-(hydroxy-phenyl-methyl)-phenyl]-acetamide |
| 141 | 2-[4-(2-Hydroxymethyl-3-methoxy-phenylamino)-piperidin-1-yl]-N-(9-oxo-9H-fluoren-3-yl)-acetamide |
| 142 | 2-[4-(3-Hydroxy-2-hydroxymethyl-phenylamino)-piperidin-1-yl]-N-(9-oxo-9H-fluoren-3-yl)-acetamide |
| 143 | 2-[4-(4-Hydroxy-2-hydroxymethyl-phenylamino)-piperidin-1-yl]-N-(9-oxo-9H-fluoren-3-yl)-acetamide |
| 144 | 2-[4-(2-Hydroxy-6-hydroxymethyl-phenylamino)-piperidin-1-yl]-N-(9-oxo-9H-fluoren-3-yl)-acetamide |
| 145 | N-(9-Hydroxy-9H-fluoren-3-yl)-2-[4-(2-hydroxymethyl-3-methoxy-phenylamino)-piperidin-1-yl]-acetamide |
| 146 | N-(9-Hydroxy-9H-fluoren-3-yl)-2-[4-(3-hydroxy-2-hydroxymethyl-phenylamino)-piperidin-1-yl]-acetamide |
| 147 | N-(9-Hydroxy-9H-fluoren-3-yl)-2-[4-(4-hydroxy-2-hydroxymethyl-phenylamino)-piperidin-1-yl]-acetamide |
| 148 | N-(9-Hydroxy-9H-fluoren-3-yl)-2-[4-(2-hydroxy-6-hydroxymethyl-phenylamino)-piperidin-1-yl]-acetamide |
| 149 | N-(3-Acetyl-phenyl)-2-[4-(2-hydroxymethyl-3-methoxy-phenylamino)-piperidin-1-yl]-acetamide |
| 150 | N-(3-Acetyl-phenyl)-2-[4-(3-hydroxy-2-hydroxymethyl-phenylamino)-piperidin-1-yl]-acetamide |
| 151 | N-(3-Acetyl-phenyl)-2-[4-(4-hydroxy-2-hydroxymethyl-phenylamino)-piperidin-1-yl]-acetamide |
| 152 | N-(3-Acetyl-phenyl)-2-[4-(2-hydroxy-6-hydroxymethyl-phenylamino)-piperidin-1-yl]-acetamide |
| 153 | N-[3-(1-Hydroxy-ethyl)-phenyl]-2-[4-(2-hydroxymethyl-3-methoxy-phenylamino)-piperidin-1-yl]-acetamide |
| 154 | N-[3-(1-Hydroxy-ethyl)-phenyl]-2-[4-(3-hydroxy-2-hydroxymethyl-phenylamino)-piperidin-1-yl]-acetamide |
| 155 | N-[3-(1-Hydroxy-ethyl)-phenyl]-2-[4-(4-hydroxy-2-hydroxymethyl-phenylamino)-piperidin-1-yl]-acetamide |
| 156 | N-[3-(1-Hydroxy-ethyl)-phenyl]-2-[4-(2-hydroxy-6-hydroxymethyl-phenylamino)-piperidin-1-yl]-acetamide |
| 157 | N-(4-Acetyl-phenyl)-2-[4-(2-hydroxymethyl-3-methoxy-phenylamino)-piperidin-1-yl]-acetamide |
| 158 | N-(4-Acetyl-phenyl)-2-[4-(3-hydroxy-2-hydroxymethyl-phenylamino)-piperidin-1-yl]-acetamide |
| 159 | N-(4-Acetyl-phenyl)-2-[4-(4-hydroxy-2-hydroxymethyl-phenylamino)-piperidin-1-yl]-acetamide |
| 160 | N-(4-Acetyl-phenyl)-2-[4-(2-hydroxy-6-hydroxymethyl-phenylamino)-piperidin-1-yl]-acetamide |
| 161 | N-[4-(1-Hydroxy-ethyl)-phenyl]-2-[4-(2-hydroxymethyl-3-methoxy-phenylamino)-piperidin-1-yl]-acetamide |
| 162 | N-[4-(1-Hydroxy-ethyl)-phenyl]-2-[4-(3-hydroxy-2-hydroxymethyl-phenylamino)-piperidin-1-yl]-acetamide |
| 163 | N-[4-(1-Hydroxy-ethyl)-phenyl]-2-[4-(4-hydroxy-2-hydroxymethyl-phenylamino)-piperidin-1-yl]-acetamide |
| 164 | N-[4-(1-Hydroxy-ethyl)-phenyl]-2-[4-(2-hydroxy-6-hydroxymethyl-phenylamino)-piperidin-1-yl]-acetamide |
| 165 | N-(9-Ethyl-9H-carbazol-3-yl)-2-[4-(2-hydroxymethyl-3-methoxy-phenylamino)-piperidin-1-yl]-acetamide |
| 166 | N-(9-Ethyl-9H-carbazol-3-yl)-2-[4-(3-hydroxy-2-hydroxymethyl-phenylamino)-piperidin-1-yl]-acetamide |
| 167 | N-(9-Ethyl-9H-carbazol-3-yl)-2-[4-(4-hydroxy-2-hydroxymethyl-phenylamino)-piperidin-1-yl]-acetamide |
| 168 | N-(9-Ethyl-9H-carbazol-3-yl)-2-[4-(2-hydroxy-6-hydroxymethyl-phenylamino)-piperidin-1-yl]-acetamide |
| 169 | 2-[4-(2-Hydroxymethyl-3-methoxy-phenylamino)-piperidin-1-yl]-N-(5-oxo-5,6,7,8-tetrahydro-naphthalen-2-yl)-acetamide |
| 170 | 2-[4-(3-Hydroxy-2-hydroxymethyl-phenylamino)-piperidin-1-yl]-N-(5-oxo-5,6,7,8-tetrahydro-naphthalen-2-yl)-acetamide |
| 171 | 2-[4-(4-Hydroxy-2-hydroxymethyl-phenylamino)-piperidin-1-yl]-N-(5-oxo-5,6,7,8-tetrahydro-naphthalen-2-yl)-acetamide |
| 172 | 2-[4-(2-Hydroxy-6-hydroxymethyl-phenylamino)-piperidin-1-yl]-N-(5-oxo-5,6,7,8-tetrahydro-naphthalen-2-yl)-acetamide |
| 173 | 2-[4-(2-Hydroxymethyl-3-methoxy-phenylamino)-piperidin-1-yl]-N-(5-hydroxy-5,6,7,8-tetrahydro-naphthalen-2-yl)-acetamide |
| 174 | 2-[4-(3-Hydroxy-2-hydroxymethyl-phenylamino)-piperidin-1-yl]-N-(5-hydroxy-5,6,7,8-tetrahydro-naphthalen-2-yl)-acetamide |
| 175 | 2-[4-(4-Hydroxy-2-hydroxymethyl-phenylamino)-piperidin-1-yl]-N-(5-hydroxy-5,6,7,8-tetrahydro-naphthalen-2-yl)-acetamide |
| 176 | 2-[4-(2-Hydroxy-6-hydroxymethyl-phenylamino)-piperidin-1-yl]-N-(5-hydroxy-5,6,7,8-tetrahydro-naphthalen-2-yl)-acetamide |
| 177 | 2-[4-(2-Hydroxymethyl-3-methoxy-phenylamino)-piperidin-1-yl]-N-(4-phenoxy-phenyl)-acetamide |
| 178 | 2-[4-(3-Hydroxy-2-hydroxymethyl-phenylamino)-piperidin-1-yl]-N-(4-phenoxy-phenyl)-acetamide |
| 179 | 2-[4-(4-Hydroxy-2-hydroxymethyl-phenylamino)-piperidin-1-yl]-N-(4-phenoxy-phenyl)-acetamide |
| 180 | 2-[4-(2-Hydroxy-6-hydroxymethyl-phenylamino)-piperidin-1-yl]-N-(4-phenoxy-phenyl)-acetamide | optionally in form of one of its stereoisomers, preferably enantiomers or diastereomers, its racemate or in form of a mixture of at least two of its stereoisomers, preferably enantiomers or diastereomers, in any mixing ratio, or a salt, preferably a physiologically acceptable salt thereof.

3. The compound according to claim 1 selected from the group consisting of:

[1] N-(9-Ethyl-9H-carbazol-3-yl)-2-[4-(2-hydroxymethyl-6-methylphenylamino)-piperidine-yl]acetamide;

[2] 2-[4-(2-Hydroxymethyl-4-methyl-phenylamino)-piperidine-1-yl]-N-(9-oxo-9H-fluoren-3-yl)-acetamide;

[3] 2-[4-(2-Hydroxymethyl-6-methyl-phenylamino)-piperidine-1-yl-]-N-(9-oxo-9H-fluoren-3-yl)-acetamide;

[4] N-(9-Hydroxy-9H-fluoren-3-yl)-2-[4-(2-hydroxymethyl-4-methylphenylamino)-piperidine-1-yl]-acetamide;

[5] N-(9-Hydroxy-9H-fluoren-3-yl)-2-[4-(2-hydroxymethyl-6-methylphenylamino)-piperidine-1yl]-acetamide;

[6] 2-{1-[(9-Oxo-9H-fluoren-3ylcarbamoyl)-methyl]-piperidin-4 ylamino}benzoic acid methyl ester,

[7] 2-[4-(2-Hydroxymethyl-4-methyl-phenylamino)-piperidin-1-yl]-N-phenyl-acetamide, and

[8] 2-[4-(2-Hydroxymethyl-phenylamino)-piperidin-1-yl]-N-(1-oxo-indan-5-yl)-acetamide, optionally in form of a salt.

4. A composition comprising at least one 1,4-disubstituted piperidine compound according to claim 1, optionally in form of one of its stereoisomers, its racemate or in form of a mixture of at least two of its stereoisomers in any mixing ratio, or a physiologically acceptable salt thereof, and one or more pharmaceutically acceptable adjuvants.

5. A composition comprising at least one 1,4-disubstituted piperidine compound according to claim 2, optionally in form of one of its stereoisomers, its racemate, in form of a mixture of at least two of its stereoisomers in any mixing ratio, a physiologically acceptable salt thereof, and one or more pharmaceutically acceptable adjuvants.

6. A composition comprising at least one 1,4-disubstituted piperidine compound according to claim 3, optionally in form of one of its stereoisomers, its racemate, in form of a mixture of at least two of its stereoisomers in any mixing ratio, a physiologically acceptable salt thereof, and one or more pharmaceutically acceptable adjuvants.

* * * * *